（12）United States Patent
Miller et al.

(10) Patent No.: US 7,608,818 B2
(45) Date of Patent: Oct. 27, 2009

(54) COMPACT GAS CHROMATOGRAPHY AND ION MOBILITY BASED SAMPLE ANALYSIS SYSTEMS, METHODS, AND DEVICES

(75) Inventors: Raanan A. Miller, Chestnut Hill, MA (US); Erkinjon G. Nazarov, Lexington, MA (US); David B. Wheeler, Lunenburg, MA (US); Kenneth A. Markoski, Westford, MA (US)

(73) Assignee: Sionex Corporation, Bedford, MA (US)

( * ) Notice: Subject to any disclaimer, the term of this patent is extended or adjusted under 35 U.S.C. 154(b) by 152 days.

(21) Appl. No.: 11/415,564

(22) Filed: May 1, 2006

(65) Prior Publication Data

US 2007/0029477 A1     Feb. 8, 2007

Related U.S. Application Data

(60) Provisional application No. 60/675,960, filed on Apr. 29, 2005, provisional application No. 60/688,735, filed on Jun. 8, 2005, provisional application No. 60/753,300, filed on Dec. 21, 2005, provisional application No. 60/791,075, filed on Apr. 11, 2006.

(51) Int. Cl.
B01D 59/44     (2006.01)
(52) U.S. Cl. .................. 250/288; 250/281; 250/282; 250/286; 250/287
(58) Field of Classification Search .......... 250/281, 250/282, 286, 287, 288; 96/101, 102, 103; 422/89, 83; 95/82, 86, 87; 73/23.2, 23.22, 73/23.25
See application file for complete search history.

(56) References Cited

U.S. PATENT DOCUMENTS 2,615,135 A     10/1952    Glenn 3,511,986 A     5/1970    Llewellyn
3,621,240 A     11/1971    Cohen et al.
3,931,589 A     1/1976    Aisenberg et al.

(Continued)

FOREIGN PATENT DOCUMENTS

EP     0 574 027    12/1993

(Continued)

OTHER PUBLICATIONS

"A Micromachined Field Driven Radio Frequency-Ion Mobility Spectrometer for Trace Level Chemical Detection,"A Draper Laboratory Proposal Against the "Advanced Cross-Enterprise Technology Development for NASA Missions,"Solicitation, NASA NRA 99-OSS-05.

(Continued)

Primary Examiner—David A Vanore
Assistant Examiner—Michael Maskell
(74) Attorney, Agent, or Firm—Ropes & Gray LLP

(57) ABSTRACT

A compact integrated ion mobility based analysis system includes at least one gas chromatograph (GC) column that receives a sample and elutes constituents of the sample where each of the eluted constituents are temporally separated from each other The system also includes at least one ion mobility based sample analyzer that analyzes the eluted constituents based on their ion mobility characteristics. The system further includes a controller that selectively adjusts the temperature within at least one GC column over a period of time and selectively adjusts the temperature within at least one ion mobility based sample analyzer over a period of time.

44 Claims, 52 Drawing Sheets

U.S. PATENT DOCUMENTS

| | | | |
|---|---|---|---|
| 4,025,818 A | 5/1977 | Giguere et al. | |
| 4,201,921 A | 5/1980 | McCorkle | |
| 4,805,441 A * | 2/1989 | Sides et al. | 73/23.25 |
| 4,923,486 A * | 5/1990 | Rubey | 95/87 |
| 4,931,640 A | 6/1990 | Marshall et al. | |
| 5,019,706 A | 5/1991 | Allemann et al. | |
| 5,028,243 A * | 7/1991 | Rubey | 95/87 |
| 5,196,039 A * | 3/1993 | Phillips et al. | 210/656 |
| 5,420,424 A | 5/1995 | Carnahan et al. | |
| 5,455,417 A | 10/1995 | Sacristan | |
| 5,536,939 A | 7/1996 | Freidhoff et al. | |
| 5,654,544 A | 8/1997 | Dresch | |
| 5,723,861 A | 3/1998 | Carnahan et al. | |
| 5,736,739 A * | 4/1998 | Uber et al. | 250/287 |
| 5,763,876 A * | 6/1998 | Pertinarides et al. | 250/288 |
| 5,789,745 A | 8/1998 | Martin et al. | |
| 5,801,379 A | 9/1998 | Kouznetsov | |
| 5,811,059 A * | 9/1998 | Genovese et al. | 422/89 |
| 5,834,771 A | 11/1998 | Yoon et al. | |
| 5,838,003 A | 11/1998 | Bertsch et al. | |
| 5,869,344 A | 2/1999 | Linforth et al. | |
| 5,965,882 A | 10/1999 | Megerle et al. | |
| 6,066,848 A | 5/2000 | Kassel et al. | |
| 6,124,592 A | 9/2000 | Spangler | |
| 6,257,047 B1 * | 7/2001 | Grob et al. | 73/23.42 |
| 6,323,482 B1 | 11/2001 | Clemmer et al. | |
| 6,495,823 B1 * | 12/2002 | Miller et al. | 250/286 |
| 6,498,342 B1 | 12/2002 | Clemmer | |
| 6,504,149 B2 | 1/2003 | Guevremont et al. | |
| 6,509,562 B1 | 1/2003 | Yang et al. | |
| 6,512,224 B1 | 1/2003 | Miller et al. | |
| 6,559,441 B2 * | 5/2003 | Clemmer | 250/287 |
| 6,639,212 B1 | 10/2003 | Guevremont | |
| 6,653,627 B2 | 11/2003 | Guevremont | |
| 6,690,004 B2 | 2/2004 | Miller et al. | |
| 6,703,609 B2 | 3/2004 | Guevremont | |
| 6,713,758 B2 | 3/2004 | Guevremont | |
| 6,727,496 B2 | 4/2004 | Miller et al. | |
| 6,744,043 B2 | 6/2004 | Loboda | |
| 6,753,522 B2 | 6/2004 | Guevremont | |
| 6,770,875 B1 | 8/2004 | Guevremont | |
| 6,774,360 B2 | 8/2004 | Guevremont | |
| 6,787,765 B2 | 9/2004 | Guevremont | |
| 6,799,355 B2 | 10/2004 | Guevremont | |
| 6,806,463 B2 | 10/2004 | Miller et al. | |
| 6,806,466 B2 | 10/2004 | Guevremont | |
| 6,815,668 B2 * | 11/2004 | Miller et al. | 250/286 |
| 6,815,669 B1 | 11/2004 | Miller et al. | |
| 6,822,224 B2 | 11/2004 | Guevremont et al. | |
| 6,825,461 B2 | 11/2004 | Guevremont et al. | |
| 2001/0030285 A1 * | 10/2001 | Miller et al. | 250/288 |
| 2002/0070338 A1 | 6/2002 | Loboda | |
| 2002/0134932 A1 | 9/2002 | Guevremont et al. | |
| 2003/0020012 A1 | 1/2003 | Guevremont et al. | |
| 2003/0038235 A1 | 2/2003 | Guevremont et al. | |
| 2003/0052263 A1 | 3/2003 | Kaufman et al. | |
| 2003/0070913 A1 | 4/2003 | Miller et al. | |
| 2003/0089847 A1 | 5/2003 | Guevremont et al. | |
| 2003/0132380 A1 | 7/2003 | Miller et al. | |
| 2004/0094704 A1 | 5/2004 | Miller et al. | |
| 2004/0136872 A1 | 7/2004 | Miller et al. | |
| 2004/0194628 A1 * | 10/2004 | Mitra | 96/101 |
| 2004/0232326 A1 | 11/2004 | Guevremont et al. | |
| 2005/0017163 A1 * | 1/2005 | Miller et al. | 250/281 |
| 2005/0029443 A1 * | 2/2005 | Miller et al. | 250/281 |
| 2005/0029449 A1 | 2/2005 | Miller et al. | |
| 2005/0040330 A1 | 2/2005 | Miller et al. | |
| 2005/0051719 A1 | 3/2005 | Miller et al. | |
| 2005/0056780 A1 | 3/2005 | Miller et al. | |
| 2005/0121607 A1 | 6/2005 | Miller et al. | |
| 2005/0133716 A1 | 6/2005 | Miller et al. | |
| 2005/0139762 A1 | 6/2005 | Miller et al. | |
| 2005/0167583 A1 | 8/2005 | Miller et al. | |
| 2005/0173629 A1 | 8/2005 | Miller et al. | |
| 2005/0194527 A1 | 9/2005 | Guevremont et al. | |
| 2005/0194532 A1 | 9/2005 | Guevremont et al. | |
| 2005/0230616 A1 * | 10/2005 | Cameron et al. | 250/287 |

FOREIGN PATENT DOCUMENTS

| | | |
|---|---|---|
| EP | 574027 A2 * | 12/1993 |
| SU | 966583 | 10/1982 |
| SU | 1337934 A2 | 9/1987 |
| SU | 1627984 A2 | 7/1988 |
| SU | 1412447 A3 | 6/1998 |
| SU | 1485808 | 10/1998 |
| WO | WO 92/13622 | 8/1992 |
| WO | WO 00/08454 | 2/2000 |
| WO | WO 00/08455 | 2/2000 |
| WO | WO 00/08456 | 2/2000 |
| WO | WO 00/08457 | 2/2000 |
| WO | WO 01/08197 A1 | 2/2001 |
| WO | WO 01/22049 A2 | 3/2001 |
| WO | WO 01/35441 A1 | 5/2001 |
| WO | WO 01/69217 A2 | 9/2001 |
| WO | WO 01/69220 A2 | 9/2001 |
| WO | WO 01/69647 A2 | 9/2001 |
| WO | WO 02/07185 | 1/2002 |
| WO | WO 02/071053 A | 9/2002 |
| WO | WO-03/067237 A2 | 8/2003 |
| WO | WO-03/067242 A1 | 8/2003 |
| WO | WO-03/067243 A1 | 8/2003 |
| WO | WO-03/067625 A1 | 8/2003 |
| WO | WO 2004/012231 | 2/2004 |
| WO | WO-2004/029603 A2 | 4/2004 |
| WO | WO-2004/029614 A1 | 4/2004 |
| WO | WO-2004/030022 A2 | 4/2004 |
| WO | WO-2004/030023 A2 | 4/2004 |
| WO | WO-2004/030129 A2 | 4/2004 |

OTHER PUBLICATIONS

Barnett, D.A. et al., "Isotope Separation Using High-Field Asymmetric Waveform Ion Mobility Spectrometry," Nuclear Instruments & Methods in Physics Research (200), pp. 179-185, 450(1), 2000.

Buryakov, I.A. et al., A New Method of Separation of Multi-Atomic Ions by Mobility at Atmospheric Pressure Using a High-Frequency Amplitude-Asymmetric Strong Electric Field, International Journal of Mass Spectrometry and Ion Processes (1993), pp. 143-148, 128.

Buryakov, I.A. et al., "Separation of Ions According to Mobility in a Strong AC Electric Field," Sov. Tech. Phs. Lett. (1991), pp. 446-447, 17(6).

Burykov, I.A. et al., Device and Method For Gas Electrophoresis, Chemical Analysis of Environment, edit. Prof. V.V. Malakhov, Novosibirsk; Nauka (1991), pp. 113-127.

Carnahan, B. et al., "Field Ion Spectrometry—A New Analytical Technology for Trace Gas Analysis," ISA, (1996), pp. 87-96, 51(1).

Carnahan, B. et al., "Field Ion Spectrometry—A New Technology for Cocaine and Heroin Detection," SPIE, (1997), pp. 106-119, 2937.

Eiceman, G.A. et al., "Miniature radio-frequency mobility analyzer as a gas chromatographic detector for oxygen-containing volatile organic compounds, pheromones, and other insect attractants," J. Chromatography, (2001), pp. 205-217, 917.

Guevremont, R. and Purves, R., High Field Asymmetric Waveform Ion Mobility Spectrometry-Mass Spectrometry: An Investigation of Leucine Enkephalin Ions Produced by Electrospray Ionization, J. Am. Soc. Mass. Spectrom, (1999), pp. 492-501, 10.

Guevremont, R. et al., "Calculation of Ion Mobilities From Electrospray Ionization High Field Asymmetric Waveform Ion Mobility Spectrometry Mass Spectrometry," Journal of Chemical Physics, (2001), pp. 10270-10277, 114(23).

Guevremont, R. et al., "Atmospheric Pressure In Focusing in a High-Field Asymmetric Waveform ion Mobility Spectrometer," Review of Scientific Instruments, (1999), pp. 1370-1383, 70(2).

Handy, Russell et al., "Determination of nanomlar levels of perchlorate in water by ESI-FAIMS-MS," JAAS (2000), pp. 907-911, 15.

Krylov, E.V., "A Method of Reducing Diffusion Losses in a Drift Spectrometer," Technical Physics, (1999), pp. 113-116, 4d(1).

Krylov, E.V., "Pulses of Special Shapes Formed on a Capacitive Load," Instruments and Experimental Techniques, (1997), pp. 628, 40(5).

Miller, R.A. et al., "A MEMS Radio-Frequency Ion Mobility Spectrometer for Chemical Agent Detection," (Jun. 2000) Proceedings of the 2000 Solid State Sensors and Actuators Workshop, Hilton Head, SC.

Miller, R.A. et al., A MEMS Radio-Frequency Ion Mobility Spectrometer for Chemical Vapor Detection, Sensors and Actuators, (2001), pp. 301-312, A91.

Miller, R.A. et al., A Novel Micromachined High-Field Asymmetric Waveform-Ion Mobility Spectrometer, Sensors and Actuators B, (2000) pp. 300-306, B67(3).

Pilzecker, P. et al., "On-Site Investigations of Gas Insulated Substations Using Ion Mobility Spectrometry for Remote Sensing of SF6 Decomposition," IEEE, (2000), pp. 400-403.

Riegner, D.E. et al., "Qualitative Evaluation of Field Ion Spectrometry for Chemical Warfare Agent Detection," Proceedings of the ASMS Conference on Mass Spectrometry and Allied Topics (Jun. 1997), pp. 473A-473B.

Schneider, A. et al., High Sensitivity GC-FIS for Simultaneous Detection of Chemical Warfare Agents, Mine Safety Appliances Co., Pittsburgh, PA USA, (2000), AT-Process, pp. 124-136, 5(3, 4), Coden: APJCFR ISSN: 1077-419X.

Vaidyanathan, S., et al., "Flow-Injection Electrospray Ionization Mass Spectrometry of Crude Cell Extracts for High-Throughput Bacterial Identification," J. Am. Soc. Mass. Spectrom., (2002) pp. 118-128, 13.

Crylov, E.V., "Comparison of the Planar and Coaxial Field Asymmetrical Waveform Ion Mobility Spectrometer (FAIMS)," International Journal of Mass Spectrometry, 225, (2003) pp. 39-51.

Barnett, D.A. et al., "Evaluation of Carrier Gases for use in High-Field Asymmetric Waveform Ion Mobility Spectrometry," Journal of the American Society for Mass Spectrometry, vol. 11, No. 12, pp. 1125-1133, Dec. 2000.

* cited by examiner

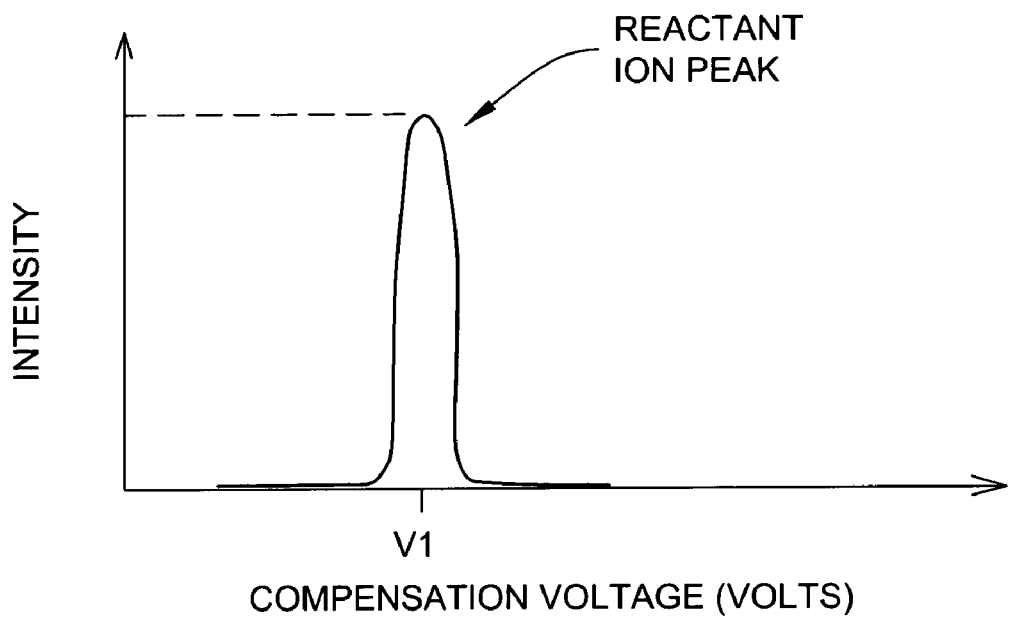
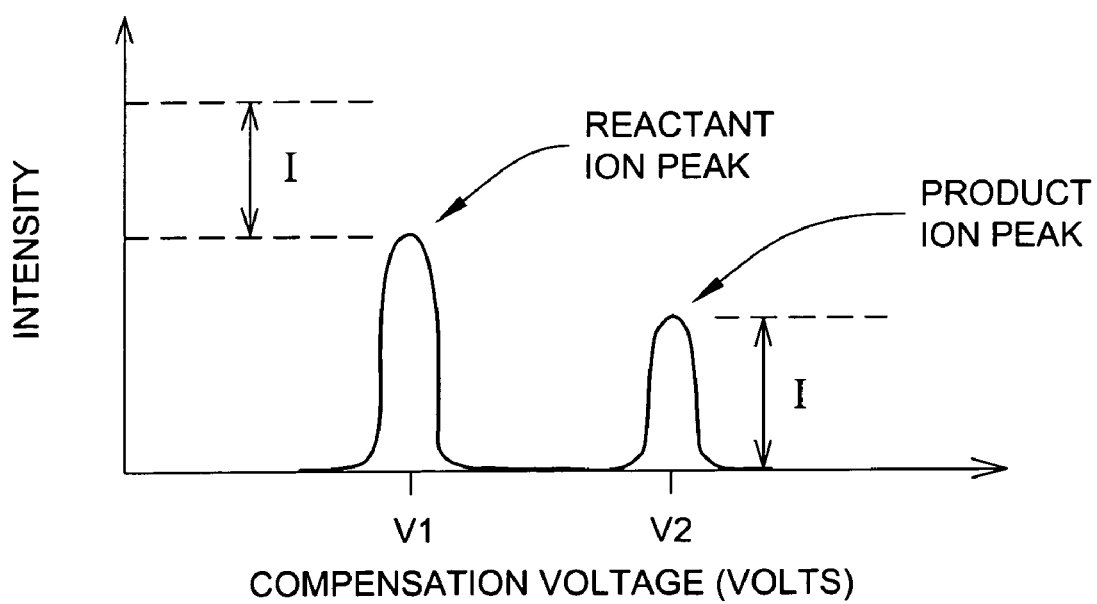
Figure 10

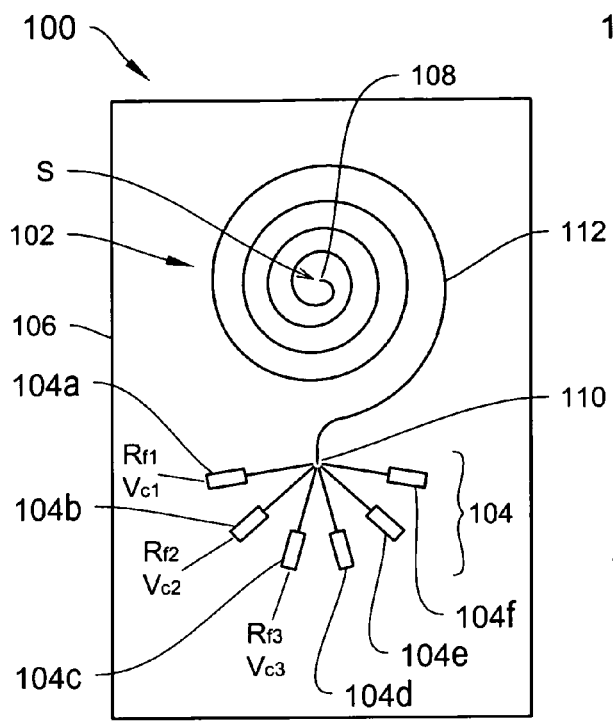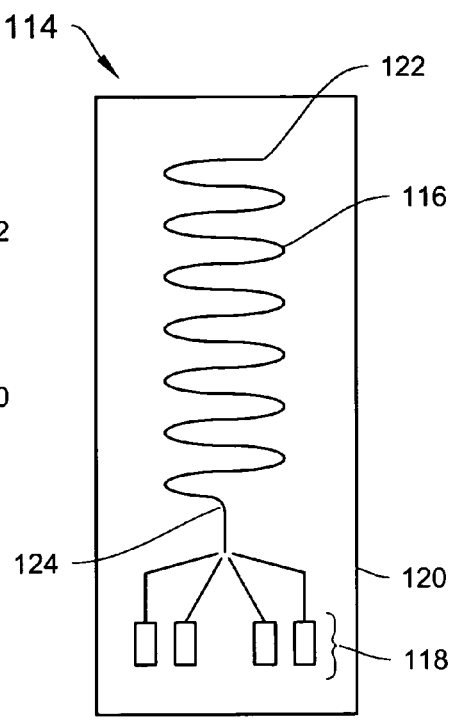
Figure 12A       Figure 12B
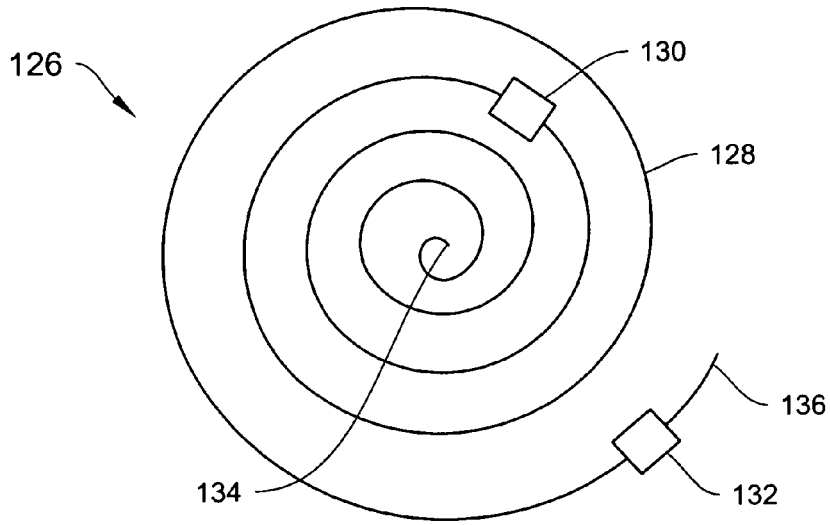
Figure 12C

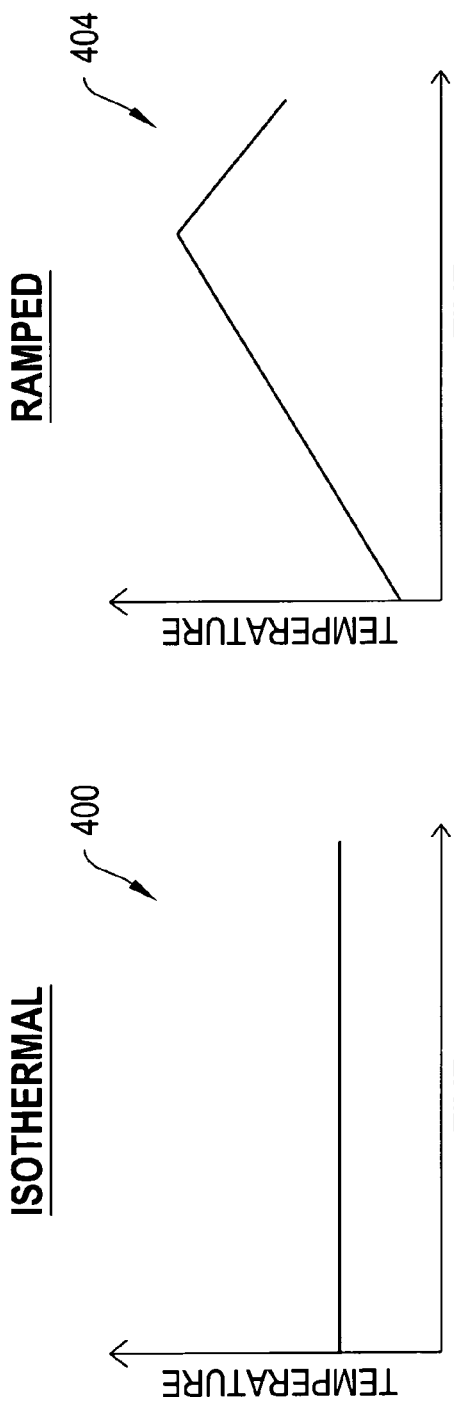
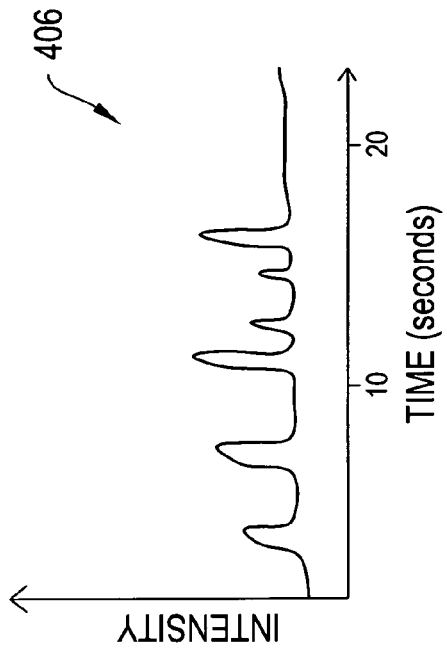
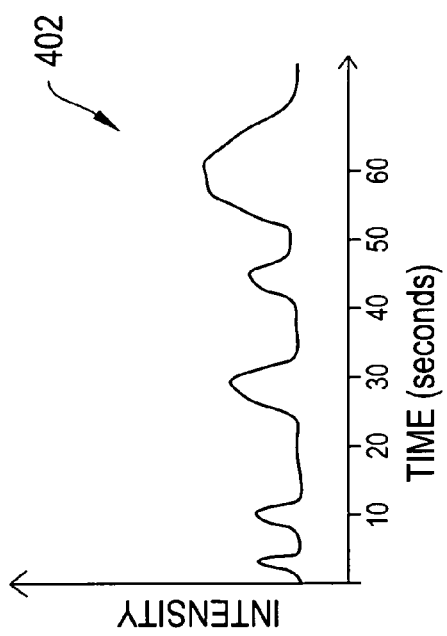
Figure 27A
Figure 27B
Figure 26A
Figure 26B

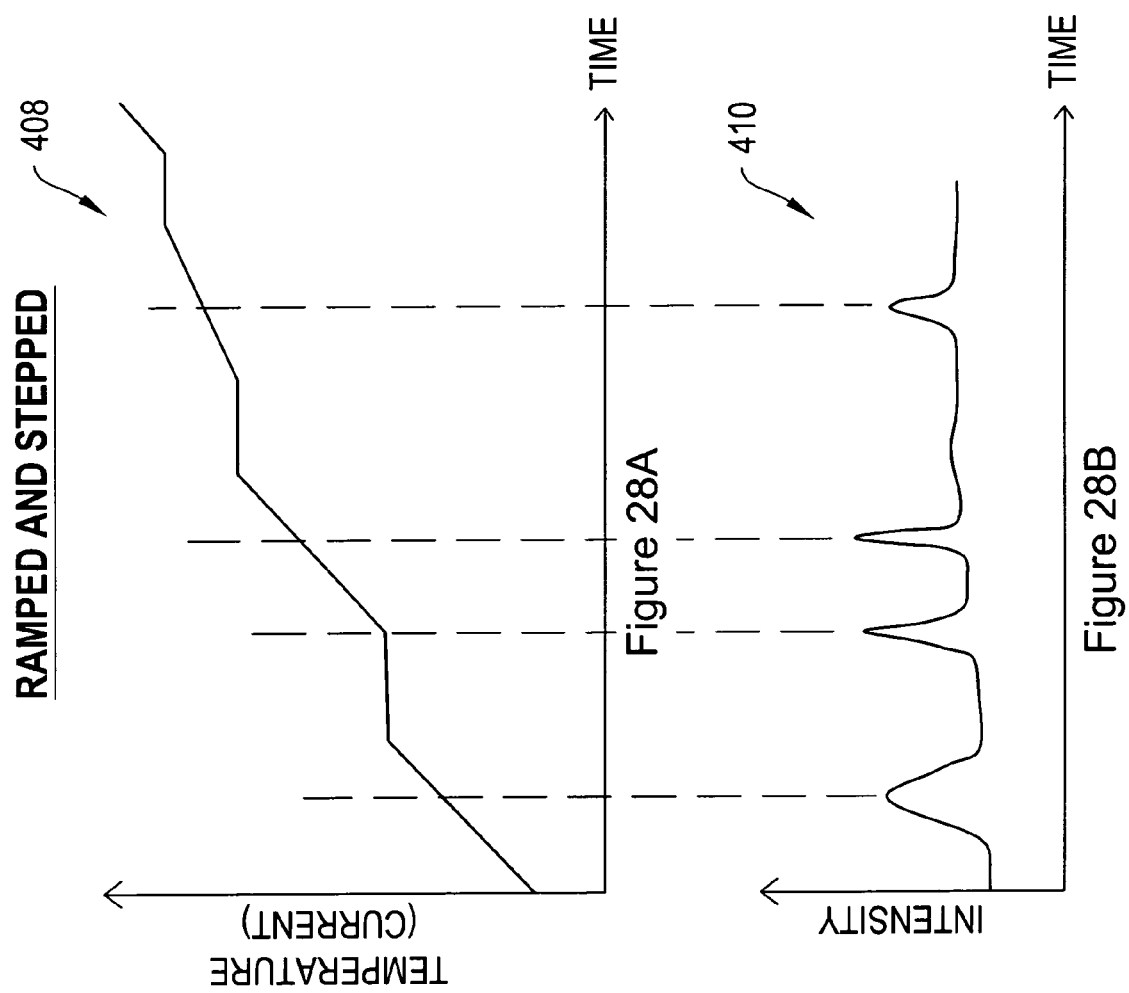

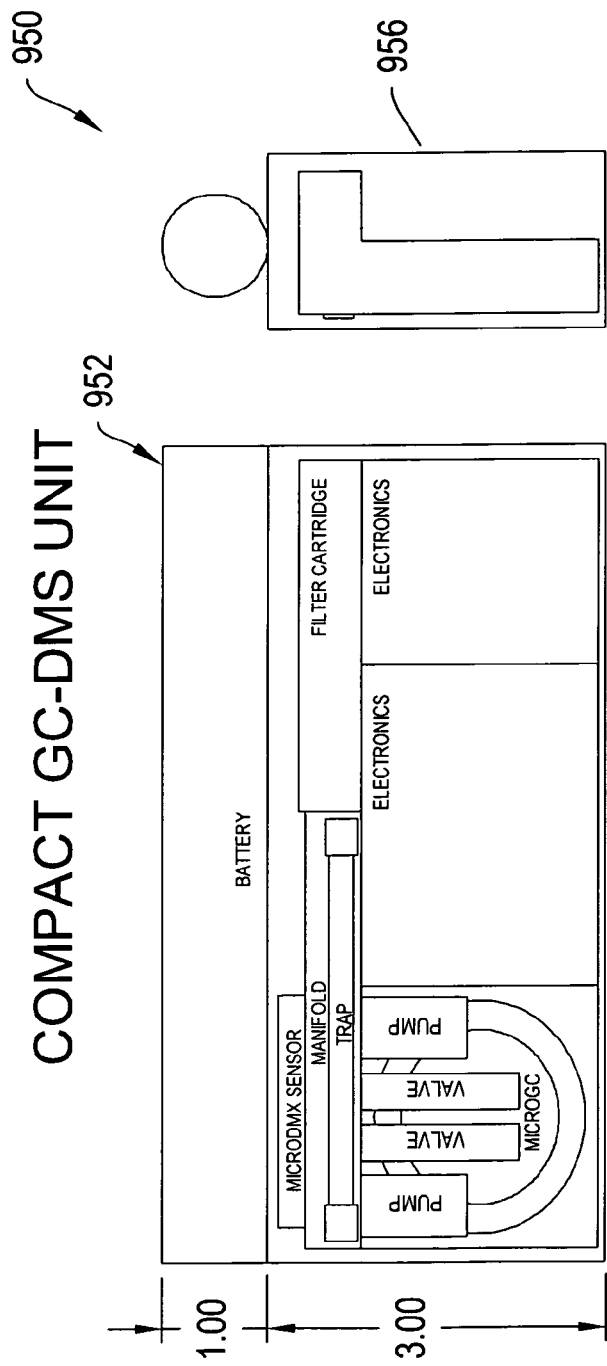
Figure 37A
Figure 37B
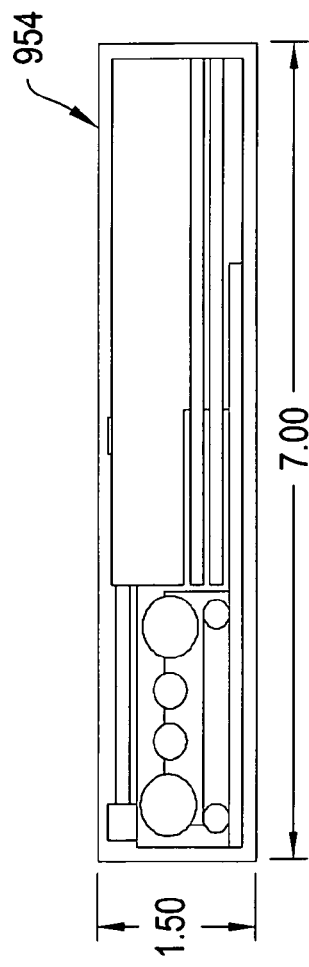
Figure 37C

COMPACT GAS CHROMATOGRAPHY AND ION MOBILITY BASED SAMPLE ANALYSIS SYSTEMS, METHODS, AND DEVICES

REFERENCE TO RELATED APPLICATIONS

This application claims priority to and the benefit of: U.S. Provisional Application No. 60/675,960, filed on Apr. 29, 2005, entitled "Varying Temperature in a Coordinated Manner with Field Conditions in Systems and Methods for Combining Chromatography and Mobility Spectrometry Techniques"; U.S. Provisional Application No. 60/688,735, filed on Jun. 8, 2005, entitled "Fluid Recirculation For Combined Gas Chromatograph and Mobility-Based Analyzer System"; U.S. Provisional Application No. 60/753,300, filed on Dec. 21, 2005, entitled "Integrated Longitudinal Differential Mobility Spectrometer"; U.S. Provisional Application No. 60/791,075, filed on Apr. 11, 2006, entitled "Chromatography and Ion Mobility Based Analysis Systems, Methods, and Devices," all of which are incorporated herein by reference.

This application also incorporates by reference the entire contents of the following co-pending U.S. Patent Applications: U.S. Ser. No. 10/824,674, filed on 14 Apr. 2004; U.S. Ser. No. 10/887,016, filed on 8 Jul. 2004; U.S. Ser. No. 10/894,861, filed on 19 Jul. 2004; U.S. Ser. No. 10/903,497, filed on 30 Jul. 2004; U.S. Ser. No. 10/916,249, filed on 10 Aug. 2004; U.S. Ser. No. 10/932,986, filed on 2 Sep. 2004; U.S. Ser. No. 10/943,523, filed on 17 Sep. 2004; U.S. Ser. No. 10/981,001, filed on 4 Nov. 2004; U.S. Ser. No. 10/998,344, filed 24 Nov. 2004; U.S. Ser. No. 11/015,413, filed on 17 Dec., 2004; U.S. Ser. No. 11/035,800, filed on 13 Jan., 2005; U.S. Ser. No. 11/050,288, filed on 2 Feb. 2005; U.S. Ser. No. 11/070,904, filed on 3 Mar. 2005; U.S. Ser. No. 11/119,048, filed on 28 Apr. 2005; U.S. Ser. No. 11/293,651, filed on 3 Dec. 2005; U.S. Ser. No. 11/305,085, filed on 16 Dec. 2005; and U.S. Ser. No. 11/331,333, filed on 11 Jan. 2006.

FIELD OF THE INVENTION

The invention relates generally to systems, methods and devices for analyzing samples. More particularly, in various embodiments, the invention relates to compact systems and related methods using chromatography in combination with mobility spectrometry to analyze the constituents of a sample.

BACKGROUND

There are a number of different circumstances in which it is desirable to perform analysis to identify and/or measure compounds in a sample. Such samples may be taken directly from the environment or they may be provided by front end specialized devices to separate or prepare compounds before analysis. There exists, a demand for low cost, compact, low-power, accurate, easy to use, and reliable devices capable of detecting compounds in a sample.

One class of known analyzers are gas chromatographs (GC). Gas chromatography is a chemical compound separation method in which a discrete gas sample (composed of a mixture of chemical components) is introduced via an injector arrangement into a GC column. Components of the introduced analyte sample are partitioned between two phases: one phase is a stationary bed with a large surface area, and the other is a gas phase which passes through, or past, the stationary bed. The sample is introduced into the mobile gas phase carrier gas (CG) and carried through the column. The sample partitions (equilibrates) into the stationary phase (often liquid), based on its solubility into the stationary phase material and the temperature of the column. The components of the sample separate from one another based on their relative vapor pressures and affinities for the stationary beds which causes the different compounds to be retained in the GC column for differing amounts of time.

Compounds can be identified by the amount of time they are retained within the GC column. The retention or elusion time (i.e., the time that a compound is retained within the GC column) is typically measured as the time from sample injection into the GC column to the time that a peak concentration/intensity for the compound is measured at a detector.

The prior art teaches two general types of GC columns, packed and capillary (also known as open tubular). Packed columns contain a finely divided, inert, solid support material (commonly based on diatomaceous earth) coated with the liquid stationary phase. Packed columns are typically between about 1.5 meters-about 10 meters in length and have an internal diameter of between about 2 millimeters-about 4 millimeters. Capillary columns typically have an internal diameter of a about a few tenths of a millimeter. They are typically either wall-coated open tubular (WCOT) or support-coated open tubular (SCOT). Wall-coated columns have a capillary tube whose walls are coated with the liquid stationary phase. In support-coated columns, the inner wall of the capillary is lined with a thin layer of support material, such as diatomaceous earth, onto which the stationary phase is adsorbed. SCOT columns are generally less efficient than WCOT columns. Both types of capillary column are more efficient than packed columns.

Ideally, column temperature is controlled to within tenths of a degree. The optimum column temperature is dependant upon the boiling point of the sample. Generally, a temperature slightly above the average boiling point of the sample results in an elution time of 2-30 minutes. Lower temperatures give good resolution, but increase elution times. If a sample has a wide boiling range, then temperature programming can be useful. The column temperature is increased (either continuously or in steps) as separation proceeds.

There are many detectors that can be used with a GC providing different levels of selectivity. For example, a non-selective detector responds to all compounds except the carrier gas, a selective detector responds to a range of compounds with a common physical or chemical property, and a specific detector responds to a single chemical compound. Exemplary detectors include, flame ionization detectors (FID), thermal conductivity detectors (TCD), electron capture detectors (ECD), nitrogen-phosphorus detectors, flame photometric detectors (FPD), photo-ionization detectors (PID) and hall electrolytic conductivity detectors.

Certain components of high speed or portable GC analyzers have reached advanced stages of refinement. These include improved columns and sample injectors, and heaters that achieve precise temperature control of the column. Even so, detectors for portable GCs, generally thermal conductivity based, still suffer from relatively poor detection limits and selectivity. In addition, GC analyzers combined with conventional detectors, such as those mentioned above, produce a signal indicating the presence of a compound eluted from the GC column. However, presence indication alone is often inadequate. It is often desirable to obtain additional specific information about the analyte to enhance compound identification and reduce false positives and negatives.

One conventional approach for obtaining additional information combines a GC with a MS. Mass spectrometers are generally recognized as being the most accurate type of analyzers for compound identification. An advantage of employing a MS with a GC is that the MS provides an orthogonal set of information, based on molecular weight and charge, for each chromatographic peak of the GC. As used herein, the term "orthogonal" means data that is obtained by measuring a different property of the compound during sample analysis to provide multiple levels of relatively independent and accurate information. By providing orthogonal data, use of a MS as the detector increases the accuracy of analytical separation provided by the GC, and in most cases, the combined GC-MS information is sufficient for unambiguous identification of the compound. Unfortunately, the GC-MS is not well suited for portable field-deployable instruments, which need to be small and are desirably low cost. While GC's are continuously being miniaturized and reduced in cost, mass spectrometers are still very expensive, often exceeding $100 k. Mass spectrometers also suffer from other shortcomings, such as the need to operate at relatively low pressures, resulting in complex support systems. They also need a highly trained operator to tend to and interpret the results. Accordingly, mass spectrometers are generally difficult to use outside of laboratories.

Time-of-flight Ion Mobility Spectrometers (TOF-IMS) have also been employed as detectors for GCs, and exhibit functional parallels to MSs. However, despite advances over the past decade, TOF-IMS drift tubes as detectors for GCs have not been widely adopted. For good analytical performance, IMSs must be comparatively large as they suffer from losses in resolution when made small. Thus, field-deployment still remains difficult for GC-TOF-IMSs.

A class of chemical analysis instruments more suitable for field operation is known as Field Asymmetric Ion Mobility Spectrometers (FAIMS) or Differential Mobility Spectrometers (DMS), and also known as Radio Frequency Ion Mobility Spectrometers (RFIMS) among other names. Hereinafter, FAIMS, DMS, and RFIMS, are referred to collectively as DMS.

The DMS filtering technique involves passing ions in a drift gas through strong electric fields between filter electrodes. The fields are created by application of an asymmetric period voltage (typically along with a compensation voltage) to the filter electrodes. The process achieves a filtering effect by accentuating differences in ion mobility. The asymmetric field alternates between a high and low field strength condition, which causes the ions to move in response to the field according to their mobility. Typically, the mobility in the high field differs from that of the low field. That mobility difference produces a net displacement of the ions as they travel in the gas flow through the filter. In the presence of a specific compensation voltage, a particular ion species passes through the filter. The amount of change in mobility in response to the asymmetric field is compound-dependent. This permits separation of ions from each other according to their species, in the presence of an appropriately set compensation field bias.

Fast detection is a sought-after feature of a field deployable detection device. One characteristic of known DMS devices is the relatively slow detection time. However, the GC can operate much more rapidly, such that the known DMS devices cannot generate a complete spectra of the ions present under each GC peak. Therefore, conventional DMS devices are limited to a single compound detection mode if coupled to a GC, with a response time typically of about 10 seconds. Any additional compound that is desired to be measured takes approximately an additional 10 seconds to measure.

While the foregoing arrangements are adequate for a number of applications, there is still a need for a small, field-deployable sample analyzer that can detect certain ion species or discriminate certain species from others in an efficient manner.

SUMMARY

The invention, in various embodiments, addresses deficiencies in the prior art by providing systems, methods and devices for detecting, identifying, measuring and/or analyzing (collectively "analyzing") constituents in a sample. More particularly, the invention provides enhanced system temperature control to improve the detection of certain constituents in the presence of other constituents. The samples and constituents may include any material; chemical or biological, organic or inorganic. In particular embodiments, the invention is directed to a compact gas chromatograph (GC)—differential mobility spectrometer (DMS) combination system, which provides a relatively small, light weight, field-deployable, accurate and fast sample analysis system. In other embodiments, the invention is directed to particular compact DMS configurations, for example, for use in combination with a GC. According to other embodiments, the invention is directed to techniques for controlling and/or varying the temperature within a GC column or an array (series and/or parallel) of GC columns to enhance the detection of certain ion species and enhance the discrimination of certain ion species from others. In a further embodiment, the invention provides a recirculation system in support of the GC-DMS analysis process including sequential sample collection, GC column loading, and DMS analysis phases in a compact GC-DMS system.

According to one aspect, the invention provides a compact integrated ion mobility based analysis system including at least one gas chromatograph (GC) column and at least one ion mobility based sample analyzer. Optionally, the at least one GC and the at least one ion mobility based sample analyzer are formed as an integrated circuit in a single package. The GC column receives a sample and elutes constituents of the sample, each of the eluted constituents being temporally separated from each other. The mobility based sample analyzer receives the eluted constituents from the GC and analyzes them based on their ion mobility characteristics of the eluted constituents. In one feature, a controller selectively adjusts the temperature within the at least one GC column over a period of time to effect enhanced separation between various sample constituents.

In one configuration, the invention employs an array of GC columns. In another configuration, the invention employs first and second GC columns where the first GC column has a different stationary phase than the second GC column. In a further configuration, the invention employs a modulator to trap and focus the concentration of constituents eluted from the first GC column over a period of time and then deliver the constituents to the second GC column.

In one feature, at least one GC column is formed as a capillary column in a substrate. The substrate may include a silicon substrate, a semiconductor substrate, a carbon substrate, a sapphire substrate or a polymer-based substrate, or a ceramic substrate.

In another feature, the ion mobility based sample analyzer provides a plurality of scans for each elution peak of the GC column.

In one configuration, temperature adjusting includes ramping the temperature of at least one GC column over a range of temperatures. The temperatures may be in the range of about 0 to 350° C. In another configuration, adjusting includes stepping the temperature of at least one GC column over a range of temperatures.

In one feature, the invention includes an inlet section for conditioning the sample before introduction into the GC column. The inlet section may include a trap, to accumulate a certain amount of sample to enhance the amount of sample introduced into the GC column. In one configuration, the controller controls the temperature the trap. The range of temperatures within the trap may include about −50 to 1000° C., but temperatures below −50C and about 1000C are also possible. The inlet section may include at least one of a pre-concentrator, an electrospray source, a molecular sieve, a filter, a pyrolizer, an ion mobility based filter, and other like sample conditioners.

According to one configuration, the invention includes a fluid recirculation system for transporting portions of the sample through the GC column and the ion mobility based analyzer. This design enables a highly portable field deployable system which does not require a GC-carrier gas canister of inert gas. The system can run for long periods of time unsupervised. The GC-DMS system can be wirelessly integrated into a wireless or wired network so that data from the system can be collected, transmitted, processed and relayed from remote or field locations. In one feature, a controller controls certain components of the recirculation system to enable sample collection, GC column loading, and ion mobility based analyzer analyzing. The components may include one or more pumps, valves, or vents. In one configuration, the GC-DMS system includes a heater for heating the GC column and/or cooler for cooling the GC column. The cooler and or heater may be a thermo electric device. The cooler may be a fan, or a Freon or other coolant containing system.

In another embodiment, the GC-DMS system, or the DMS system alone were able analyze natural gas samples and other feed stocks of fuel cells to, measure and even quantitate levels of H2S and other sulfur containing compounds such as odorants in the presence of many hydrocarbons. This is important as the sulfur containing compounds adversely impact the fuel cell catalysts and the DMS or GC-DMS can be used to protect the catalysts and shut down the gas supply if the level of sulfur containing compounds gets too high.

In another envisioned embodiment, the GC column, are standard capillary columns, or packed columns, or temperature programmed columns, such as those made by RVM Corporation, Santa Barbra, Calif. The valves injectors may be micromachined or micro fabricated, or nano-fabricated, and the DMS may be micro or nano fabricated or conventionally machined.

In another embodiment the GC column is a multi-capillary GC column coupled to a single or a multitude of DMS or IMS instruments.

BRIEF DESCRIPTION OF THE DRAWINGS

These and other features and advantages of the invention will be more fully understood by the following illustrative description with reference to the appended drawings, in which like elements are labeled with like reference designations and which may not be to scale.

FIG. 10 illustrates a reactant ion peak and the effect of its interaction with a product ion, resulting in a charge transfer and a decrease in the RIP peak intensity.

FIG. 12A is conceptual diagram of a compact GC-DMS system having a spiral GC column and an array of analyzers that is implemented on a substrate according to an illustrative embodiment of the invention.

FIG. 12B is conceptual diagram of a compact GC-DMS system having a meandering GC column and an array of analyzer that is implement on a substrate according to an illustrative embodiment of the invention.

FIG. 12C is a conceptual diagram of a compact GC-DMS system having a spiral GC column with multiple DMS analyzers at various locations within the GC column according to an illustrative embodiment of the invention.

FIG. 26A is a graph of temperature versus time for a GC operating under isothermal conditions.

FIG. 26B is a graph of intensity versus time for a mixed sample eluted from a GC operating under isothermal conditions.

FIG. 27A is a graph of temperature versus time in a GC column where the temperature is ramped/varied in an increasing and/or decreasing manner.

FIG. 27B is a graph of intensity versus time of a mixed sample eluted from a GC column where the GC column temperature is ramped/varied according to FIG. 27A.

FIG. 28A is a graph of temperature versus time in a GC column where the temperature is ramped and/or stepped over a range of temperatures either in an increasing or decreasing manner.

FIG. 28B is a graph of intensity versus time of a mixed sample eluted from a GC column where the temperature is ramped and/or varied according to FIG. 28A.

FIGS. 37A-C is a schematic diagram showing top, end, and side views respectively of a compact GC-DMS system according to an illustrative embodiment of the invention.

ILLUSTRATIVE DESCRIPTION

The invention, in various embodiments, provides systems, methods and devices for detecting, identifying, measuring and analyzing (collectively "analyzing") constituents in a sample. The samples and constituents may include any material; chemical or biological, organic or inorganic. In particular illustrative embodiments, the invention is directed to a compact gas chromatograph (GC)—differential mobility spectrometer (DMS) combination system, which provides a relatively small, light weight, field-deployable, accurate and fast sample analysis system. In other illustrative embodiments, the invention employs linearization techniques for improving analysis accuracy by compensating for effects of detector saturation.

In another illustrative embodiment of the invention the gas chromatograph is integrated with a DMS and time of flight ion mobility spectrometer. Where the DMS and IMS are configured in series so that ions formed in the DMS are then injected into the IMS. In another embodiment, the GC is coupled to a DMS which is configured in parallel with an IMS. The DMS and IMS may or may not have the same ionization source. That is, the effluent from the GC could be split to go into a DMS and an IMS in parallel or simply to go into a single ionization region which serves both the DMS and IMS.

In yet another embodiment, the GC is coupled to a DMS which is configured to a mass spectrometer such that the effluent from the GC passes through the DMS where atmospheric pressure (or near atmospheric pressure) ionization occurs, ions are then affected by the DMS and then injected into the MS. The DMS enables particular control of the ion chemistry during the ionization process and selective ion filtering which preferentially controls the types of ions formed that are introduced into the mass spectrometer. In other embodiments, the GC is coupled to a DMS and IMS configured in series and then attached to a mass spectrometer. In this case, ions are formed in the ionization region of the DMS, upon exiting from the GC, and then selected ions are introduced into the ion mobility spectrometer (where ion separation is based on low field strength ion mobility) and then select ions are introduced into the mass spectrometer. All these steps are designed to provided higher levels of chemical analysis, molecular structure elucidation, better detection of the ion identities and more.

Figure 1:
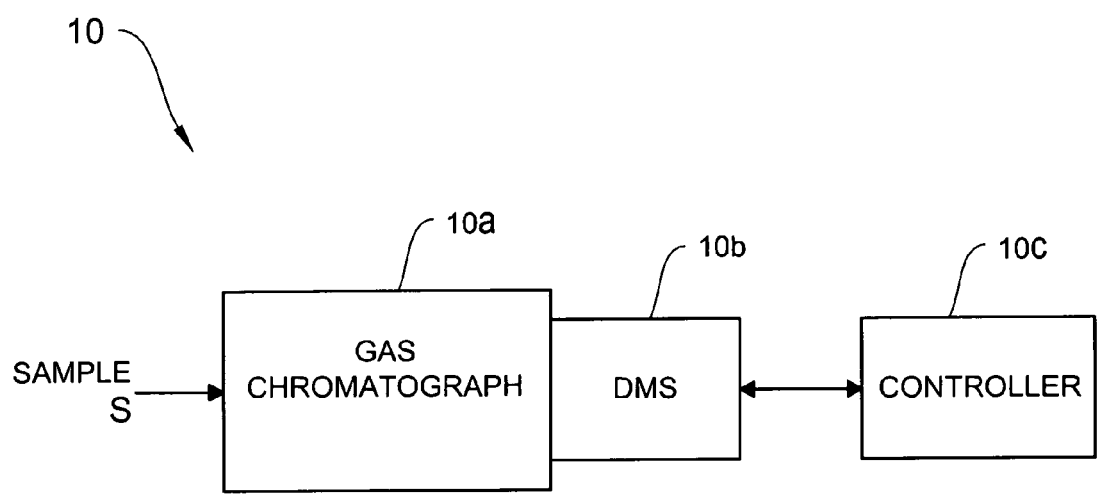
FIG. 1 is a block diagram of a GC-DMS system according to an illustrative embodiment of the invention.

FIG. 1 shows a conceptual block diagram for a compact GC-DMS system 10 according to an illustrative embodiment of the invention. According to the illustrative embodiment, the GC 10a provides pre-separation of sample constituents prior to presenting them to the DMS 10b where the eluted constituents are temporally separated from each other, e.g., the constituents exit the GC 10a at different predictable times.

A data processing system 10c controls operation of the GC 10a and the DMS 10b and processes detector signals from the DMS 10b.

Figure 2A:
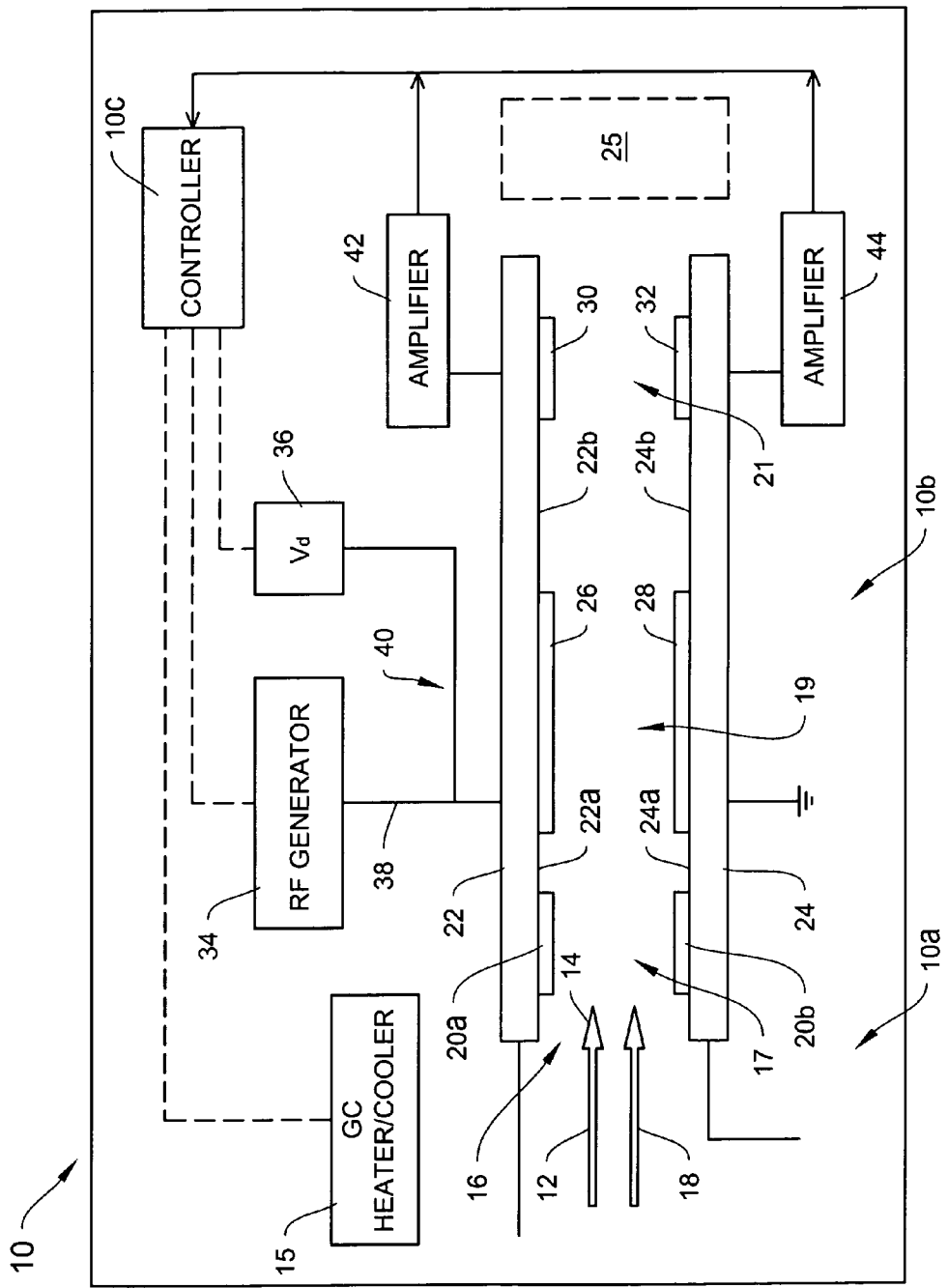
FIG. 2A is a more detailed conceptual diagram of a GC-DMS according to an illustrative embodiment of the invention.

FIG. 2A shows a more detailed conceptual diagram of the compact GC-DMS system 10 of FIG. 1, however, with only a portion of the GC 10a shown. The portion of the GC 10a shown includes a capillary GC column 12. The GC column 12 delivers a sample 14 (via a carrier gas CG) from the GC 10a into the inlet 16 of a DMS flow channel formed between the substrates 22 and 24.

Coupling of the GC 10a with the DMS 10b is non-trivial. One significant hurdle that must be overcome is that a sufficient sample flow rate must be provided to the DMS 10b. More particularly, for appropriate function of the filter region 19 of the DMS 10b, the sample ions need to travel at or near a certain velocity (e.g., around 6 meters per second for an ion filter 15 millimeters long). The sample flow velocity determines the ion velocity through the filter region 19. The average velocity of the sample flow in the ion filter region 19 can be defined as $V=Q/A$, where Q is the sample volume flow rate and A is the cross-sectional area of the flow channel. In one example, the DMS flow channel has a cross-sectional area of about $A=5\times10E-6$ $m^2$. Therefore, a flow rate Q=2 liters per minute of gas is required to produce roughly 6 meters per second average velocity for the sample ions through the filter region 19. If the sample ion velocity is much less than about V=6 meters per second for this device, few, if any, ions will make it through the filter region 19. Instead, they will all be deflected onto the ion filter electrodes 26 and 28 and be neutralized.

A typical flow rate of the sample 14 eluting from the GC column 12 is in the milliliters per minute range, as opposed to the about 200 milliliters (ml) to 2 liters per minute flow rate required by the DMS 10b of this illustrative embodiment. Thus, according to the illustrative embodiment, a drift gas 18 (which may be heated) is introduced into the inlet 16 with the sample 12 to augment the eluent flow from the GC column 12. The invention controls the volume and flow rate of the drift gas 18 to boost the flow rate from the GC column 12 to an optimum rate for the DMS 10b, given any particular flow channel dimensions. The flow rate of the drift gas 18 is also controlled to ensure reproducible retention times within the DMS 10b and to reduce DMS detector drift and noise. It should be noted that although the term "drift gas" is used throughout, any suitable drift effluent may be employed, for example, any suitable liquid, vapor, gas or other fluid.

According to another feature of the invention, the flow rate of the carrier gas CG in the GC column 12 may also be controlled. More specifically, by controlling the flow rate of the CG in the GC column 12 (or the ratio of CG to sample) relative to the volume flow rate of the drift gas 18, various dilution schemes can be realized which increase the dynamic range of the DMS 10b detector (see e.g., FIG. 2B). For example, if the DMS 10b is to detect high concentrations of a sample, it is desirable to dilute the amount of the sample in a known manner so that the DMS 10b can do the detection in its optimal sensitivity range.

In one illustrative embodiment, the flow channel includes an ionization region 17, a filter region 19, and a detector region 21. The ionization region 17 includes an ionization source, provided by corona discharge electrodes 20a and 20b (collectively ionization source 20) in this illustrative embodiment, for ionizing the sample 14. In other illustrative embodiments, the ionization source may be, for example, a radioactive, capacitive discharge, corona discharge, ultraviolet, laser, LED, or other suitable ionization source. The filter region 19 includes two parallel filter electrodes 26 and 28, mounted on the substrates 22 and 24, respectively. The filter electrodes 26 and 28 are excited by an RF waveform 38 provided by the RF generator 34 and a dc compensation voltage 40 provided by the dc source 36. The controller 10c controls both the RF generator 34 and the dc source 36 to provide particular filter field conditions selected for passing particular sample ions. The detector region 21 includes two detector electrodes 30 and 32, also mounted on the substrates 22 and 24, respectively. The detector electrodes 30 and 32 detect sample ions that pass through the filter region 19. The amplifiers 42 and 44 preprocess signals indicative of ion abundance/intensity from the detector electrodes and provide them to the controller 10c for further processing and analysis.

As described briefly above, the sample 14 and the drift gas 18 combine and enter the ionization region 17, and are ionized by the ionization source 20. The ionized sample 14 and drift gas 18 then pass into the filter region 19. As the sample ions pass through filter region 19, some are neutralized as they collide with the filter electrodes 28 and 28, while others pass to detector region 21. The controller 10c regulates the signals 38 and 40 applied to the filter electrodes 26 and 28. The filter electrodes 26 and 28 pass particular sample ions through the ion filter region 19 according to the applied control signals 38 and 40. The path taken by a particular ion is a function of its species characteristic, under influence of the RF filter field controlled by the applied electric signals 38 and 40. According to the illustrative embodiment, the controller 10c, by sweeping the dc compensation voltage (Vcomp) 41 over a predetermined voltage range, obtains a complete intensity spectrum for the sample 14. As described in more detail in the above incorporated patents and patent applications, in some illustrative embodiments, the controller 10c may also or alternatively vary the frequency, duty cycle and/or magnitude of the ac waveform 38 to select which sample ion species are passed through the filter region 19.

In a preferred embodiment, the ion filter electrodes 26 and 28 are formed on the opposed insulating surfaces 22a and 24a, respectively, of the substrates 22 and 24. According to one benefit of this configuration, forming the electrodes 26 and 28 on the insulating surfaces 22a and 24a improves detection sensitivity. More particularly, the substrate regions 22b and 24b provide electrical and spatial insulation/isolation between the filter electrodes 26 and 28 and the detector electrodes 30 and 32, effectively isolating the applied asymmetric periodic voltage (Vrf) 38 from the detector electrodes 30 and 32. The substrate regions 22b and 24b also spatially separates the filter's field from the detector electrodes 30 and 32. Such spatial and electrical isolation reduces noise at the filter electrodes 30 and 32 and increases the sensitivity of sample ion detection. Using the illustrative techniques of the invention, detector sensitivity of parts per billion and parts per trillion may be achieved.

According to another benefit, forming the filter 26 and 28 and detector 30 and 32 electrodes on an insulative substrate enables the filter electrodes 26 and 28 to be positioned closer to the detector electrodes 30 and 32, without increasing noise problems. According to another benefit, this distance reduction reduces the time it takes to make a detection, enhances ion collection efficiency and favorably reduces the system mass that needs to be regulated, heated and/or controlled. According to a further benefit, reducing the distance between electrodes also shortens the flow path and reduces power requirements. Furthermore, use of small electrodes reduces capacitance, which also reduces power consumption. Additionally, depositing the spaced electrodes on a common substrate lends itself to a mass production process, since the insulating surfaces of the substrates provide a suitable platform for forming such electrodes. One or more substrates may be combined and/or integrated into an integrated circuit and/or chip.

The sample ions that make it through the filter region 19 without being neutralized then flow to the detector region 21. In the detector region 21, either electrode 30 or 32 may detect ions depending on the ion charge and the voltage applied to the electrodes. For example, a positive bias voltage may be applied to one of the detector electrodes and a negative bias voltage may be applied to the other detector electrode. In this way, both negative and positive mode ions may be detected concurrently or substantially simultaneously; negative at one detector electrode and positive at the other detector electrode. The amplifier 42 preprocesses the signal from the detector 30 and provides it to the controller 10c, while the amplifier 44 preprocesses the signal from the detector 32 and provides it to the controller 10c. Thus, the compact GC-DMS of the invention can make multiple substantially simultaneous detections of different ion species, further speeding up the response time.

In one illustrative embodiment, the insulated substrates 22 and 24 are formed, for example, from insulating materials such as Pyrex™ glass, plastics and polymers, e.g., Teflon™, printed circuit boards, e.g., FR4, or other suitable materials. According to a further illustrative embodiment, the filter 26 and 28 and/or detector 30 and 32 electrodes are formed, for example, from gold, platinum, silver or other suitably conductive material.

Optionally, the compact GC-DMS 10 includes a pump 25 for flow generation, air recirculation and/or maintenance in the flow channel. The pump 25 may be, for example, a solid state flow generator such as that disclosed in U.S. application Ser. No. 10/943,523, filed on 17 Sep. 2004, and entitled "Solid-State Flow Generator and Related Systems, Applications, and Methods." Longitudinal electric fields, like those described in U.S. Pat. No. 6,512,224, entitled "Longitudinal Field Driven Asymmetric Ion Mobility Filter and Detection System," can also be used and, thereby, eliminate the need for a drift gas in the DMS entirely or partially. Both of these applications are incorporated by reference above. The compact GC-DMS 10 may further include a GC heater/cooler element 15 that is responsive to the controller 10C and capable of varying the temperature of at least a portion of the column 12.

Figure 2B:
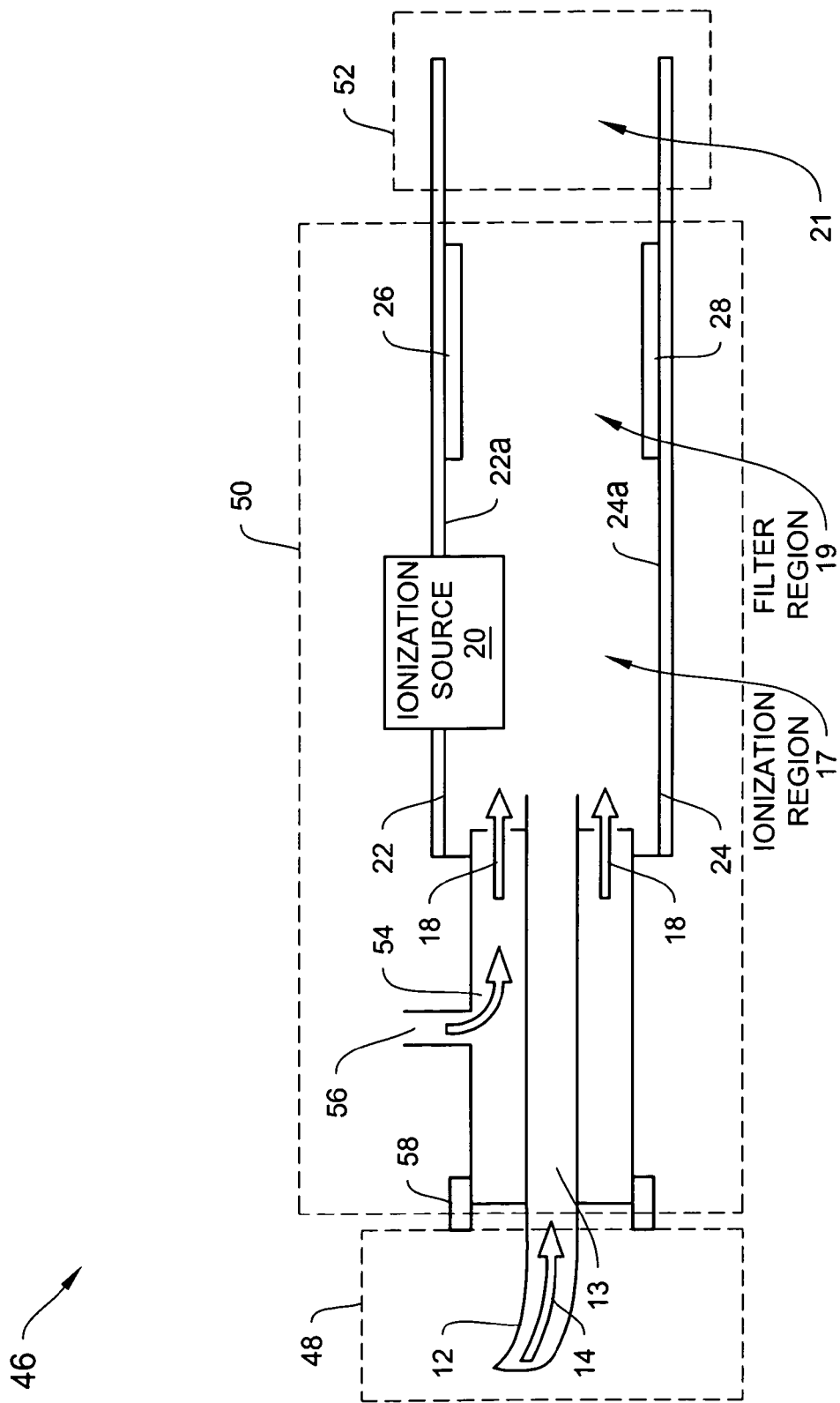
FIG. 2B is a conceptual diagram of a compact GC-DMS having an ionization source located between the GC and the field electrodes of the DMS according to an illustrative embodiment of the invention.

FIG. 2B is a conceptual diagram of a compact GC-DMS system 46 according to an alternative illustrative embodiment of the invention. As shown, the system 46 includes a compact GC 48, a compact DMS 50, and an external detector 52. As in the case of the illustrative embodiment of FIG. 2A, the GC 48 includes a GC column 12. The GC column 12 couples to a sample flow conduit 13 via a T-connector 58, which attaches or screws into both the GC outlet and the DMS inlet housing, and allows the GC column 12 to be either passed through the DMS inlet housing or to fluidly couple to the sample flow conduit 13 to deliver the CG and sample into the ionization region 17. The T-connector 58 also serves to mechanically protect the GC column 12.

In this illustrative embodiment, the sample flow conduit 13 is surrounded by a conduit 54. A drift gas 18 flows into the conduit 54 by way of a port 56. As in the case of the system 10 of FIG. 1, the volume and flow rate of the drift gas 18 is controlled to augment the flow of the carrier gas (CG) from the GC column 12 to provide an optimum flow through the filter region 19 of the DMS 50.

As in the case of the DMS 10b, the sample 14 is ionized in the ionization region 17 by the ionization source 20. The ionized sample 14 then flows into the filter region 19. The filter electrodes 26 and 28 are formed on the surfaces 22a and 24a, respectively, of the substrates 22 and 24. Vrf and Vcomp control signals, such as the signals 38 and 40, respectively, are applied to the filter electrodes 26 and/or 28 to regulate which particular ion species pass through the filter region 19.

As in the case of the DMS 10b, the ionization region 17, the filter region 19 and the detector region 21 form the flow channel (also referred to as the drift tube) through which the sample flows during analysis. According to this illustrative embodiment, the ionization source 20 may be located remotely from the flow channel of the DMS 50, partially within the flow channel, or completely within the flow channel. Additionally, the substrates 22 or 24 may include an aperture in the ionization region 17 through which the sample 14 may interact with the ion source 20.

Also, although the flow channel is discussed as being defined by the substrates 22 and 24, it should be noted that the flow channel is, preferably enclosed. Thus, viewed from a mechanical standpoint, the drawings of FIGS. 2A and 2B should be understood as providing a cross-sectional view of the flow channel. Further, while the substrates 22 and 24 may be opposed planar substrates, they may also be opposite sides of a single cylindrical substrate. In replacement for the detector electrodes 30 and 32 of the system 10 of FIG. 2A, the system 46 includes a detector 52, which may be packaged with or separately from the GC-DMS combination 48 and 50. According to one embodiment, the detector 52 includes a mass spectrometer or other detector, which may be directly coupled to the output of the filter region 19.

Figure 2C:
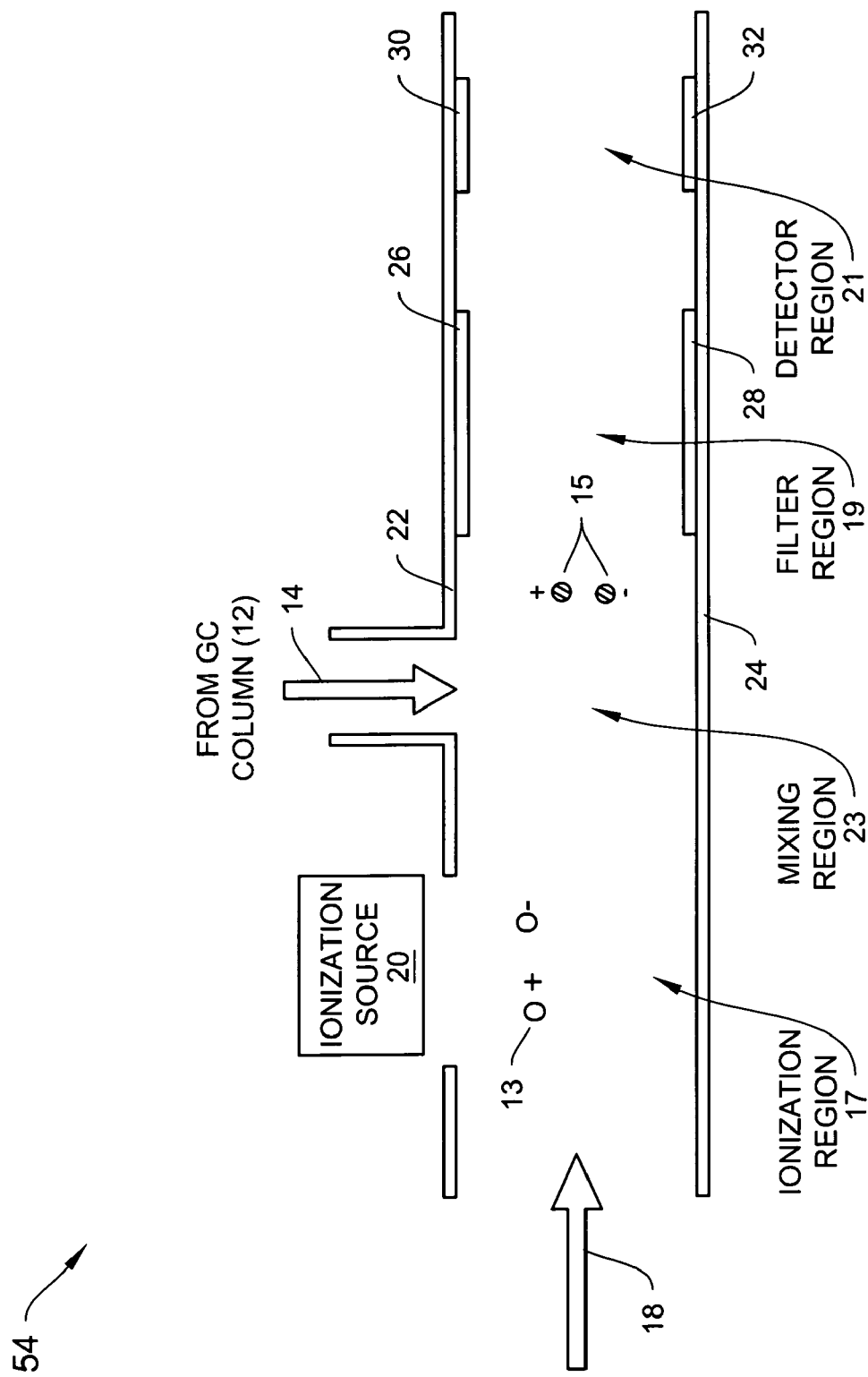
FIG. 2C is a conceptual diagram of a compact GC-DMS which avoids exposing the GC sample directly to an ionization source, by locating the ionization source prior to the outlet of the GC column so that the DMS drift gas or constituents of the drift gas, e.g., dopants, are ionized and then mix and interact with the sample molecules

FIG. 2C is a conceptual diagram of a compact GC-DMS 54 according to another illustrative embodiment of the invention. In this illustrative embodiment, rather than exposing the sample 14 to the ionization source 20, the drift gas 18, dopant or additive constituents in the drift gas are exposed to and ionized by the ionization source 20 in the ionization region 17. The sample 14 from the GC column 12 enters the flow channel in a mixing region 23. The reactant ions 13 from the ionized drift gas 18 or its constituents mix with the sample 14 in the mixing region 23 to create product ions 15. One advantage of this design is that the ionization source 20 is not exposed to the sample molecules 14 and cannot react with them, as some chemicals introduced by the GC column 12 may attack the ionization source 20 and damage it. Using this design, many additional chemicals which ordinarily cannot be used with a particular ionization source 20 can be used. The product ions 15 are then flowed through the filter region 19. The components of the filter region 19 and the detector region 21 are substantially identical and operate in the same fashion as those described above with regard to FIG. 2A. An important feature of the above described illustrative embodiments is that they enable a light weight, relatively compact, and relatively fast, e.g., millisecond to second, sample analysis by a DMS. As such, it is uniquely suited for field deployment. One way that the invention achieves the above features is by reducing analyzer flow channel or path dead volume and DMS scanning rates. Dead volume is any region in a flow channel or path where there is no flow or low flow.

According to an illustrative embodiment, the invention reduces dead volume, size and weight by providing substrates, such as the substrates 22 and 24, that have multiple functional uses. For example, the substrates 22 and 24 provide platforms (or a physical support structures) for the precise definition and location of the component parts or sections of the compact GC-DMS device of the invention. The substrates, such as the substrates 22 and 24, form a housing enclosing the flow channel with the filter region 19 and perhaps the ionization region 17 and/or the detector region 21, as well as other components, enclosed. This multi-functional substrate design reduces parts count while also precisely locating the component parts so that quality and consistency in volume manufacture can be achieved. A description of an exemplary compact or micro-GC system, which may be employed with the invention, is provided by Lu et al. in *Functionally Integrated MEMS Micro Gas Chromatograph Subsystem*, 7$^{th}$ International Conference on Miniaturized Chemical and Biochemical Analysis Systems, October 2003, Squaw Valley, Calif., USA.

As mentioned above, the compact GC-DMS of the invention also has unexpected performance improvements, due for example, to the shorter drift tube/flow channel, and the electrical insulation and spatial isolation provided by portions of the substrates 22 and 24. Also, because they are insulating or an insulator (e.g., glass or ceramic), the substrates 22 and 24 provide a platform for direct formation of components, such as electrodes, with improved performance characteristics.

It is should be noted that use of the substrates 22 and 24 as a support/housing does not preclude yet other "housing" parts or other structures to be built around a compact GC-DMS of the invention. For example, it may be desirable to put a humidity barrier over the device. As well, additional components, such as batteries, can be mounted to the outside of the substrate/housing, e.g., in a battery enclosure. Nevertheless, embodiments of the compact GC-DMS of invention distinguish over the prior art by virtue of performance and unique structure generally, and the substrate insulation function, support function, multi-functional housing functions, specifically, as well as other novel features.

According to various illustrative embodiments, a compact DMS analyzer, such as the DMS 10b of FIG. 1, has decreased size and power requirements while achieving parts-per-trillion sensitivity. According to one illustrative embodiment, the compact DMS 10b can have a less than about 5 Watt (W) and even less than about 0.25 mW overall power dissipation, and a size of about a 2-cm$^3$ or less, not including a power source or display, but including an RF field generator. According to some embodiments, the compact DMS 10b of the invention has a total power dissipation of less than about 15 W, about 10 W, about 5 W, about 2.5 W, about 1 W, about 500 mW, about 100 mW, about 50 mW, about 10 mW, about 5 mW, about 2.5 mW, about 1 mW, and/or about 0.5 mW. According to further embodiments, an analyzer system employing a flow generator, such as a MEMS pump, compress fluid source or a solid-state flow generator as is described in U.S. patent application Ser. No. 10/943,523, filed on Sep. 17, 2004 (incorporated by reference above), optionally including a display (e.g., indicator lights and/or an alphanumeric display) and a power source (e.g., a rechargeable battery) compartment, along with an RF field generator, may have a total package outer dimension of less than about 0.016 m$^3$, 0.0125 m$^3$, 0.01 m$^3$, 0.0056 m$^3$, 0.005 m$^3$, 0.002 m$^3$, 0.00175 m$^3$, 0.0015 m$^3$, 0.00125 m$^3$, 0.001 m$^3$, 750 cm$^3$, 625 cm$^3$, 500 cm$^3$, 250 cm$^3$, 100 cm$^3$, 50 cm$^3$, 25 cm$^3$, 10 cm$^3$, 5 cm3, 2.5 cm$^3$, with the package being made, for example, from a high impact plastic, a carbon fiber, or a metal. According to further illustrative embodiments, the DMS 10b, for example, including an RF generator, and optionally including a display, keypad, and power source compartment, may have a total package weight of less than about 5 lbs, 3 lbs, 1.75 lbs, 1 lbs, or 0.5 lbs.

In one practice of the invention, the small size and unique design of the DMS 10b enables use of short filter electrodes that minimize the travel time of the ions in the ion filter region and therefore minimize the detection time. The average ion travel time td from the ionization region to the detector is determined by the drift gas velocity V and the length of the ion filter region Lf, and is given by the relation td=Lf/V. Because Lf can be made small (e.g., 15 mm or less) in the illustrative DMS, and the RF asymmetric fields can have frequencies of about 5 MHz, the response time of the DMS can be very short (e.g., one millisecond or less), while the ion filtering (discrimination) can still be very effective.

Table 1 provides a comparison of drift tube (e.g., the constrained channel) dimensions, fundamental carrier gas velocities, and ion velocities for a various illustrative embodiments of a compact DMS analyzer lob, depending on the flow rate (Q) available to the analysis unit. Designs 1-4 provide flow rates of varying orders of magnitude ranging from about 0.03 l/m to about 3.0 l/m. Table 1 illustrates that as the flow rate is decreased through the compact DMS b 10b, the filter plate dimensions and power requirements are reduced. Table 1 is applicable to a DMS 10b using either a sample gas or longitudinal field-induced ion motion. The time to remove an unwanted analyte is preferably less than about the time for the carrier gas CG to flow through the filter region (tratio). Also, for a particular target agent, the lateral diffusion as the ion flows through a DMS 10b is preferably less than about half the filter electrode spacing (difratio). Based on this criteria, the filter electrode dimensions may be reduced to about 3×1 mm$^2$ or smaller, while the ideal flow power may be reduced to less than about 0.1 mW. Thus, even for design 4, the number of analyte ions striking the detectors is sufficient to satisfy a parts-per-trillion detection requirement.

under (less than) 10 seconds, under one second, under 100 milliseconds, under 10 milliseconds, under 1 millisecond.

Ion clustering can also be affected by varying the electric field strength. By applying fields with larger amplitudes or at higher frequencies, the amount of clustering of the ions can be reduced, representing yet another mechanism of enhanced compound discrimination.

According to one illustrative embodiment of the invention, a GC-DMS system 10 was formed as follows: A model 5710 gas chromatograph (Hewlett-Packard Co., Avondale Pa.) was equipped with a HP splitless injector, 30 m SP 2300 capillary column (Supelco, Bellefonte, Pa.), (columns as short as 1 m have also been used) and a DMS detector. Air was provided to the GC drift tube at 1 to 2 liters/minute (L/m) and was provided from a model 737 Addco Pure Air generator (Addco, Inc., Miami, Fla.) and further purified over a 5 Å molecular sieve bed (5 cm diameter×2 m long). The drift tube was placed on one side of an aluminum box, which also included the DMS electronics package. A 10 cm section of capillary column was passed through a heated tube to the DMS. The carrier gas was nitrogen (99.99%) scrubbed over a molecular sieve bed which could be 10× or additionally a charcoal filter to remove volatiles, or a catalyst which reacts with the gas to catalyze the gas impurities, although it could also be air or helium or hydrogen. Pressure on the splitless injector was 10 psig and the split ratio was 200:1.

TABLE 1

Illustrative DMS Analyzer System Design Specifications and Characteristics

| Description | Units | Symbol | Design 1 Q = 3 l/m Baseline | Design 2 Q = 0.3 l/m Base dimen | Design 3 Q = 0.3 l/m scaled | Design 4 Q = 0.03 l/m |
|---|---|---|---|---|---|---|
| plate dimensions | | | | | | |
| *length | m | L | 0.025 | 0.025 | 0.005 | 0.001 |
| *width | m | b | 0.002 | 0.002 | 0.001 | 0.0004 |
| *air gap | m | h | 0.0005 | 0.0005 | 0.0005 | 0.0002 |
| *volume flow rate | l/min | Qf | 3 | 0.3 | 0.3 | 0.03 |
| Flow velocity | m/s | Vf | 50 | 5 | 10 | 6.25 |
| pressure drop | Pa | dPf | 1080 | 108 | 43.2 | 33.75 |
| flow power | W | Powf | 0.054 | 0.00054 | 2.16E−04 | 1.69E.05 |
| RF excitation | V | Vrf | 650 | 650 | 650 | 260 |
| design ratios | | | | | | |
| Time to remove unwanted analyte divided by carrier time | s | tratio | 0.0128 | 0.0013 | 0.0128 | 0.0160 |
| wanted ions-lateral diffusion divided by half gap | s | difratio | 0.200 | 0.632 | 0.200 | 0.283 |
| ions to count per cycle | — | Nout | 1.22E+07 | 1.22E+06 | 1.22E+06 | 1.22E+05 |

The short length of the DMS spectrometer section 10b and small ionization volume mean that the GC-DMS of the invention provides the ability to study the kinetics of ion formation. If the ions are transported very rapidly through the DMS section, the monomer ions are more likely to be detected since there is less time for clustering and other ion-molecule interactions to occur. By reducing the ion residence time in the DMS section, the ions have less opportunity to interact with other neutral sample molecules to form dimmers (an ion with a neutral attached) or unwanted clusters. The small size of the GC-DMS of the invention, according to one feature, enables ion residence times of about or less than 1 ms, less than about 500 micro seconds, less than about 10 micro seconds, less than about 1 microsecond. Thus, a total spectra (e.g., sweeping Vcomp over a range of about 100 volts) can be obtained in The Vcomp was scanned from about +/−100 Vdc. The asymmetric waveform had a high voltage of about 1.0 kV (20 kV cm-1) and a low voltage of about −500 V (−5 kV cm-1). The frequency was about 1 MHz and the high frequency had about a 20% duty cycle, although the system has been operated with frequencies up to about 5 MHz. The amplifier was based upon a Analog Devices model 459 amplifier and exhibited linear response time and bandwidth of about 7 ms and about 140 Hz, respectively. The signals from the detectors were processed using a National Instruments board (model 6024E) to digitize and store the scans and specialized software to display the results as spectra, topographic plots and graphs of ion intensity versus time. The ion source was a small 63Ni foil with total activity of about 2 mCi. However, a substantial amount of ion flux from the foil was lost by the geometry of the ionization region and the estimated effective activity was about 0.6 to 1 mCi.

Figure 3A:
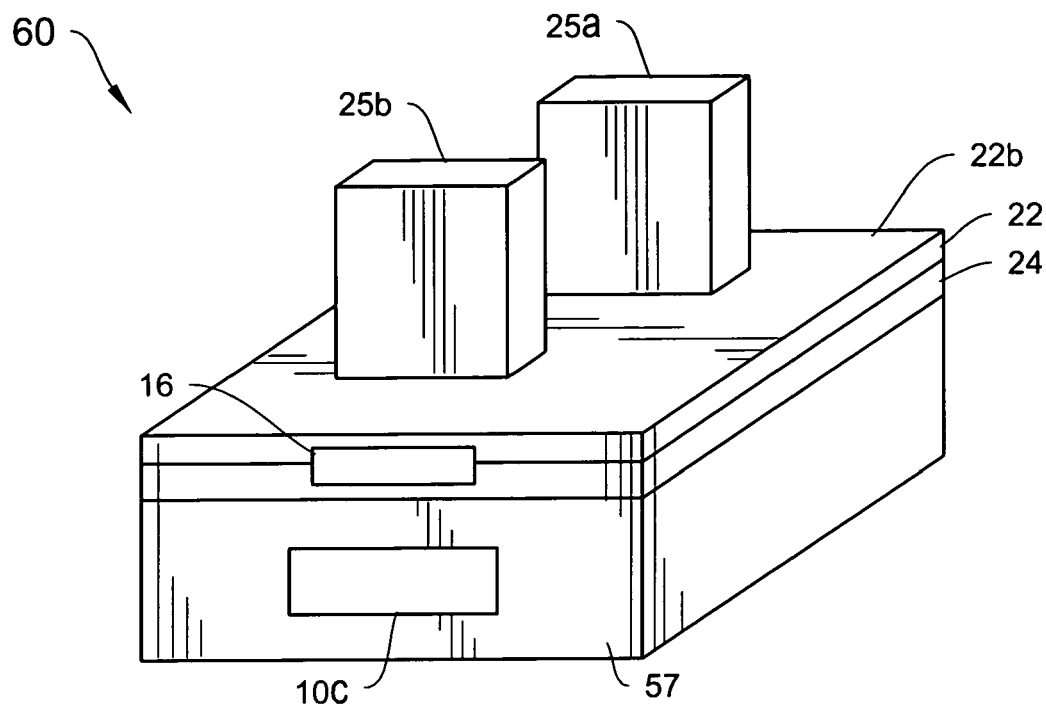
FIG. 3A is a perspective view of a mechanical layout for a compact DMS of a compact GC-DMS system according to an illustrative embodiment of the invention.

FIG. 3A is a front perspective view of a compact DMS 60 including the DMS 10b and the controller 10c of FIG. 2A, packaged according to an illustrative embodiment of the invention, and configured for interoperative coupling to the GC 10a via inlet port 16. As conceptually depicted, the processing section 10c, in this embodiment, including other accompanying electronic circuitry, such as the amplifiers 30 and 32 are located in a lower housing portion 56. The substrates 22 and 24 are located adjacent to each other to define the flow channel for the DMS 10b, with the substrate 24 providing both spatial isolation and electrical insulation between the lower housing 57 (containing the processor 10c) and the flow channel including the filter electrodes 26 and 28. A back side 22b of the substrate 22 provides a structural outer cover for the compact GC-DMS 10. The structures 25a and 25b are portions of the flow pump 25, described above with regard to FIG. 2A. In this embodiment, 25a provides flow through the flow channel, while 25b may provide recirculation of conditioned air or another effluent. An inlet port 16 provides an interface for coupling to the GC 10a, for example, by way of a T-connector, such as the T-connector 58 of FIG. 2B. According to the illustrative embodiment of FIG. 3A, the compact DMS 60 may be less than or equal to about 1, 2, 3, 4, 6 or 8 cubic inches. According to other illustrative embodiments, it is less than about 16, 20 or 24 cubic inches.

Figure 3B:
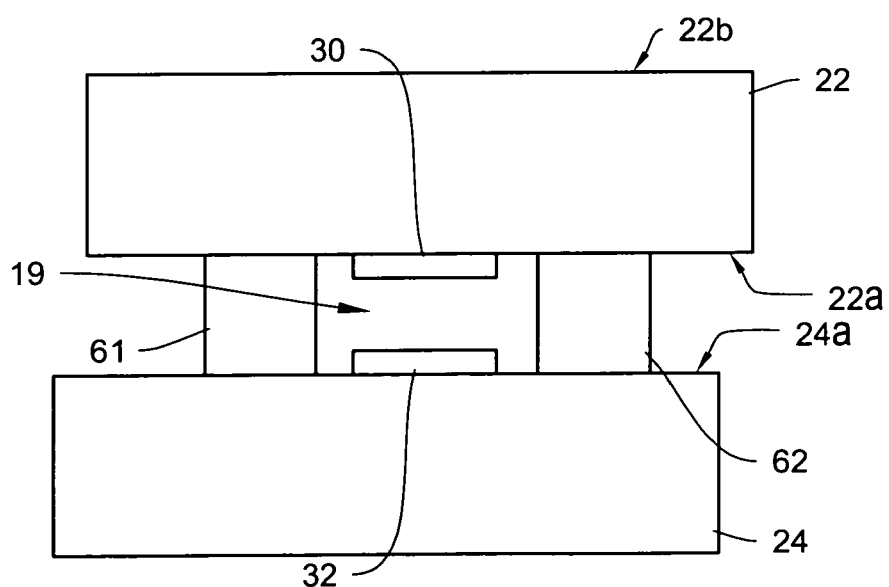
FIG. 3B is a side cross-sectional view of the compact DMS which forms part of the system of FIG. 3A, and shows the spacers and spaced substrates.

FIG. 3B shows front cross-sectional mechanical view, illustrating one way in which the substrates 22 and 24 of FIG. 3A may be spaced apart to ensure suitable spacing between the electrodes 30 and 32. As shown, the spacers 61 and 62 are located between the surfaces 22a and 24a. According to this illustrative embodiment, the thickness of spacers 52a and 52b defines the distance between the substrates and electrodes 22 and 24. Preferably, the spacers 52a and 52b run along the length of the flow channel, or in some instances, the entire length of the substrates 22 and 24 to enclose the flow channel. The spacers 61 and 62 may be electrically insulative or alternatively, may be electrically conductive. According to various illustrative embodiments, the spacers 61 and 62 are formed by etching or dicing silicon wafers, or may be formed from patterned Teflon, ceramic, or other insulator. In one embodiment, the spacers 61 and 62 are used as electrodes and a confining voltage is applied to the spacer electrodes to confine the filtered ions within the center of the flow path. This confinement can result in more ions striking the detectors, and improves detection sensitivity.

Figure 3C:
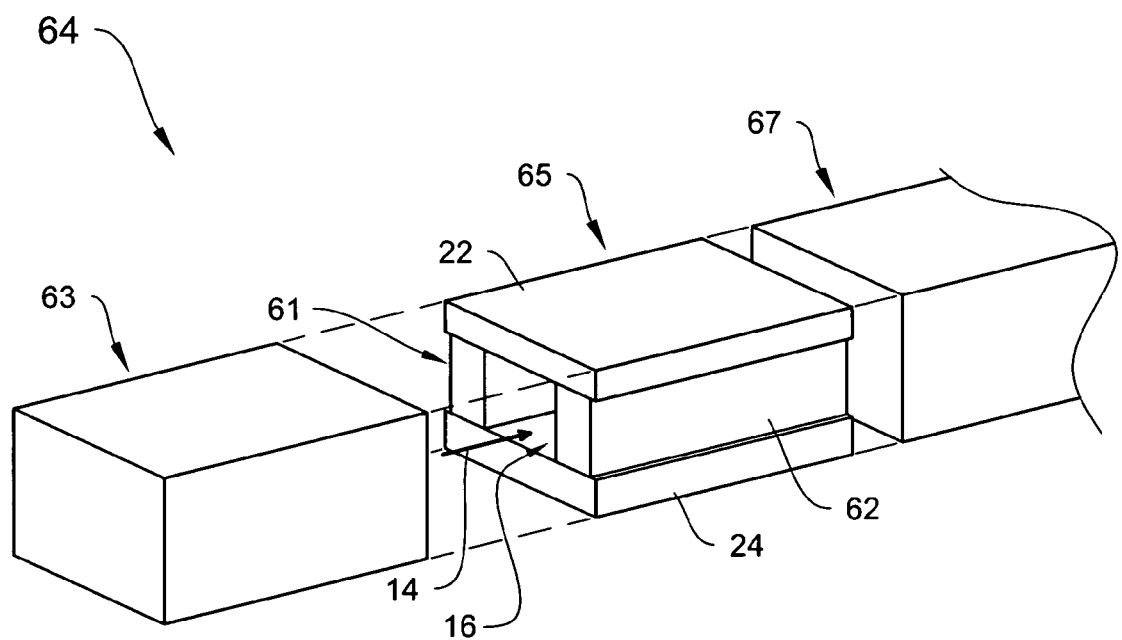
FIG. 3C is an exploded perspective view of a mechanical layout for a compact GC-DMS using insulating spacers according to another illustrative embodiment of the invention.

FIG. 3C is a side perspective exploded view of a compact GC-DMS 64 including the GC 10a, DMS 10b and the controller 10c of FIG. 2A, packaged according to another illustrative embodiment of the invention. As shown, the GC 10a is formed in a housing 63, the ionization 17 and filter 19 regions are packaged in the housing 65, and the detector region is packaged in the housing 67. In this illustrative embodiment, the substrates 22 and 24 form the top and bottom walls of the flow channel, while the spacers 61 and 62 form the side walls of the flow channel. The housing 63, encloses all or a portion of the GC 10a, and mechanically fits with the housing 65 to enable the GC column 12 to flow the sample 14 into the inlet 16 of the DMS 10b.

In operation of the above described DMS 10b, some ions are driven into the electrodes 26 and 28 and neutralized. These ions can be purged by heating. According to one illustrative embodiment, the invention heats the flow path by applying a current to the filter electrodes 26 and 28 or to the spacer electrodes 61 and 62. The spacer electrodes 61 and 62 may also be used to heat the ion filter region 19 to make the DMS 10b more insensitive to external temperature variations.

Although the illustrative embodiments of FIGS. 1-3C are described above with regard to a single pair of filter electrodes 26 and 28 and a single pair of detector electrodes 30 and 32, this need not be the case. By way of example, a compact DMS 10b of the invention may include multiple pairs of filter electrodes arranged in parallel, series or some combination of series and parallel. The filter electrodes may also be arranged in one, two or three dimensional matrices of filter electrodes. Additionally, the compact DMS of the invention may include multiple pairs of detector electrodes, arranged in series, parallel or some combination of both. The detector electrodes may also be segmented, as described below in further detail.

Figure 4:
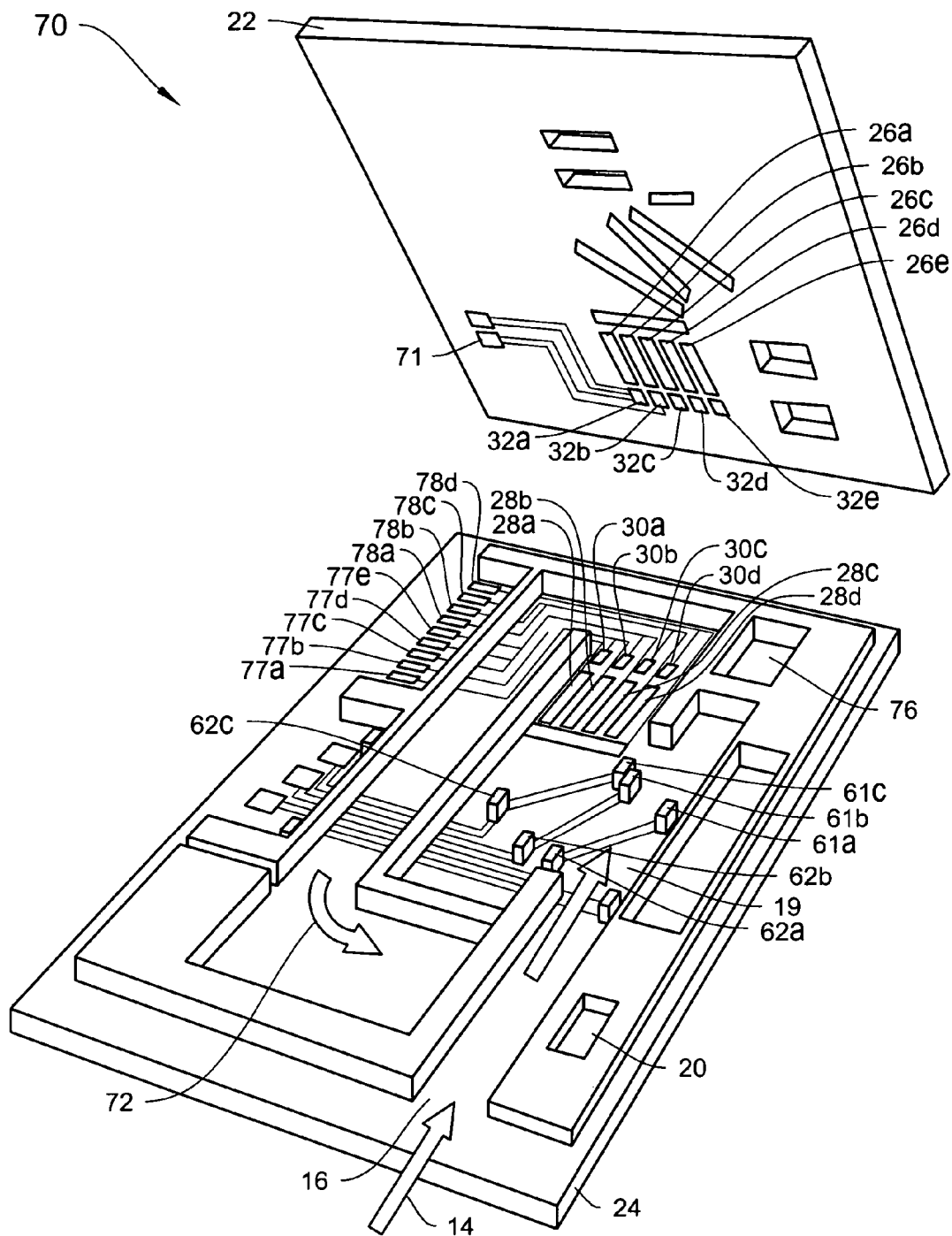
FIG. 4 is schematic views of an electro-mechanical component layout, or integrated circuit like structure, for a compact GC-DMS using an array of filter and detector electrodes in a single flow path according to an illustrative embodiment of the invention.

FIG. 4 is an exploded perspective view of a mechanical layout for a compact DMS 70 according to an illustrative embodiment of the invention and including a plurality of pairs of filter electrodes 26 and 28. Where the same components of FIG. 2A are employed, only in multiples, the multiples are indicated by the appended a, b, c, d, etc. Turning to FIG. 4, the DMS 70 includes a sample inlet 16 for receiving a sample 14, for example, from a GC column 12. The DMS 70 also includes an ionization source 20, such as the corona discharge source of FIG. 1A. The DMS 70 further includes a plurality of pairs of spacers 61a-62a, 61b-62b, 61c-62c, 61d-62d, and 61e-62e (not visible). As discussed above with regard FIGS. 3A-3C, the spacers 61a-61d and 62a-62d may be used to confine a plurality of flow channels, where each channel is associated with a particular filter electrode pair. They may also be electrodes, biased to deflect or otherwise steer or contain ions flowing in the flow channel.

The illustrative DMS 70 also includes a plurality of filter electrode pairs 26a-28a, 26b-26b, 26c-28c, 26d-28d, and 26e-28e. Each of the leads 77a-77e independently provides, for example, the compensation voltage Vcomp to a respective filter electrode pair 26-28. Each of the leads 78a-78e (78e not visible) independently provides, for example, the ac field voltage Vrf to a respective filter electrode pair 26-28. As shown, each filter electrode pair 26a-28a, 26b-26b, 26c-28c, 26d-28d, and 26e-28e has an associated detector electrode pair 30a-32a, 30b-32b, 30c-32c, 30d-32d, and 30d-32e (30e not visible). According to the illustrative embodiment of FIG. 4, and as indicated by the arrow 72, a single flow channel is provided to the filter electrode pairs 26a-28a, 26b-28b, 26c-28c, 26d-28d, and 26e-28e. However, the path between each filter electrode pair and its respective detector pair 30a-32a, 30b-32b, 30c-32c, 30d-32d, and 30d-32e (30e not visible) may be confined According to one illustrative embodiment, the filter electrode pairs 26a-28a, 26b-26b, 26c-28c, 26d-28d, and 26e-28e are caused to concurrently or substantially simultaneously pass different ion species according to the applied signals 77a-77e, 78a-78e, and 71. Thus, the detector pairs 30a-32a, 30b-32b, 30c-32c, 30d-32d, and 30d-32e (30e not visible) can concurrently or substantially simultaneously detect a plurality of ion species.

Alternatively, the control signals 77a-77e, 78a-78e, and 71 may be swept for each pair over a range of Vcomp and/or Vrf conditions to obtain a desired sample spectrum. Although FIG. 4 only shows two applied control signals 71 being connected to filter electrodes 26a-26e, the bias voltages Vcomp and/or Vrf for filter electrodes 26a-26e can be controlled independently by additional applied control signals. According to another feature, with an array of filter electrode pairs 26a-28a, 26b-26b, 26c-28c, 26d-28d, and 26e-28e, a complete spectral range of compensation voltages Vcomp can be more rapidly scanned than with a single filter. In an array configuration, each filter can also be used to scan over a smaller Vcomp and/or Vrf voltage range. The combination of all of these scans results in sweeping the desired full spectrum in a reduced time period. If there are three filters, for example, the spectrum can be divided into three portion and each is assigned to one of the filters, and all three can be measured simultaneously. In practice of the invention, filter array 28-30 may include any number of filter electrodes, depending on the size and use of the DMS 70. According to the illustrative embodiment of FIG. 4, the DMS has a single common exit port 76.

Figure 5:
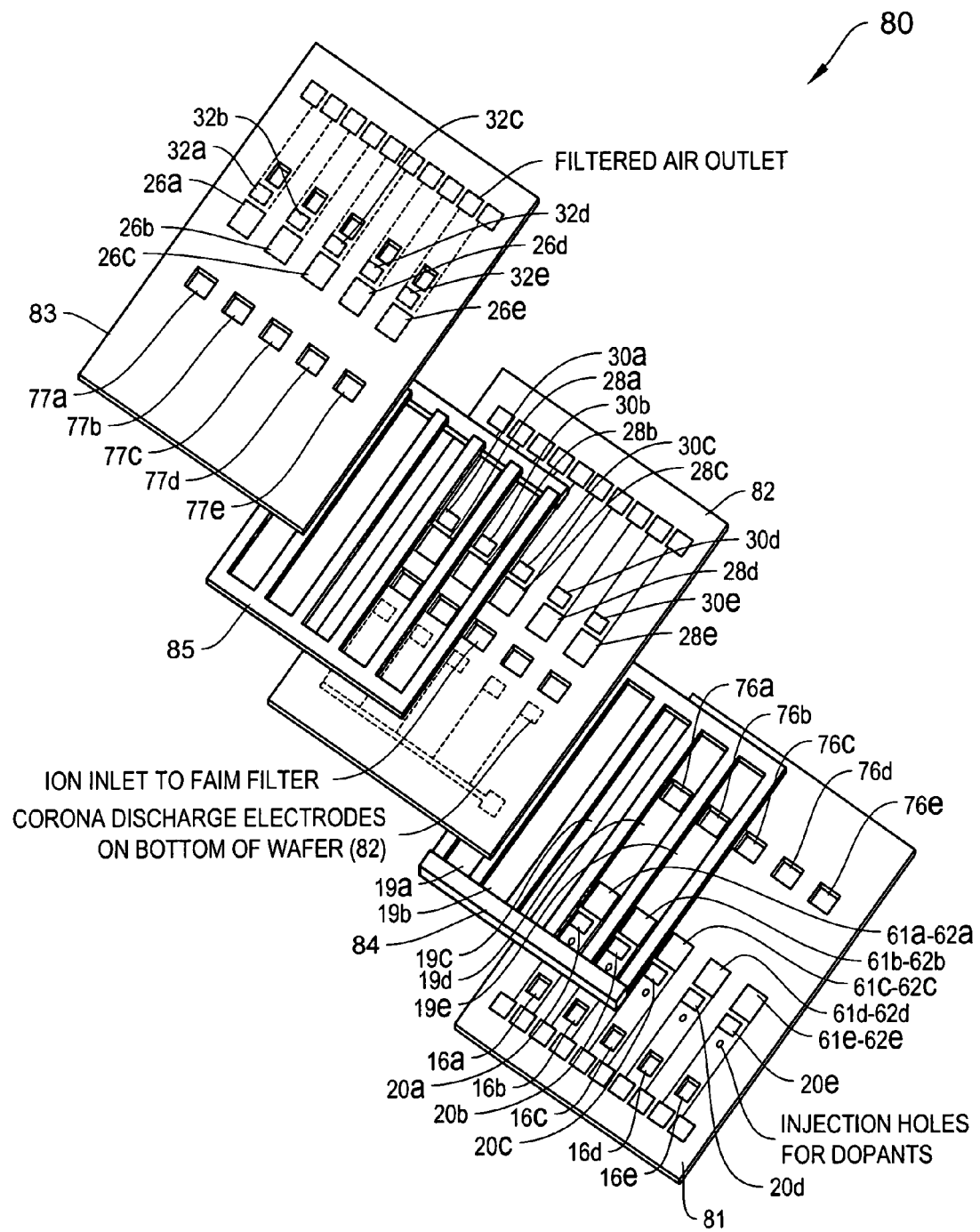
FIG. 5 is an exploded perspective view of an electro-mechanical component layout for a compact analyzer employing array of DMS filters with multiple flow paths according to an illustrative embodiment of the invention.

FIG. 5 is an exploded perspective view of a mechanical layout for a compact DMS 80 according to an illustrative embodiment of the invention and including a plurality of flow channels. In a similar fashion to FIG. 4, where the same components depicted in FIG. 2A are employed, only in multiples, the multiples are indicated by the appended a, b, c, d, etc. As shown, the DMS 80 is formed from multiple substrates, including three Pyrex™ glass substrates 81-83 and two semiconductor, e.g., silicon substrates 84 and 85. The top of the substrate 81 is analogous to the tope side 24a of the substrate 24 of FIG. 2A. The bottom of the substrate 82 operates in an analogous fashion to bottom side 22a of the substrate 22 in FIG. 2A. The top of the substrate 82 operates in an analogous fashion to the top side 24a of the substrate 24 of FIG. 2A, and the bottom of the substrate 83 operates in an analogous fashion to the bottom side 22a of the substrate 22 of FIG. 2A. The substrate 84 provides the necessary spacing between the substrates 81 and 82, while the substrate 85 provides the necessary spacing between the substrates 82 and 83.

The multilayer design of the DMS 80 provides a plurality of flow channel inlets 16a-16e, each having a corresponding outlet 76a-76e. Each flow channel includes a corona discharge electrode 20-20e, respectively, for ionizing a sample. Each flow channel also includes a pair of confinement electrodes 61a-62a, 61b-62b, 61c-62c, 61d-62d, and 61e-62e for directing the flow of sample ions along a respective flow path. Each flow channel further includes an inlet 77a-77e for filtered air or other suitable gas.

The DMS 80 also includes a plurality of dopant injection holes. The dopant injection holes enable any of a plurality of volatile or volatilized compounds, vapors, or gasses to be controllably added to the drift gas. By injecting one or more volatile compounds (e.g., dopants or molecular modifiers) into the flow channel, the spectral characteristics of a sample species can be changed in a predictable and unique manner. Such predictable changes enable enhanced detector discrimination between species having otherwise similar or substantially identical spectral characteristics. According to some illustrative embodiments, different dopants or combinations of dopants may be injected into different flow channels. The result is that the ion filter and detector pairs can each be specialized for analyzing a selected species. Dopants, such as, methylene bromide ($CH_2Br_2$), methylene chloride ($CH_2Cl_2$), chloroform ($CHCl_3$), water ($H_2O$), methanol ($CH_3OH$), and isopropanol, may be introduced, mixed and/or flowed with a sample. The concentrations of these dopants can be less than 1 part per trillion to more than 10%.

Use of arrays is important when there is a desire to measure perhaps a dozen or so compounds in a very brief amount of time. If a fast GC is used as the front end to a compact DMS, such as the DMS 80, the widths of the chemical peaks eluting from the GC can be as brief as a few seconds. To obtain a complete spectral sweep over the required compensation voltage range in time to capture the information contained in the GC, the spectral range can be subdivided amongst each of the filter electrode pairs 26a-28a, 26b-26b, 26c-28c, 26d-28d, and 26e-28e in the array. This allows a concurrent or substantially simultaneous detection of all the constituents in the given GC peak.

Figure 6:
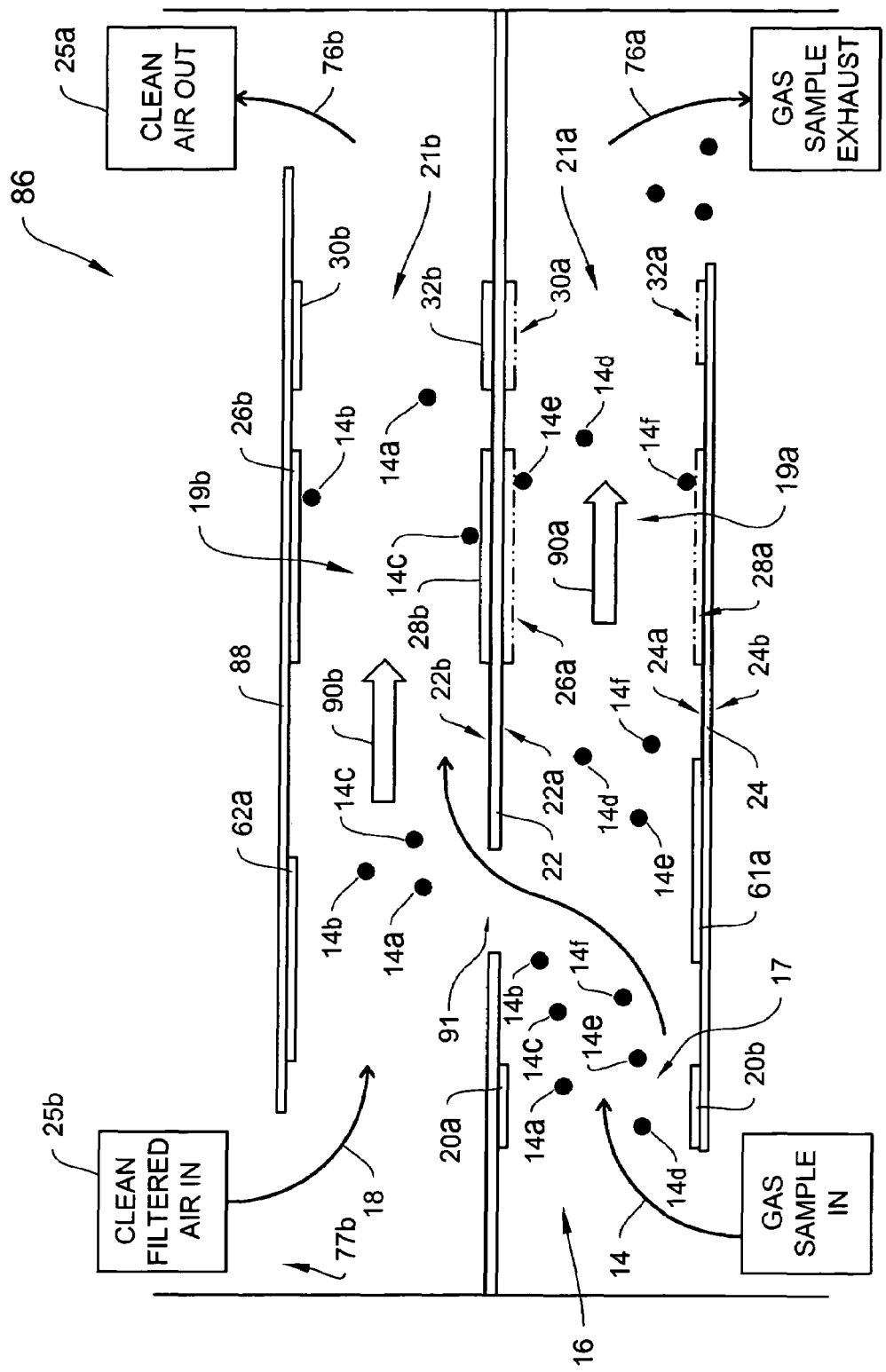
FIG. 6 is a schematic of a multiple layer, multiple flow path DMS system according to an illustrative embodiment of the invention.

FIG. 6 is a conceptual drawing of a multiple layer compact DMS 86 according to an illustrative embodiment of the invention. As shown, the DMS 86 provides two flow paths 90a and 90b. The sample 14 eluting from the GC column enters inlet 16 and is ionized by the ionization electrodes 20a and 20b in the ionization region 17. The steering electrodes 61a and 62a steer at least a portion 14a-14c of the sample ions 14a-14f into the flow path 90b. The remainder of the sample ions 14d-14f are directed along the flow path 90a. As described above, the ions may be directed along the two paths 90a and 90b for any number of reasons, including, but not limited to, pre-separating out portions of the sample (e.g., neutrals) that are not to be analyzed, to analyze multiple constituents of the sample 14 concurrently, or to analyze the sample 14 at two different Vcomp and/or Vrf voltages along the two different paths 90a and 90b.

As shown, the flow path 90b includes a filter region 19b and a detector region 21b. The filter electrodes 26b and 28b, depending on the applied Vcomp and Vrf, pass a particular species 14a of the sample ions 14a-14c into the detector region 21b. As described above, the remainder of the ions 14b and 14c are neutralized by the filter electrodes 26b and 28b. The detector electrodes 30b and 32b detect the intensity of the sample species 14a over the range of Vcomp, Vrf and other field conditions applied to the filter electrodes 26b and 28b. The flow path 90b also includes an inlet 77b for flowing filtered air or other suitable drift gas 18 into the flow path 90b, and an outlet 76b for flowing the drift gas 18 out of the flow path 90b. The pump/handler 25a pumps the drift gas out of the outlet 76b, while the pump 25b introduces or recirculates the filtered drift gas 18 into the inlet 77b.

Optionally, the flow path 90a also includes a filter region 19a and a detector region 21a. The optional filter electrodes 26a and 28a and optional detector electrodes 30a and 32a operate in a similar fashion to their flow path 90b counterparts, neutralizing some species 14e and 14f while detecting other species 14d. The sample gas is exhausted out of the flow path 90a via the outlet 76a. This illustrative embodiment provides a parallel DMS configuration in which different gas conditions may be presented in each. With a suitable control applied to the two steering electrode 61a and 62a, selection can be made as to which region the ions are sent. Because each path 90a and 90b can have its own gas and bias condition, multiple sets of data can be generated for a single sample 14. This enables improved species discrimination in a simple structure, whether or not a GC is used for sample introduction.

There are several additional advantages to the illustrative DMS configuration 86 of FIG. 6. For example, it allows for independent control of the flow rates in the flow paths 90a and 90b, provided the pressures are balanced or appropriately controlled at the open region 91 between the flow paths 90a and 90b. This means that a higher or lower flow rate of the sample 14 in the flow path 90a may be used, depending on the particular GC system, while the flow rate of the ions through the ion filter region 19b of the flow path 90b can be maintained constant allowing, consistent, reproducible results. If the flow rate through the ion filter region 90b had to be changed due to the sample introduction system, this would adversely effect the DMS measurement. The efficiency of the ion filtering would be impacted and the location (e.g., compensation voltages) at which ion peaks occur in the DMS spectrometer would be different at the different flow rates.

This in turn would require different high voltage high frequency fields to be used, which would make for a complicated electronics system.

Another advantage is that the neutrals can be deflected along the flow path 90a so that the ion filter region 19b can be kept free of neutrals. This is important when measuring samples at high concentrations coming out of the GC column. Because the amount of ions the ionization source 20 can provide is limited, if there are too many sample molecules, some of the neutral sample molecules may cluster with the sample ions and create large molecules which do not look at all like the individual sample molecules. By injecting the ions immediately into the clean gas flow in flow path 90b, and by exposing the ions to the high voltage high frequency field of the filter region 19b, the molecules can be de-clustered, and the ions caused to produce the expected spectra.

A further advantage of the DMS 86 is that the dynamic range. By adjusting the ratios of the drift gas 18 and GC-sample/carrier gas 14 volume flow rates coming into ionization region 17, the concentration of the compounds eluting from the GC can be controlled/diluted in a known manner so that samples are delivered to the filter region 19b at concentrations that are optimized for the filter electrodes 28b and 28b and detector electrodes 30b and 32b to handle. In addition, the steering electrodes 61a and 62a can be pulsed or otherwise controlled to determine how many ions at a given time enter into the flow path 90b.

Figure 7:
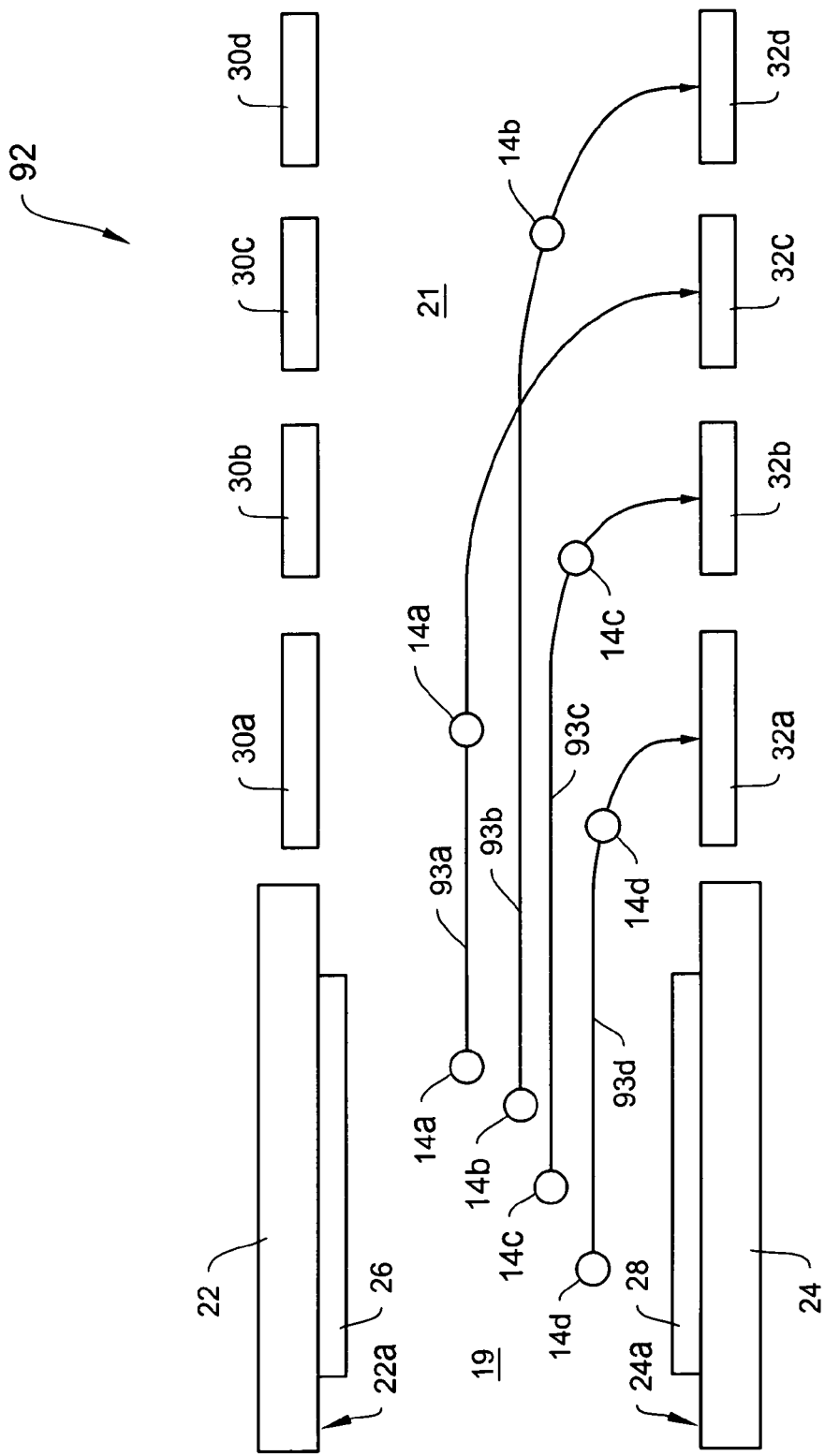
FIG. 7 is a conceptual diagram showing segmented detector structure in a DMS system for enhanced compound discrimination.

FIG. 7 is a conceptual diagram showing an alternative filter/detector section 92 for a compact DMS according to an illustrative embodiment of the invention. As in previously described embodiments, the filter region 19 includes filter electrodes 26 and 28 to filter select ion species. According to this embodiment, the detector electrodes 30 and 32 are segmented. Different species ions 14a-14d of the sample 14 deflect along different trajectories 93a-93d, respectively, as they pass through filter region 19 between filter electrodes 26 and 28. The trajectories 93a-93d are determined, for example, according to their low field mobility, which is determined, in part, by ion size, charge, mass and shape, and cross-section. Thus, the detector segment 32a detects the concentration of ion species 14d, while the detector segment 32d detects the concentration of the ion species 14b. Since each detector segment may detect a particular ion species, the configuration of FIG. 7 increases detector spectrum resolution. Although, the ion species 14a-14d are shown as being detected by the detector segments 32a-32d, detection by the detector segments 30a-30d may also occur. Additionally, each of the detector segments, may be biased differently to effect which ion species it detects and whether it detects positive or negative mode ions.

As can be seen from the above described illustrative embodiments, the compact GC-DMS of the invention provides many advantages over prior art systems. By way of example, the detection limits of the GC-DMS of the invention are about an order of magnitude better than those of a conventional GC-FID systems.

Figure 8:
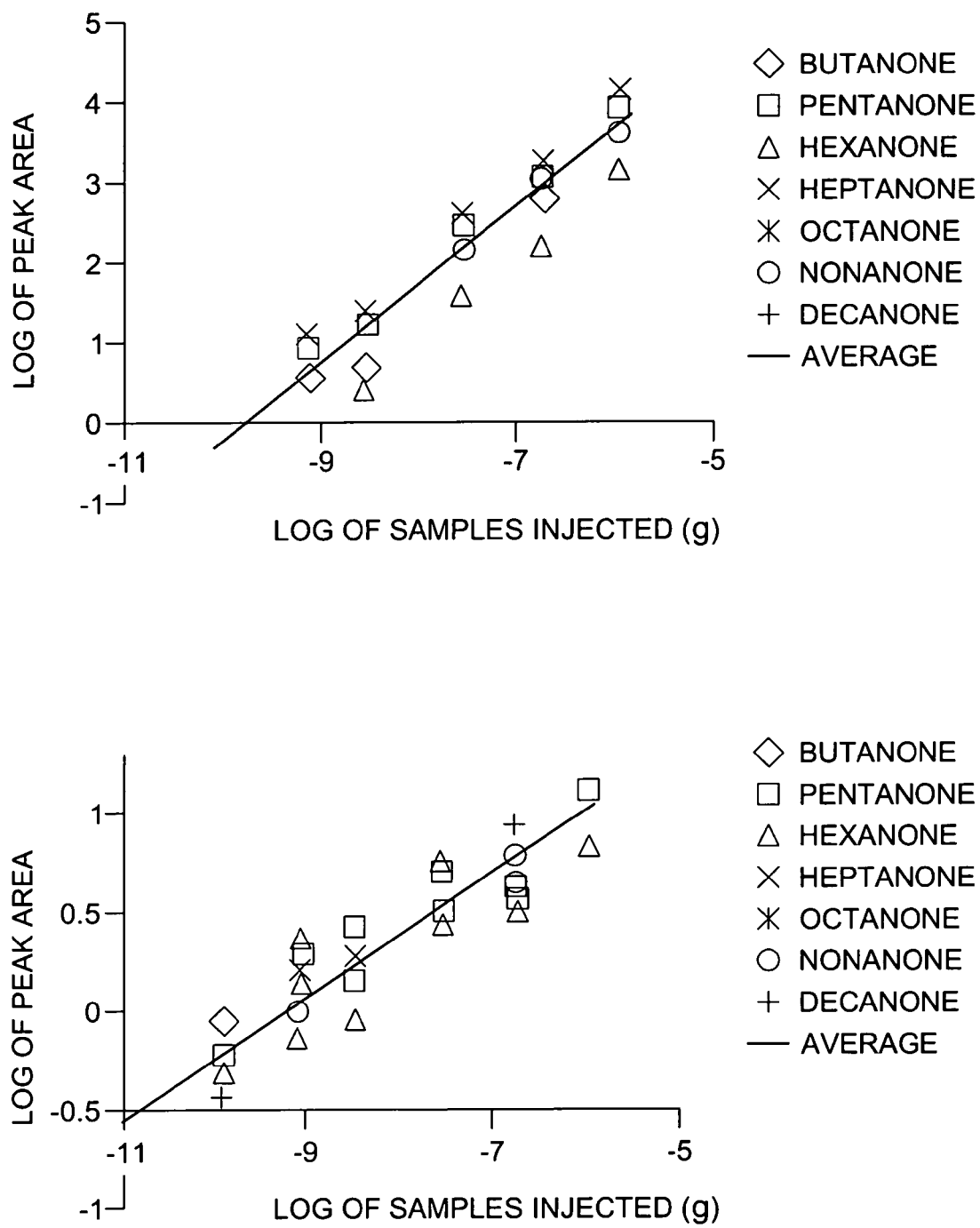
FIG. 8 shows experimental data comparing the detection limits of the DMS with an industry standard Flame Ionization Detector (FID).

FIG. 8 is a graph comparing response times of a conventional FID with those of a compact DMS according to the invention, as a function of compound concentration for a homologous Ketone mixture. (Note average FID detection limit is 2E-10 g, while average DMS detection limit is 2E-11g.). Similarly to a MS, the information provided by the GC-DMS scans offers the ability to obtain unambiguous compound identification.

Figure 9:
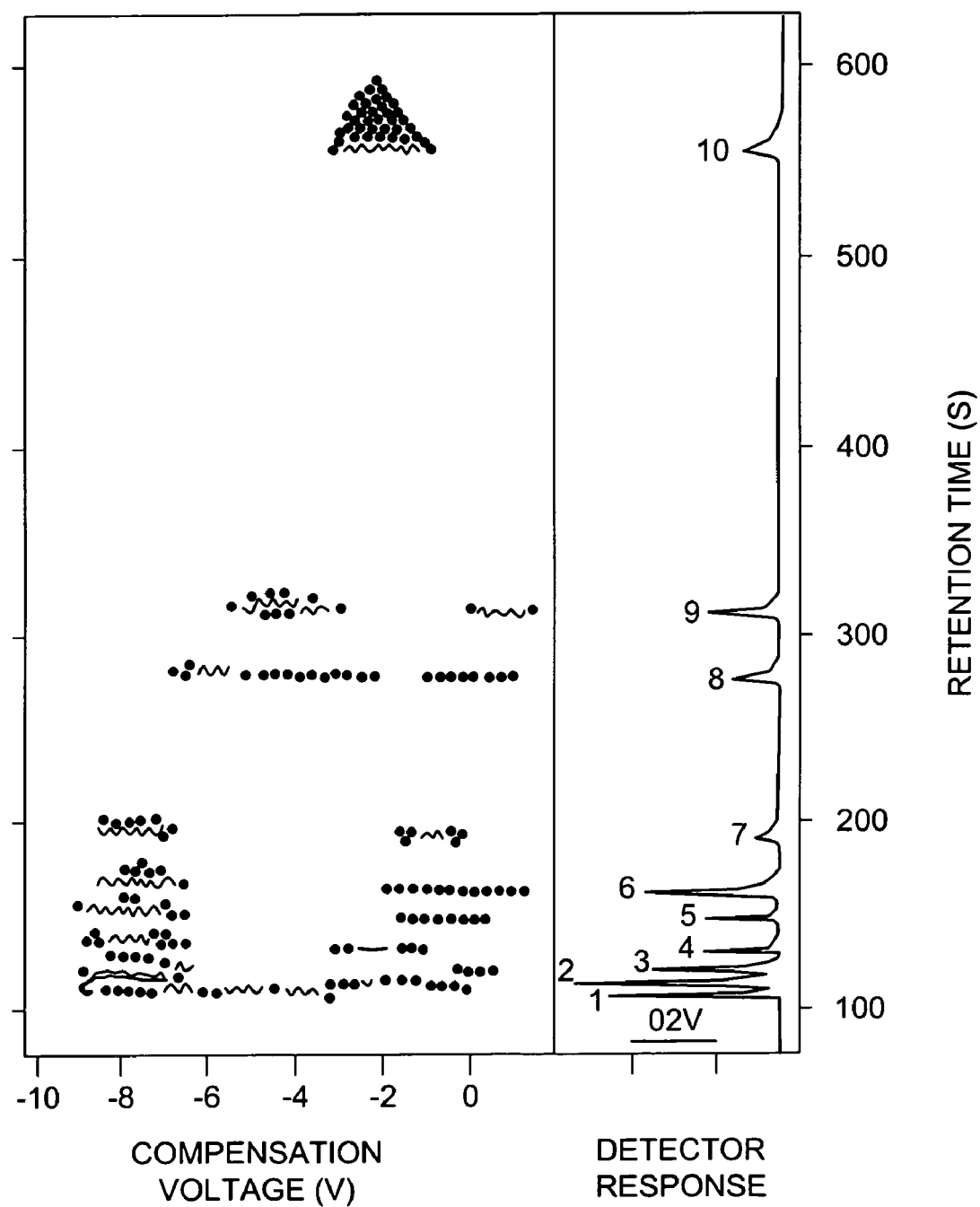
FIG. 9 shows 2-dimensional and 3-dimensional plots of the GC-DMS spectra for a homologous alcohol mixture where the third dimension in the left plot is intensity, which is indicated by the density of the dots.

The system of the invention, according to one feature, may be operated in a fast GC mode, which the prior FIS cannot keep up with. In this mode, the DMS generates a complete spectra of the ions under the GC peaks, and generates enough data to enable 2- and 3-dimensional graphical representations of the data, as shown in FIG. 9 as a topographic plot. The result of the 2-dimensional and 3-dimensional plots provide fast, high accuracy identification of the compounds being detected. This is an important advantage of the invention and leads to exceptionally meaningful chemical detections and characterizations.

FIG. 9 is a GC-DMS chromatogram according to an illustrative embodiment of the invention. In the GC-DMS of the invention, the chromatogram (right frame) represents only a part of the generated data. Unlike the FID, the GC-DMS of the invention also provides an associated two-dimensional plot (left frame) of ion intensity, as indicated by the gradient, versus compensation voltage. The left frame of information is unique to the presently disclosed DMS spectrometer 10b. Using a 2-dimensional plot of Vcomp versus retention time to discriminate between ion species is also unique to the invention. Thus, this combination of data, captured by the GC-DMS of the invention, provides a previously unavailable mechanism for fingerprinting the compounds eluted from a GC.

The right frame of FIG. 9 shows the sum of the peak intensities for the product ions particular retention times. This sum can be calculated, for example, by summing the intensities of all the spectra in software, or if an ionization source that produces a reactant ion peak (example of sources are radioactive and corona discharge sources) is used, by monitoring the changes in the intensities of the reactant ion peak.

The GC-DMS of the invention advantageously features the ability to obtain the retention time spectra by monitoring changes in intensity of the Reactant Ion Peak (RIP peak). This further enables the ability to provide a chemical sensor that is able to rapidly produce accurate, orthogonal data for identification of a range of chemical compounds. Quite beneficially, the overall attributes of the GC-DMS of the invention results in analytical protocols that can be performed by less trained personnel, with faster sample analysis at lower cost.

More specifically, the reactant ion peak is a chemical peak produced by the ionization of the "background" carrier gas CG and produces a fixed intensity ion signal at the detector at a particular Vcomp (shown in FIG. 10). The intensity of the reactant ion peak is determined by the activity (energy) of the ionization source. When an organic compound is eluted from the GC, some charge is transferred from the reactant ion compounds to the eluted compound creating a product ion. As shown in the lower graph of FIG. 10, the formation of the product ion results in a decrease in the intensity of the reactant ion peak (amount of reactant ions available). The amount of decrease in the reactant ion peak intensity is equal to the amount of ions required to create the product ions. If multiple product ions are produced at the same time, the reactant ion peak intensity decreases in an amount equal to the intensity of the product ions intensities combined. In other words, by monitoring the changes in the reactant ion peak, the same information can be obtained as summing all of the individual product ion peaks.

In the field, or under particular environmental conditions, such as variable humidity or sample concentrations, the retention times of compounds may shift from their expected values. When analyzing an unknown complex mixture, this may be a serious problem. To correct for this shift, a known standard, at a known concentration, is run through the GC first to calibrate it. However, calibration to a standard takes time and adds complexity. Also, the standard is a consumable, and is inconvenient to use in the field.

A feature of the GC-DMS of the invention is that it provides three levels of information: retention time (GC); compensation voltage (DMS); and ion intensity (DMS). Additionally, both positive and negative spectra can be obtained concurrently. Because the DMS of the invention provides additional orthogonal information, even though the GC retention time for a compound may shift, the GC-DMS combination can, nevertheless, provide an accurate identification of the compound, without the need of recalibration to a standard.

Figure 11:
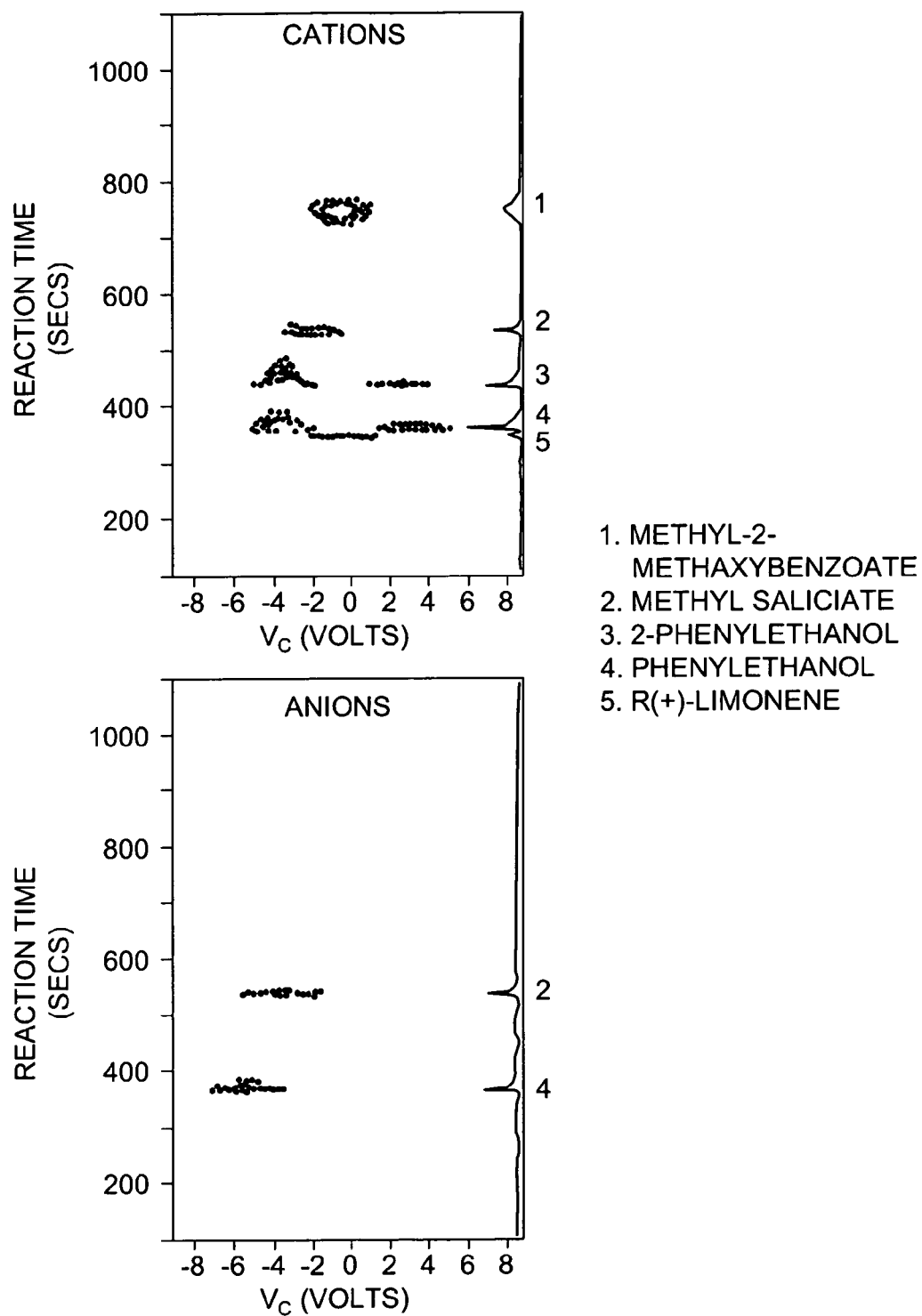
FIG. 11 shows the concurrently obtained spectra and topological plots for positive and negative ions using a DMS as a detector.

The GC-DMS spectra for an insect pheromone mixture is shown in FIG. 11, where positive and negative spectra are obtained simultaneously from a compact DMS of the invention while analyzing a mixture of pheromone simulants. Notice that under GC peak 2 and 4 there are both anion and cations present. The positive and negative spectra are obtained substantially simultaneously, eliminating the need of serial analysis under different instrumental conditions, as required in MS.

Substantially simultaneous detection cuts down on analysis time, since only one scan is required to obtain multiple species detection. Also it provides a much richer information content compared to TOF-IMS, so that one can get a better identification of the ion species being detected. For example, in FIG. 11, the entire measurement took approximately 800 seconds to see all of the GC peaks in the sample. If we were to repeat this experiment for the negative (anions) we would have to wait another 800 seconds. It is also important when limited samples are available and measurements can only be performed once.

The compact GC-DMS of the invention is described above with regard to particular illustrative DMS structures and layouts. Next will be described additional illustrative layouts for the DMS of the invention.

FIG. 12A is conceptual diagram of a compact GC-DMS system 100 that is implemented on a substrate 106. The substrate 106 may be made of silicon, Pyrex™ glass, any material commonly included in electronic circuit boards, or any other suitable material. The compact GC-DMS system 100 also includes a compact GC 102, an array 104 of DMS analyzers 104a-104f (collectively 104), a GC inlet 108, and a GC outlet 110. Two or more of the DMS analyzers 104 may share a common flow channel and/or common ion filter. Regardless, laminar flow in the common flow channel can maintain a fluid, e.g., a gas, in a straight trajectory. Thus, the laminar fluid flow in a common channel may allow multiple analyzers to analyze separate portions of a sample. Also due to the laminar fluid flow, multiple analyzers may scan, at multiple different field compensation voltages, separate portions of a sample in a common flow channel concurrently or near simultaneously. Alternatively, the flow channel of each of the DMS analyzers 104 may be isolated, in whole or in part, from the flow channel of other DMS analyzers 104. The GC capillary column 112 may be configured to include an outwardly winding spiral as shown in FIG. 12A. In certain embodiments, some or all of the components of the GC-DMS system 100 are included in an integrated circuit formed in a single package.

In operation, a sample S is introduced into the GC inlet 108 and traverses the GC column 112. Due to the GC process, constituent compounds become separated in time and arrive at the GC outlet 110 at different times. Although not shown, a makeup drift gas, such as the drift gas 18 discussed above with respect to FIG. 2A, may be combined with a sample S constituent at the GC outlet 110 to establish the required gas flow for an analyzer 104. As discussed above, a GC may have a column flow rate of about 1 ml/min while an analyzer 104 may require a flow rate of about 100 ml/min-500 ml/min. The drift gas provides the additional makeup flow needed by an analyzer 104.

One or more analyzers 104a-104a and/or an analyzer array 104 may be in fluid communication with the GC outlet 110. For example, analyzers 104a through 104f may be connected in parallel to facilitate concurrent or near-simultaneous detection of sample S constituents at select times. Alternatively, an analyzer 104a may be activated at one time to detect a particular sample S constituent, while another analyzer 104f may be activated at another time to detect a different sample S constituent. Because sample S constituents are expected to arrive at different times at the GC outlet 110, the analyzer array 104, individual analyzers of the array 104, and/or combinations of individual analyzers of the array 104 may be controllably activated at certain times to detect certain sample S constituents. Thus, one or more analyzers, e.g., analyzer 14a, receive the sample S constituent at a certain time and perform an analysis to identify and/or measure the concentration of a detected sample constituent ion species.

In certain illustrative embodiments, the GC column 112 employs a carrier gas consisting substantially of air while at least one ion mobility based sample analyzer of the analyzers 104 employs a drift gas consisting substantially of air. The analyzer array 104 may include various types of analyzer systems such a DMS, IMS, MS, TOF IMS, FTIMS, faraday plates, and the like ion mobility based analyzers. The analyzer array 104 may include multiple analyzers that are arranged in and operate in parallel, series, or a combination of parallel and series. In one illustrative embodiment where the analyzers 104a-f are DMS analyzers, each of the analyzers of the analyzer array 104 are tuned to different Vcomp or Vrf values to enable concurrent detection and/or measurement of different constituents of a sample. For example, DMS analyzer 104a may be tuned to Vcomp=$V_{C1}$ and Vrf=$R_{f2}$ as shown in FIG. 12A.

According to one illustrative embodiment, the GC-DMS system 100 analyzes a sample by flowing the sample through the at least one GC column, e.g., GC column 112, to temporally separate constituents of the sample S from each other. The GC-DMS system 100 also analyzes at least one of the eluted constituents of the sample S from the GC column 112 based on the ion mobility characteristics of the constituents. In some embodiments, the GC-DMS system 100 analyzes a plurality of eluted constituents from at least one GC column such as GC column 112 concurrently or substantially simultaneously using a plurality of analyzers of the analyzer array 104.

FIG. 12B is a conceptual diagram of a compact GC-DMS system 114 having a meandering GC column 116 and an array 118 of analyzers that are implemented on a common substrate 120 according to an illustrative embodiment of the invention. The substrate 120 may be made of silicon, Pyrex™ glass, and any other material commonly included in electronic circuit boards, and the like. The GC capillary column 116 may be configured as a planar meandering capillary column. It also may be configured to include one or more straight, curved helical, spiraling, counter-winding, packed column, and/or counter spiraling portions and extend in two or three dimensions. The GC capillary column 116 may also be configured as multiple capillary columns. Illustratively, it is size limited only by the size of the medium in which the column is attached and/or embedded.

In operation a sample S is introduced into the GC inlet 122 and traverses the GC column 116. Due to the GC process, constituent compounds become separated in time and arrive at the GC outlet 124 at different times. Although not shown, a makeup carrier gas may be combined with a sample S constituent at or just after the GC outlet 124 to establish the required gas flow for an analyzer of the array 118. One or more analyzers and/or an analyzer array 118 may be in fluid communication with the GC outlet 124 to provide detection of the sample S constituents exiting the GC at GC outlet 124.

In a further embodiment, at least one ion mobility based sample analyzer of the analyzer array 118 has low enough sample residence times and operates fast enough to provide a plurality of scans over a range of field conditions (e.g., field compensation voltage (Vcomp), radio frequency field excitation voltage (Vrf), and the like) for a single elution peak from at least one GC column such as GC column 116. In one implementation, at least one ion mobility based sample analyzer of the array 118 has a sample residence time of less than about 1 second, 500 ms, 250 ms, 100 ms, 50 ms, 25 ms, 10 ms, 5 ms, or 1 ms. According to one feature, at least one ion mobility based sample analyzer of the array 118 is sized and shaped to perform a single measurement of at least a portion of one of the eluted constituents from the GC column 116 at a particular filter field condition in less than about 100 ms, 50 ms, 25 ms, 10 ms, 5 ms, 2 ms, or 1 ms.

According to another feature, at least one ion mobility based sample analyzer of the array 118 performs a scanned measurement of at least one of the eluted constituents from the GC column 116 over a range of field compensation voltages of at least about 50 Vdc in less than about 10 second, 5 seconds, 4 seconds, 3 seconds, 2 seconds, or 1 second. Alternatively, at least one ion mobility based sample analyzer or the array 118 performs a scanned measurement of at least one of the eluted constituents from the GC column 116 over a range of field compensation voltages of at least about 100 Vdc in less than about 10 seconds, 5 second, 4 seconds, 3 seconds, 2 seconds, or 1 second.

FIG. 12C is a conceptual diagram of a compact GC-DMS system 126 having a spiral GC column 128 and multiple DMS analyzers 130 and 132 at various locations within the GC column 128 according to an illustrative embodiment of the invention. The GC-DMS system 126 also includes a GC inlet 134 and GC outlet 136.

In operation, a sample S is introduced into the GC inlet 134 and traverses the GC column 128. Due to the GC process, constituent compounds become separated in time and arrive at the one or more analyzers, e.g., analyzers 130 and 132, within the column 128 at different times. Although not shown, a makeup drift gas may be combined with a sample S constituent at the inlet to each analyzer 130 and 132 to establish the required gas flow for each analyzer 130 and 132. Also, multiple ion mobility based sample analyzers or an array of analyzers may be employed at various intermediate locations along the length of the GC column 128 between the first and second terminal ends, e.g., the GC inlet 134 and the GC outlet 136 respectively, to enhance the rate of analysis. The sample S constituents, separated in time, may exit the GC column at GC outlet 136 to be analyzed by another ion mobility based analyzer system.

Furthermore, in certain illustrative embodiments, the analyzer 130 is tuned to detect and/or measure the concentration of certain constituents while the analyzer 132 is tuned to detect and/or measure the concentration of different constituents. Additional analyzers may be employed along the length of the GC column 128 that are tuned to detect and/or measure the concentration of yet other sample constituents in the GC column 128. After constituents are detected and/or measured in an analyzer, the sample molecules are neutralized and continue to flow through the GC column 128. The GC column 128 may be considered a collection of multiple GC columns that are interconnected by one or more analyzers.

Figure 12D:
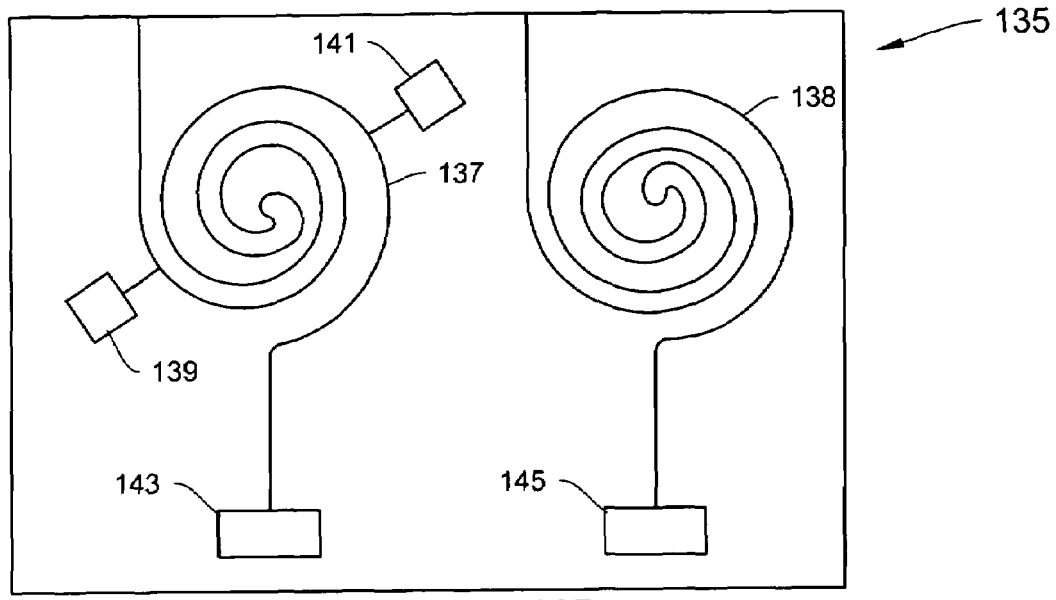
FIG. 12D is a conceptual diagram of a compact GC-DMS system including two GC-DMS systems arranged in parallel on a substrate according to an illustrative embodiment of the invention.

FIG. 12D is a conceptual diagram of a compact GC-DMS system 135 including two GC-DMS systems arranged in parallel on a substrate according to an illustrative embodiment of the invention. The GC-DMS system 135 includes a first GC column 137 connected to a first DMS analyzer 143 and a second GC column 138 connected to a second DMS analyzer 145. The first GC column may also be connected to one or more additional DMS analyzers, such as DMS analyzer 139, and various locations along the GC column 137. Likewise, the GC column 128 may include one or more addition DMS analyzers. The various components of the GC-DMS system 135 may be embedded on one or more substrates, within a one or more integrated circuits or microchip assemblies.

Other embodiments where the GC columns are on different substrates or are discrete capillary columns, or packed columns are also envisioned and possible.

In the operation of the present embodiment, a sample S is introduced into an inlet of and traverses the GC column 137. The sample S is also concurrently, simultaneously, or near simultaneously introduced into and traverses the GC column 138. Due to the GC process, constituent compounds become separated in time and arrive at the one or more analyzers, e.g., analyzers 139 and 143, within the column 137 at different times. Although not shown, a makeup drift gas may be combined with a sample S constituent at the inlet to each analyzer 139 and 143 to establish the required gas flow for each analyzer 139 and 143. Similarly, due to the GC process, constituent compounds become separated in time and arrive at the one or more analyzers, e.g., analyzer 145, within the column 138 at different times. Also, multiple ion mobility based sample analyzers or an array of analyzers may be employed at various intermediate locations along the length of the GC column 137 and/or 138 to enhance the rate of analysis. The sample S constituents, separated in time, may exit the DMS analyzer 143 and/or 145 and be analyzed by another ion mobility based analyzer system.

Furthermore, in certain illustrative embodiments, the analyzer 143 is tuned to detect and/or measure the concentration of certain constituents while the analyzer 145 is tuned to detect and/or measure the concentration of different constituents. Additional analyzers may be employed along the length of the GC column 137 and/or 138 that are tuned to detect and/or measure the concentration of yet other sample constituents in the GC column 137 and/or 138.

Figure 12E:
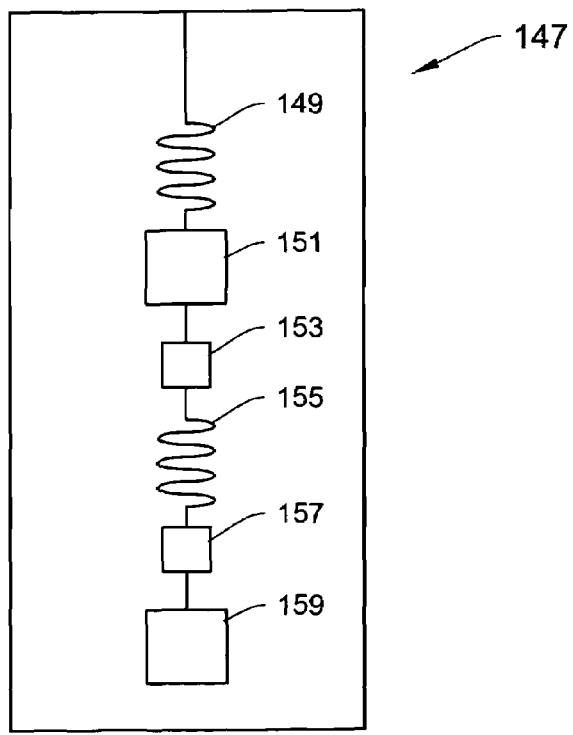
FIG. 12E is a conceptual diagram of a compact GC-DMS system including two GC-DMS systems arranged in series on a substrate according to an illustrative embodiment of the invention.

FIG. 12E is a conceptual diagram of a compact GC-DMS system 147 including two GC-DMS systems arranged in series on a substrate according to an illustrative embodiment of the invention. The GC-DMS system 147 includes a first GC column 149 connected to a first DMS analyzer 151 and a second GC column 155 connected to a second DMS analyzer 159. The first GC column 149 and/or first DMS analyzer 151 may also be connected to one or more additional traps, such as trap 153. The trap 153 may include, for example, a cold spot, cold trap, molecular sieve trap, a polydimethylsiloxane (PDSM) based trap, microfluidic trap, and/or a pre-concentrator trap. The trap can also be a SPME fiber which is heated at a particular time and rate to release the sample, thus acting as an injector for the GC. The trap can also be a packed column, such as for example, a metal tube packed with molecular sieve material such as 10×, chromasorb W, carbon, charcoal, carbon nano-tubes, nanofabricated particles, various organic materials, polymers such as PDMS. Likewise, the GC column 155 and/or DMS analyzer 159 may be connected may include one or more addition traps such as trap 157. The various components of the GC-DMS system 147 may be embedded on one or more substrates, within a one or more integrated circuits or microchip assemblies.

In operation, a sample S is introduced into an inlet of and traverses the GC column 149. Due to the GC process, constituent compounds become separated in time and arrive at DMS analyzer 151 at different times. Although not shown, a makeup drift gas may be combined with a sample S constituent at the inlet to the DMS analyzer 151 to establish the required gas flow for the DMS analyzer 151. The sample S may then be introduced into the trap 153 to enable the collection and/or concentration of certain sample constituents before introduction into the GC column 155. Due to the GC process or phase of the column, or type of column used, constituent compounds become separated in time and arrive at another trap 157 and/or the analyzer 159, at different times. Also, multiple ion mobility based sample analyzers or an array of analyzers may be employed at various intermediate locations along the length of the GC columns 149 and/or 155 to enhance the rate of analysis. The sample S constituents, separated in time, may exit the DMS analyzer 159 and be analyzed by another ion mobility based analyzer system.

Furthermore, in certain illustrative embodiments, the analyzer 151 is tuned to detect and/or measure the concentration of certain constituents while the analyzer 159 is tuned to detect and/or measure the concentration of different constituents. Additional analyzers may be employed along the length of the GC columns 149 and/or 155 that are tuned to detect and/or measure the concentration of yet other sample constituents.

In another embodiment, a GC column such as GC columns 149 and 155 includes microfabricated and/or etched silicon columns. The columns may be formed from reactive ion etching of silicon substrates and then dynamically coated with a nonpolar and/or moderately polar substance. For example, a nonpolar substance may include dimethyl polysiloxane (stationary phase). A moderately polar substance may include trifluoropropylmethyl polysiloxane. Each column may use air at atmospheric pressure as a carrier gas. Alternatively, an inert gas and/or Nitrogen may be employed. In one embodiment, the GC column includes a channel etched on a silicon chip with a Pyrex™ wafer cover.

In another embodiment, the column can be formed using ceramic fabrication technologies, such as low temperature co-fired ceramic (LTCC), thick film ceramic where the ceramic is selectively removed by laser cutting the ceramic. In yet other embodiments the both the GC and DMS can be formed from or on ceramic or using ceramic materials such as alumina for example. The ceramic materials may be replaced by polymers or plastics such as PDMS and liquid crystal polymer, LCP. The GC-DMS or GC or DMS alone may be formed from injection molding of plastics and polymers.

These microfabricated GC columns and systems advantageously operate under low volumetric flow rates, allowing detectors that are relatively more compact having relatively small residence times. The microfabricated GC columns are also relatively easy to repeatably manufacture in a low cost manner. More particularly, microfabricated GC columns can be efficiently integrated with microfabricated DMS analyzers and other ion mobility based analyzers.

The DMS may incorporate a longitudinal electric field drive. The longitudinal electric field may eliminate the need for a transport gas flow through the DMS. As a result only the GC column flow rate which may range from less than 1 microliter/minute to more than 100 milliliter/minute, more than 200 ml/min, more than 500 ml/min, more than 1 liters/min, more than 10 liters/minute, is required and no transport gas is required in the DMS. In other words, a very low gas consumption is required only for the gas chromatograph. The carrier gas in the GC may be air, filtered air, nitrogen, Hydrogen, Helium, and many other gasses. The carrier gas in the GC may be re-circulated through filters from the exhaust of the DMS and fed back through the GC by a pump. Filtering, or elimination of undesirable compounds from the carrier or transport gas can be achieved using membranes, adsorbents, molecular sieves, various types of filters, catalyst, and many other means. In other envisioned embodiments, the gas flow rate in the GC would be matched to the DMS.

Figure 13:
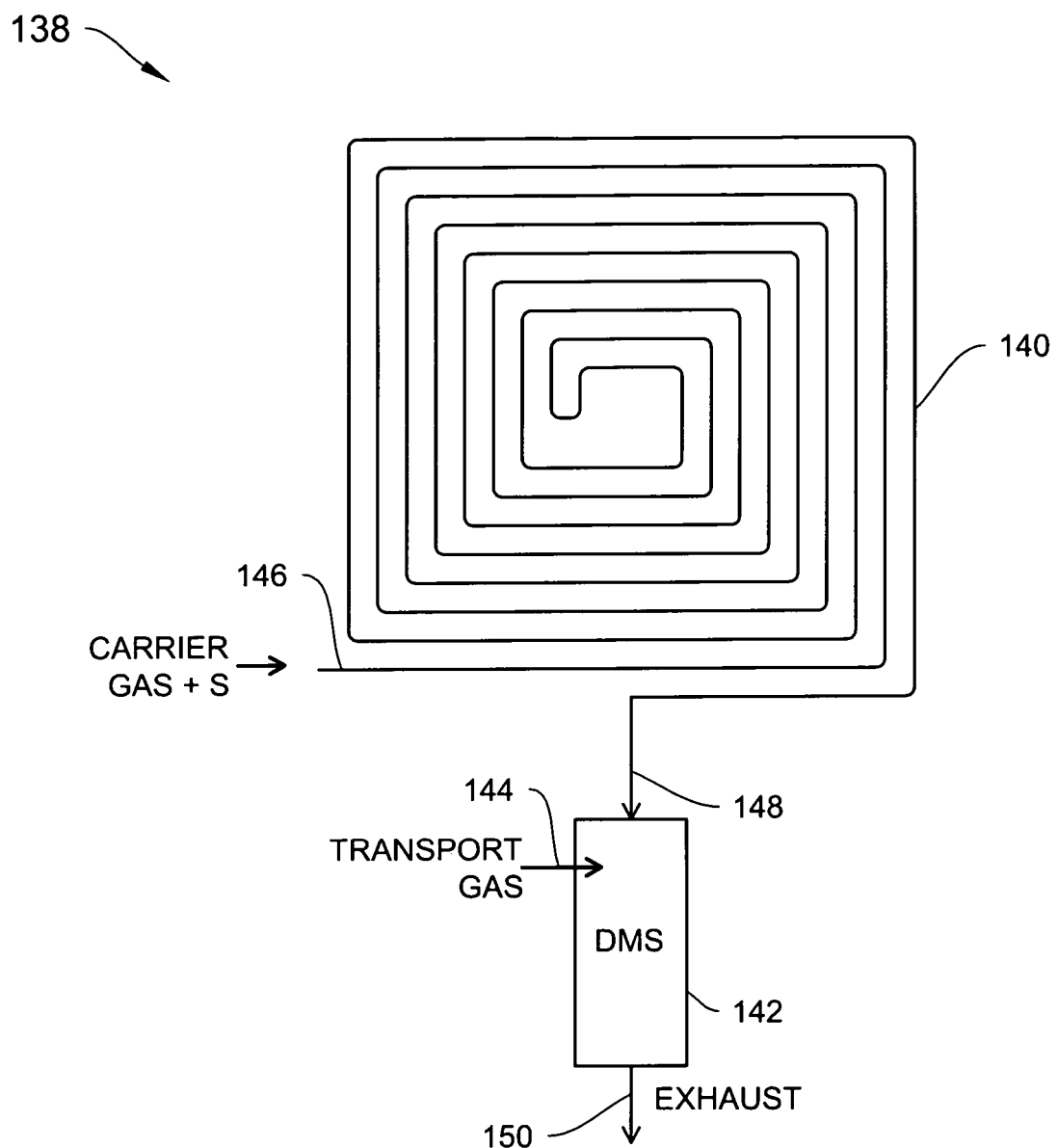
FIG. 13 is a conceptual diagram of a compact GC-DMS system having a compact GC column and a DMS analyzer with a transport gas inlet for providing a drift/transport gas for increasing the flow volume through the DMS according to an illustrative embodiment of the invention.

FIG. 13 is a conceptual diagram of a compact GC-DMS system 138 having a micro-fabricated and compact rectangular spiral/counter-spiral GC column 140 and a DMS analyzer 142 with a transport gas inlet 144 according to an illustrative embodiment of the invention. The GC column 140 is described as spiral/counter-spiral capillary column because it first spirals inwardly to a center point and then spirals outwardly to a peripheral outlet point. The GC column 140 may be formed on a single common substrate along with the DMS analyzer 142. The GC-DMS system 138 also includes a sample S GC inlet 146, a GC outlet 148, and a DMS analyzer outlet 150. The rectangular spiral/counter-spiral GC column may have a rectangular cross section of about 150(w)×260(h) micrometers with a length of about 10 m, 6 m, 3 m, 1.5 m, or 1 m, or less. In certain embodiments, some or all of the components of the GC-DMS system 138 are included on an integrated circuit formed in a single package.

In operation, a sample S is introduced into the GC inlet 146 and traverses the GC column 140. Due to the GC process, constituent compounds become separated in time and arrive at the GC outlet 148 at different times. A makeup drift gas is introduced through transport gas inlet 144 and combined with a sample S constituent at the DMS 142 inlet and/or GC column outlet 148 to establish the required gas flow to enable filtering and detection by DMS analyzer 142. In other words, the transport gas inlet 144 introduces a make up effluent for increasing the flow rate of the eluded constituent from the GC column 140 to a level suitable for detection by the ion mobility based sample DMS analyzer 142. After a sample S constituent is analyzed, it is exhausted from the DMS analyzer 148 through the DMS analyzer outlet 150.

Figure 14A:
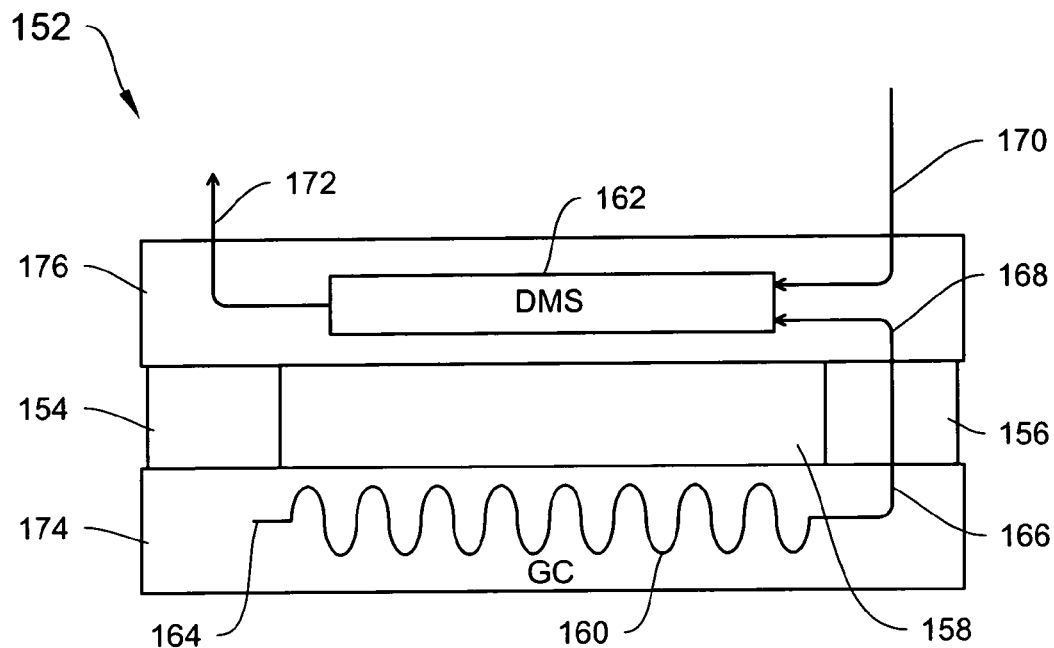
FIG. 14A is a conceptual cross-sectional view of a compact GC-DMS system where spacers provide an air gap between the GC column and the DMS analyzer for thermal insulation according to an illustrative embodiment of the invention.

FIG. 14A is a conceptual cross-sectional view of a compact GC-DMS system 152 where spacers 154 and 156 establish an air gap 158 between the GC column 160 and the DMS analyzer 162 for thermal insulation according to an illustrative embodiment of the invention. The GC-DMS system 152 includes GC column inlet 164, GC column outlet 166, DMS analyzer inlet 168, DMS analyzer outlet 172, substrate 174, transport gas inlet 170, and substrate 176. The GC column 160 and the DMS analyzer 162 are formed on different substrates that are layered and/or stacked in a compact form factor to reduced the GC-DMS system 152 size and/or surface area. The plurality of substrates 174 and 176 are interconnected and stacked, for example, to form a single package, e.g., an IC or chip.

Heaters, and thermistors or thermocouples, or temperatures sensors may also be integrated on the GC and or DMS substrates. At a distance of less than about 1 mm away from the GC channel. The heaters and temperature sensors may be integrated in the GC and or DMS flow channels.

In other embodiments the columns may be nano-machined, or formed from by thin film fabrication processes, such as deposition of silicon nitride, LPCVD, low temperature oxides which may be etched by hydrofluoric acid for example.

In operation, a sample S is introduced into the GC inlet 164 and traverses the GC column 160. Due to the GC process, constituent compounds become separated in time and arrive at the GC outlet 166 and/or DMS analyzer inlet 168 at different times. A makeup drift gas is introduced through the transport gas inlet 170 and combined with a sample S constituent at the DMS analyzer inlet 168 to establish the required gas flow to enable filtering and detection by DMS analyzer 162. After the sample S constituent is analyzed, the it is exhausted from the DMS analyzer 162 through the DMS analyzer outlet 172.

The spacers 154 and 156 establish an air gap 158 between the GC column 160 and the DMS analyzer 162. The air gap 158 provides thermal insulation between the GC column 160 and the DMS analyzer 162 because the GC column may be heated to enhance the separation of constituents of the sample S, while the DMS analyzer 162 operates at another temperature suitable for enhancing filtering and detection of a sample S constituent. The spacers 154 and 156 may be made, for example, from silicon, Pyrex™ glass or any suitable material. The substrates 174 and 176 may also be made, for example, from silicon, Pyrex™ glass or other suitable material.

Figure 14B:
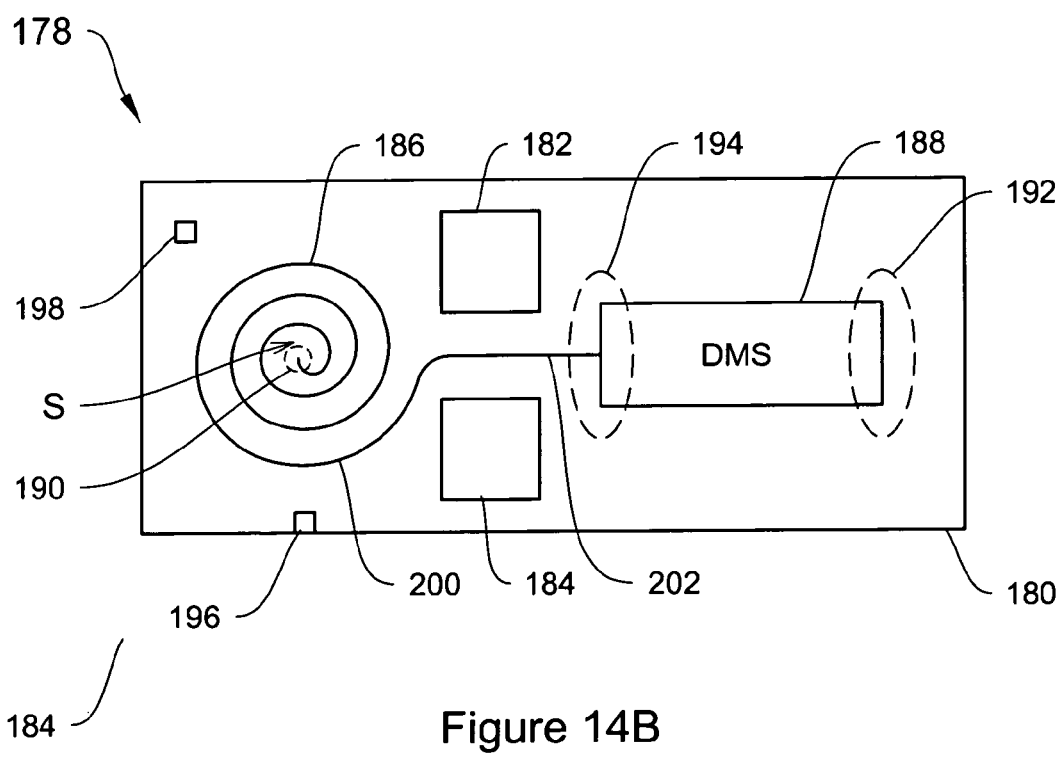
FIG. 14B is a conceptual diagram of a compact GC-DMS system embedded on a substrate having cutouts to provide thermal insulation between the GC column and the DMS analyzer according to an illustrative embodiment of the invention.

FIG. 14B is a conceptual diagram of a compact GC-DMS system 178 embedded on a substrate 180 having cutouts 182 and 184 for providing thermal insulation between the GC column 186 and the DMS analyzer 188 according to an illustrative embodiment of the invention. The GC-DMS system 178 includes a GC column inlet 190, a GC column outlet 200, a transport gas inlet 194, a heater 196, a heater 198, and a DMS analyzer outlet 192.

In operation, a sample S is introduced into the GC inlet 190 and traverses the GC column 186. The GC column 186, optionally, is heated by the heater 196 and/or heater 198 to enhance the GC elution process. Due to the GC process, constituent compounds become separated in time and arrive at the GC outlet 200 and/or DMS analyzer inlet 202 at different times. A makeup drift gas is introduced through transport gas inlet 194 and combined with the sample S at the DMS analyzer inlet 202 to establish the required gas flow for the DMS analyzer 188. After the sample S is analyzed, it is exhausted from the DMS analyzer 188 through the DMS analyzer outlet 192.

In this embodiment of the invention, the various components of the GC-DMS system 178 are arranged in a planar manner within a substrate 180. The cutouts 182 and 184 establish air gaps for providing thermal insulation between the GC column 186 and the DMS analyzer 188. Thus, the thermal energy generated by heaters 196 and 198 for the GC column 186 is substantially insulated from the DMS analyzer 188.

Figure 15:
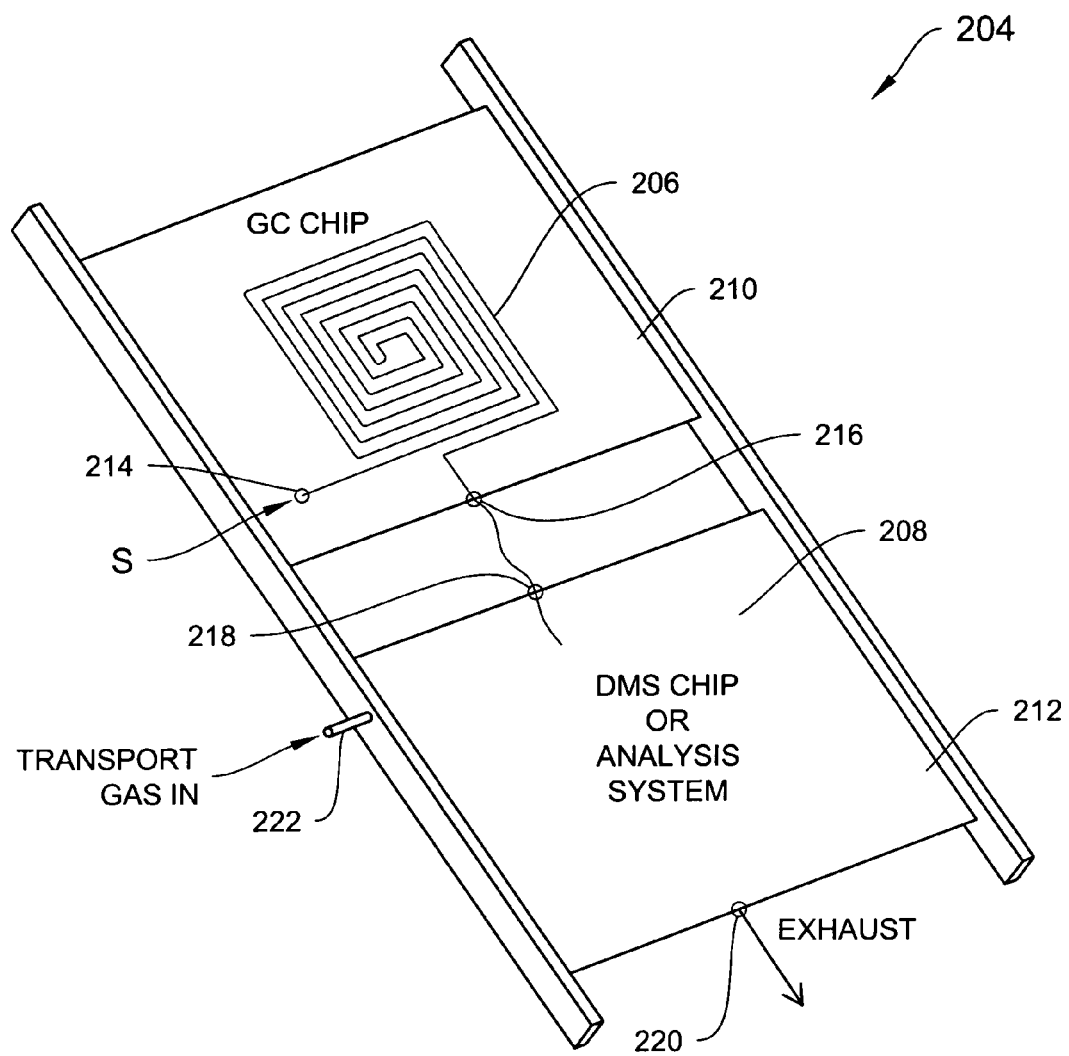
FIG. 15 is a conceptual diagram of a compact GC-DMS system where the GC and DMS analyzers are mounted and/or embedded within separate substrates according to an illustrative embodiment of the invention.

FIG. 15 is a conceptual diagram of a compact GC-DMS system 204 where the GC column 206 and DMS analyzer 208 are located, mounted, and/or embedded within separate substrates 210 and 212, respectively, according to an illustrative embodiment of the invention. The GC-DMS system 204 includes GC inlet 214, GC outlet 216, DMS analyzer inlet 218, DMS analyzer outlet 220, and transport gas inlet 222. The substrates 210 and 212 may be oriented substantially horizontally adjacent to each other, as shown in FIG. 15. Alternatively, the substrates 210 and 212 may be stacked and/or layered to reduce the horizontal surface area covered by the GC column 206 and DMS analyzer 208. The substrates 210 and 212 may be interconnected, but contained in separate packages, e.g., ICs. Alternatively, the substrates 210 and 212 may be interconnected and contained entirely within a single package, e.g., a single IC.

In operation, a sample S is introduced into the GC inlet 214 and traverses the spiral/counter-spiral GC column 206. The GC column 206 may be heated to enhance the GC elution process. Due to the GC process, constituent compounds become separated in time, e.g., temporally, and arrive at the GC outlet 216 and/or DMS analyzer inlet 218 at different times. A makeup drift gas is introduced through the transport gas inlet 222 and combined with the sample S at the DMS analyzer inlet 218 to establish the required gas flow for the DMS analyzer 208. After the sample S is analyzed, it is exhausted from the DMS analyzer 208 through the DMS analyzer outlet 220.

Figure 16:
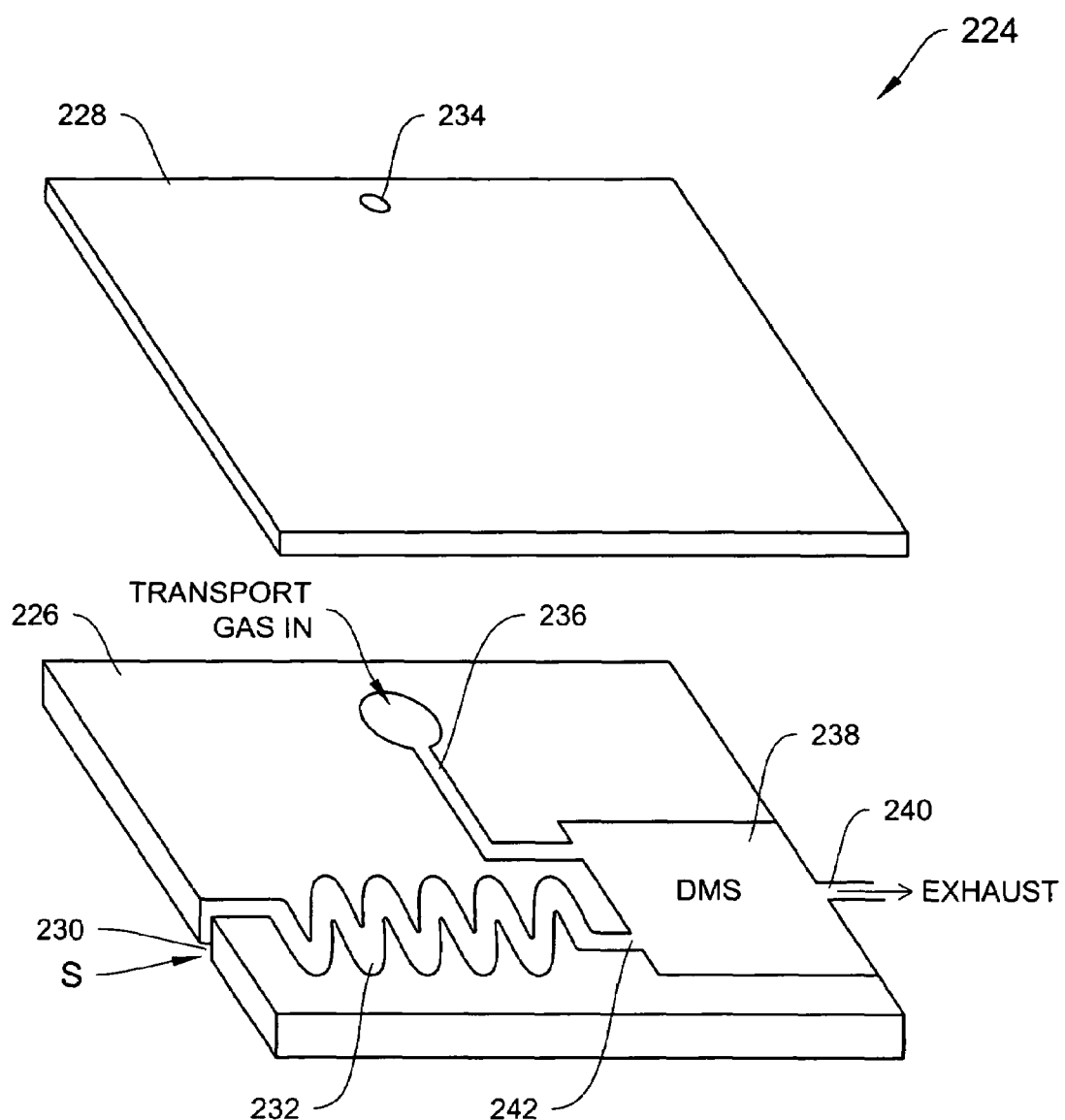
FIG. 16 is an exploded conceptual diagram of a GC-DMS system implemented on a substrate with an optional Pyrex™ glass cap according to an illustrative embodiment of the invention.

FIG. 16 is an exploded conceptual diagram of a GC-DMS system 224 implemented on a substrate 226 with an optional insulating cap 228 according to an illustrative embodiment of the invention. The GC-DMS system 224 includes a GC inlet 230, GC column 232, transport gas inlet 234, transport gas channel 236, DMS analyzer 238, and DMS analyzer outlet 240. The GC inlet 230 may be mechanically drilled in the optional insulating cap 228. The insulating cap 228 may be made of any material that acts as a thermal and/or electrical insulator such as Pyrex™ glass, manufactured by the Corning Glass Works Corporation.

In operation, a sample S is introduced into the GC inlet 230 and traverses the GC column 232. The GC column 232 may be heated to enhance the GC elution process. Due to the GC process, constituent compounds become separated in time and arrive at the DMS analyzer inlet 242 at different times. A makeup drift gas is introduced into the DMS analyzer 238 through transport gas inlet 234 and transport gas channel 236. The makeup gas is combined with the sample S in the DMS analyzer 238 to establish the required gas flow for the DMS analyzer 238. After the sample S is analyzed, the it is exhausted from the DMS analyzer 238 through the DMS analyzer outlet 240. The makeup drift gas may, for example, be air, helium, hydrogen, argon, and/or other inert or suitable gas. The makeup drift gas source may be a pressurized reservoir such as a gas canister and/or a pump of a recirculation system.

Figure 17:
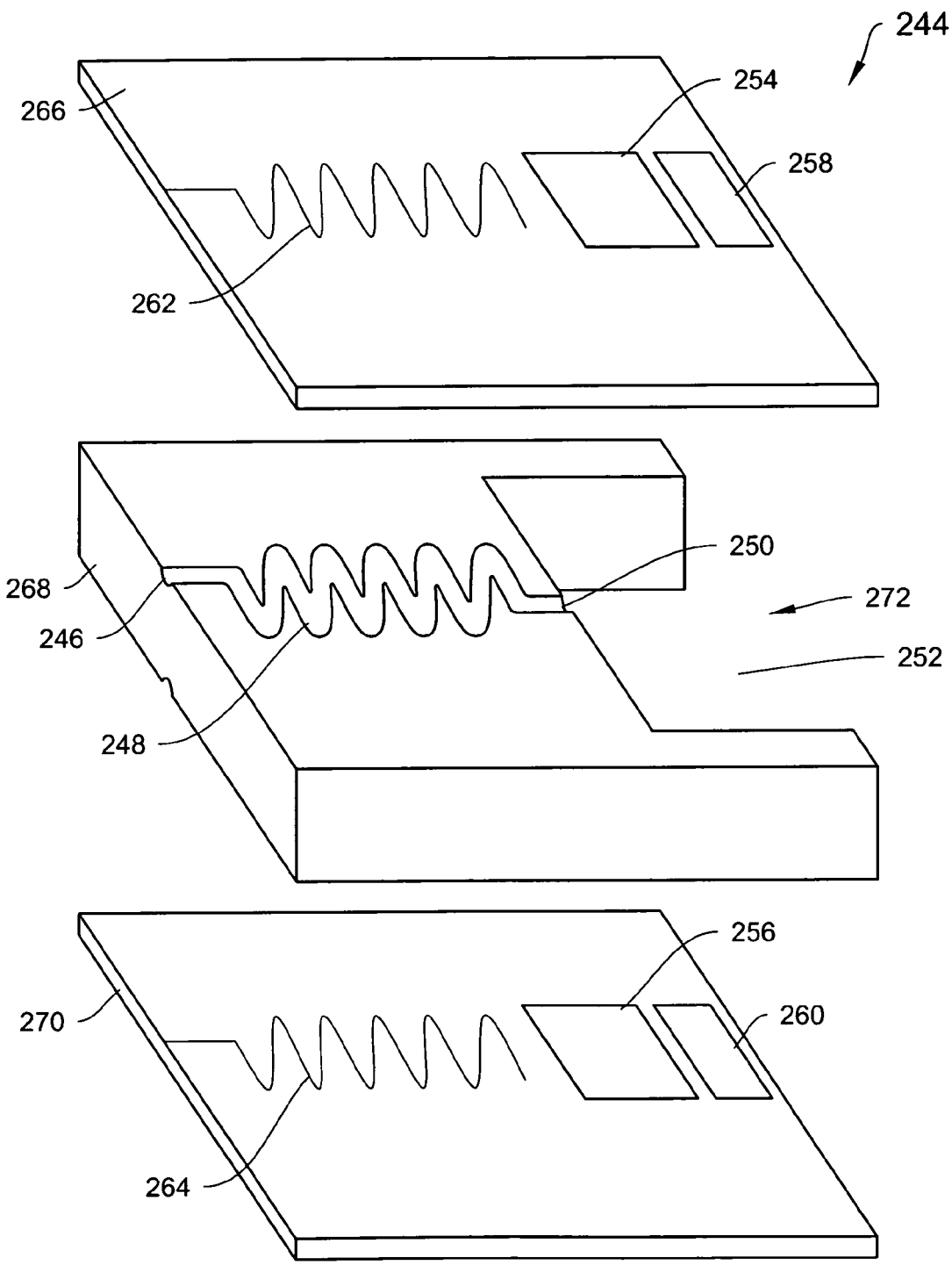
FIG. 17 is an exploded conceptual diagram of a GC-DMS system implemented on multiple layer substrates according to an illustrative embodiment of the invention.

FIG. 17 is an exploded conceptual diagram of a GC-DMS system 244 implemented on multiple layers of substrates according to an illustrative embodiment of the invention. The GC-DMS system 244 included GC inlet 246, GC column 248, DMS analyzer inlet 250, DMS analyzer 252, DMS filter electrodes 254 and 256, DMS detector electrodes 258 and 260, upper heater coil 262, lower heater coil 264, upper substrate 266, GC-DMS substrate 268, and lower substrate 270. The upper substrate 266 and the lower substrate 270 may be made, for example, of Pyrex™ glass or any other suitable insulating material. The GC-DMS substrate 268 may be made, for example, of silicon or any other suitable material.

In operation, a sample S is introduced into the GC inlet 246 and traverses the GC column 2248. The GC column 248 may be heated by heater coils 262 and 264 to enhance the GC elution process. Due to the GC process, constituent compounds become separated in time and arrive at the DMS analyzer inlet 250 at different times. A makeup drift gas may be introduced into the DMS analyzer 252 and combined with a sample S constituent in the DMS analyzer 252 to establish the required gas flow for the DMS analyzer 252. The DMS filter electrodes 254 and 256 apply a field voltage and field compensation voltage to enable sample S constituent filtering. The DMS detector electrodes 258 and 260 measure the ion intensity of the filtered constituent ion species of the sample S. After the sample is analyzed, it is exhausted from the DMS analyzer 252 through the DMS analyzer outlet 272.

By embedding various components of the GC-DMS system 244 in various substrates, e.g., substrates 266, 268, and 270, the GC-DMS system 244 may be manufactured and assembled in a cost efficient manner. Furthermore, different materials may be used at different substrate layers depending on an embedded component's purpose. For example, the substrates 266 and 268 may be made of Pyrex™ glass, or other suitable material, to accommodate the generation of thermal energy by heater coils 262 and 264 respectively.

Figure 18:
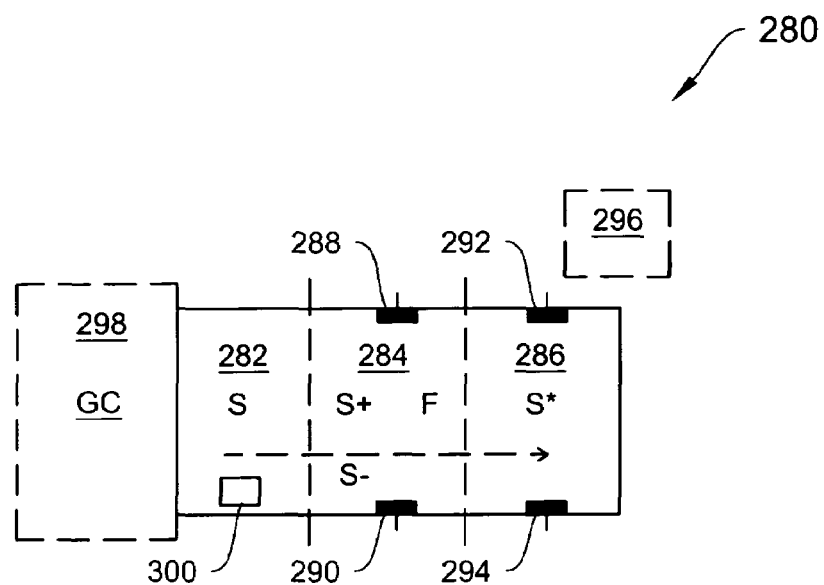
FIG. 18 is a conceptual diagram of a GC-DMS system according to an illustrative embodiment of the invention.

The GC-DMS systems previously described may be micro-fabricated as micro-electro-mechanical-machines (MEMS) from silicon using conventional micromachining technology to create an ultra-compact form factor. The GC-DMS can be formed by embossing a polymer material with the desired column structure and can be selectively functionalized by the stationary phase. The form-factor of the illustrative compact and/or ultra compact GC-DMS of the invention is about 1 to about 2 $cm^3$. The nominal power consumption of an illustrative compact GC-DMS is about 10 W, 5 W, 3 W, 1 W, or 100 mW. The microheaters, such as heaters 262 and 264 of FIG. 18, are be resistive film heaters mounted on the substrate adjacent to a GC column or mounted on the GC column substrate itself. The illustrative heaters have a form factor of about 380 (h)×50 (w)×3000 micrometers. The flow rate with the GC column of the above compact GC-DMS system is about 2 ml/min, 1 ml/min, or 0.5 ml/min, or less. The various components of the previously described compact GC-DMS systems may be embedded on one or more substrates or into one or more chips The components may also be embedded in an integrated circuit (IC), circuit board, and/or electronic assembly. The circuit board may be from ceramic, LCP, Teflon FR-4, silicon, other semiconductor materials, nano-machined materials.

One phenomenon that can occur with DMS, IMS and like analyzers that rely on atmospheric pressure chemical ionization is that they may become saturated as the concentration of a sample increases. In some instances, this saturation occurs because there are a limited number of reactant ions or because an ionization source is only capable of ionizing a limited amount of sample molecules. As the sample concentration is increases beyond the ionization capacity of an analyzer, a growing number of the sample molecules do not become ionized. Because ion mobility based analyzers, such as DMS analyzers, measure the amount of ions of a sample, if only a portion of the sample is ionized, only a portion of the actual sample concentration is detected and/or measured. Detector saturation can cause a measured intensity characteristic for a sample to become non-linear.

According to another feature, the invention corrects for non-linearities due to detector saturation in ion mobility based analyzers. According to one illustrative embodiment, the invention corrects for the non-linearities by applying linearization techniques to predict an actual sample concentration from a measured sample concentration. One linearization approach of the invention includes mathematically characterizing the measured detection signal of a sample at a low sample concentration where the analyzer is not saturated, and then using that mathematical characterization and/or algorithm to predict the actual sample concentration when the analyzer becomes saturated at higher sample concentrations.

In certain instances, a sample can be introduced into an analyzer, such as a DMS or IMS, in a predictable and/or controlled manner from another system. For example, a GC may be employed for separating constituents of a sample and delivering each constituent to DMS analyzer at a predictable time and in a predictable form. Due to the nature of the elution process in a GC, a sample constituent is generally delivered from a GC column in a concentration distribution, or pulse with respect to time, that can be mathematically characterized as Gaussian in form. By measuring a sample at a certain concentration, the Gaussian pulse can be defined mathematically by a standard Gaussian algorithm. However, certain constants and/or variables, i.e., parameters, of the algorithm may be adjusted to fit the Gaussian curve model to the measured detection signal. At a low sample concentration, the measured and/or detected sample concentration is likely representative of the actual sample concentration. Thus, the Gaussian curve is likely an accurate representation of the actual sample Gaussian pulse distribution.

Because the sample Gaussian pulse should retain the same form and proportions regardless of the sample concentration, the mathematically-defined Gaussian pulse at one sample concentration may be used to correct a detected signal with a deviated Gaussian pulse form when an analyzer becomes saturated. Thus, a calibration factor or function may be defined, based on the defined Gaussian pulse distribution at one sample concentration, that may then enable linearization of the non-linear detection response of an analyzer.

FIG. 18 is a conceptual diagram of a GC-DMS system 280 according to an illustrative embodiment of the invention. The GC-DMS system 280 includes input section 282, filter section 284, detection section 286, filter electrodes 288 and 290, detector electrodes 292 and 294, controller 296, and GC 298.

In operation, the input section 282 receives a sample S from the GC 298 or another source such as the surrounding atmosphere. The GC 298 employs an elution process to separate constituents of the sample S that arrive at predictable times at the input section 282 for analysis. The input section 282 may include an ionization source 300 that ionizes at least a portion of the sample S. The sample ions $S^+$ and $S^-$ are then filtered in the filter section 284 by filter electrodes 284 and 290. An RF field voltage and field compensation voltage may be applied between filter electrodes 288 and 290 to selectively filter an ion species of the sample S such as S*.

The selected ion species S* is then be detected in the detection region 286 by detector electrodes 292 and 294. The detectors electrodes 292 and 294 may be biased such that both positive and negative ion species of the sample S are detected concurrently. Alternatively, the selected and/or filtered ion species S* may be delivered to another analyzer such as a IMS, MS, or the like. The controller 296 may include a processor and other electronic circuitry to control the field voltage and field compensation voltage applied to the filter electrodes 288 and 290. The controller 296 may also include software to interpret the measured data from the detectors 292 and 294 such a linearization programming to compensate for a non-linear detection signal from the detectors 292 and 294. Either a longitudinal field, ionic flow generator, or transport gas may be employed to propel ions at the required velocity through the DMS sections of the GC-DMS system 280.

As stated previously, the sensor and/or analyzer response at low sample concentrations is approximately proportional to the actual sample concentration, e.g., the sensor response is linear. However, at higher sample concentrations, the sensor response becomes increasingly non-linear. The non-linear response at higher sample concentrations may occur due to sample oversupply, the limited ionization capability of an analyzer, the kinetic reaction rate of a sample, thermodynamic equilibrium or re-combination of ions with ions of an opposite charge, and other possible effects. The analyzer non-linear response introduces errors in the detected sample concentration, resulting in less accurate sample detection and measurement.

The sample concentration error may be corrected by a mathematical correction or response correction function derived from the relationship between the actual sample, e.g., analyte, concentration and the detected sample concentration. The mathematical correction may be determined empirically from experimental results where multiple known sample concentrations are measured in an analyzer. Then, an algorithm may be derived to define the relationship between the measured and actual sample concentration depending on the sample concentration and other parameters. The mathematical correction or response correction function may also be determined theoretically from models of the sample ion behavior or from a combination of empirical and theoretical data. The models may be based on, but not limited to, kinetics, thermodynamics, ion repulsion, ion attraction, and/or diffusion.

The parameters used for the mathematical correction or response correction function may include variables based on an analyzer's physical dimensions, RF voltage, flow rate, analyzer wall charging, transport gas composition, temperature, pressure, and chemical characteristics of the sample constituents. The parameters may be determined empirically by experimentation, theoretically by calculation, or both. The empirically-determined parameters may be determined prior to, during, or after sample analysis.

Figure 19:
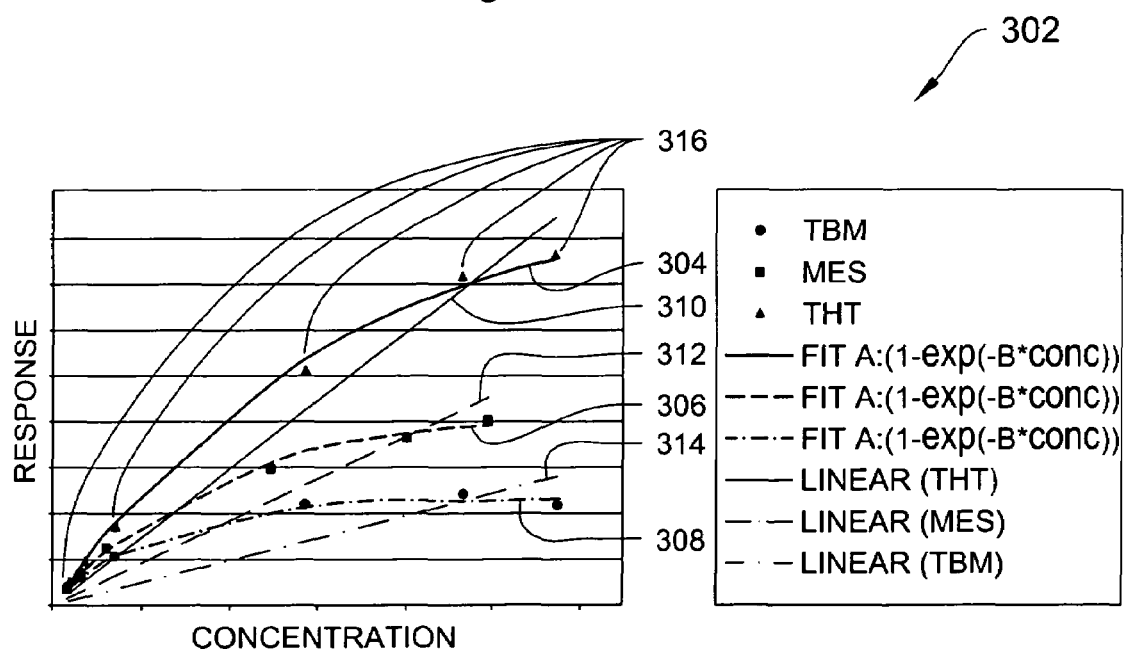
FIG. 19 is a graph of DMS detector response versus sample concentration for TBM, MES, and THT that shows the non-linear best-fit curve as compared with the linear plot for each sample respectively.

FIG. 19 is a graph 302 of a DMS analyzer response versus sample concentration for Tri Butyl Mercaptan (TBM), Methyl Ethyl Sulfide (MES), and TetraHydoThiophene (THT) showing the non-linear best-fit curves 304, 306, and 308 as compared with the linear plots 310, 312, and 314 for each sample respectively. The graph 302 illustrates the increasing non-linear response of a DMS analyzer as the concentration of a sample is increased. For the sample THT, a non-linear best fit curve 304 provides the most accurate plot of the analyzer response over the multiple plot points 316. In contrast, the THT linear plot 310 does not accurately reflect the THT sample concentration at the majority of the sample plot points 316. Thus, the non-linear best-fit characterization of the analyzer response provides a more accurate description of the measured analyzer detection signal at a particular sample concentration.

Conventionally, a non-linear response curve, e.g., plot 304, is determined by introducing a set of known sample concentrations into an analyzer and measuring the response detection signal for each sample concentration. For example, the plot 304 may be derived from the plot points 316 that correspond to multiple known THT sample concentrations introduced into an analyzer. The response curve of plot 304 may then be mathematically characterized by an algorithm that defines the response curve.

Because the response curve is expected to have a particular functional form that depends on a set of parameters, these parameters can be defined by fitting the function to these data points, e.g., sample plot points 316. The fitting procedure may be based on a conventional least squares minimization routine or an optimization routine which may be implemented in software or hardware, for example, in the controller 296 of FIG. 19. Once the analyzer response is characterized for a set of known sample concentrations, a function can be derived to extrapolate the actual sample concentration from a subsequently detected or measured sample concentration.

In certain illustrative embodiments of the invention, the above linearization procedure may be avoided and/or improved upon where an ion mobility based analyzer is used in combination with a source that provides a sample having a predictable concentration distribution. One such source, for example, is a GC that, through the elution process, can provide a sample having a consistent and/or predictable time-dependent concentration distribution to an analyzer. In a GC, a sample injection at the GC column input results in a sample constituent concentration peak at the column output where the peak has a varying concentration profile. Due, in part, to the random nature of molecular motion, this time-dependent concentration profile is often Gaussian or convoluted Gaussian in form. However, depending on the nature of the sample source, other sample concentration distribution profiles may be characterized and used to enable linearization of an analyzer.

The Gaussian distribution profile of a sample concentration peak from a GC can be measured by an analyzer, e.g., a DMS analyzer, at a particular sample concentration to characterize the Gaussian distribution profile for any other sample concentration. Thus, the Gaussian distribution profile may be used to correct the detected and/or measured non-linear ion intensity peak from a saturated analyzer.

Figure 20:
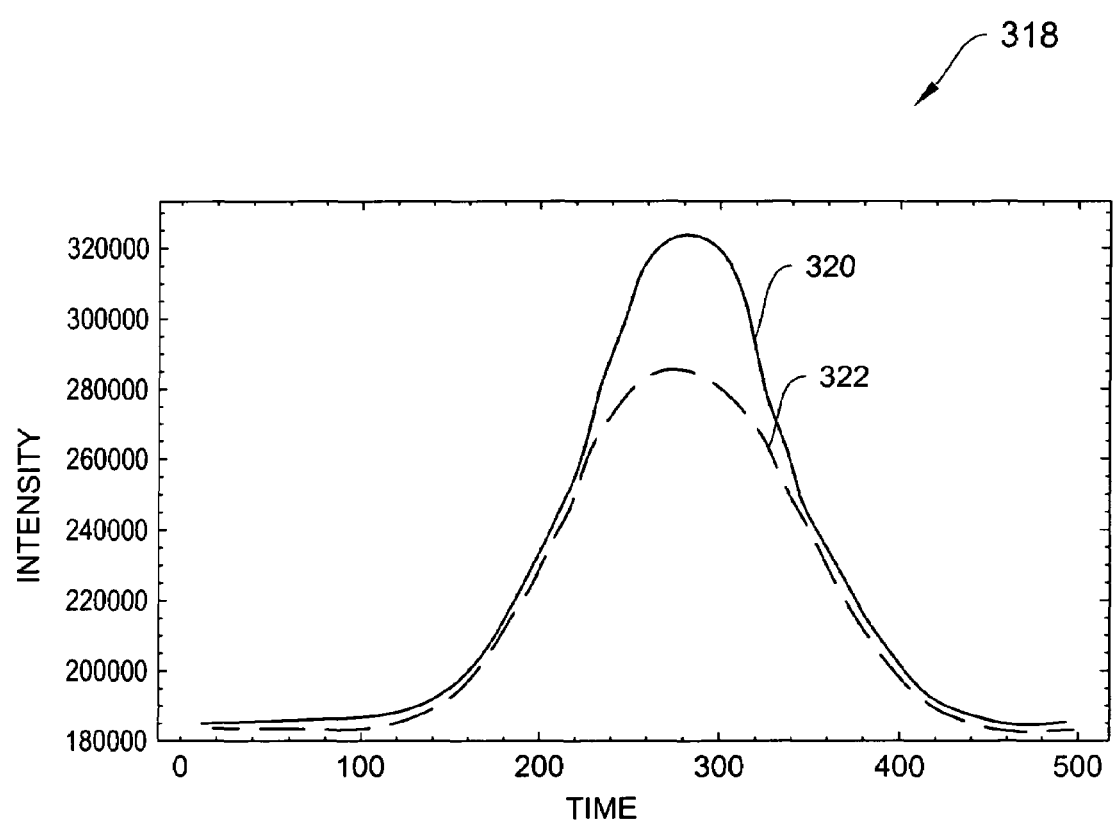
FIG. 20 is a graph of concentration versus time that illustrates the relationship between the actual Gaussian sample concentration with the detected Gaussian sample concentration due to detector saturation.

FIG. 20 is a graph 318 of sample concentration versus time that illustrates the relationship between the actual Gaussian sample concentration and the detected Gaussian sample concentration due to analyzer saturation. The plot 320 shows the typical Gaussian concentration profile of a sample pulse eluted from a GC column. The plot 322 shows the non-linear detection signal response to the concentration profile of plot 320 from an analyzer that is at least partially saturated. More particularly, the high sample concentrations in the middle of the graph 318 result in a damped, non-linear detection response at the higher concentrations. A comparison of the plot 320 with the plot 322 illustrates how analyzer saturation introduces errors in the detected sample concentration, resulting in less accurate sample detection and measurement.

In one illustrative embodiment, the invention extrapolates the actual sample concentration, as depicted in plot 320, from the detected sample concentration, as depicted in plot 322. To extrapolate the actual sample concentration from the detected non-linear sample concentration, the invention derives a response function from a single sample introduction and/or injection. This response function may then be applied to any subsequent analyzer response to convert the detected sample concentration into the accurate sample concentration.

The invention, according to one approach, derives the analyzer response function based on the assumption that a sample pulse has a known concentration distribution profile. For example, a sample pulse eluted from a GC has a Gaussian distribution profile. By observing the actual sample concentration distribution profile of a single eluted constituent peak, the invention determines the parameters of the response correction function by requiring that the response function transform the concentration distribution profile into the detected or measured analyzer response.

A generic response and/or response correction function is determine may be determined by experimentation, theoretical analysis, and/or both techniques in combination. The generic response correction function provides a mathematical description of an analyzer's response curve with parameters, e.g., variables, that enable the generic response correction function to be modified and/or adjusted to match, e.g., best fit, the measured analyzer response. Equation 1 is an example of a generic response correction function, while Equation 6 is an example of a response correction function including specific parameter values that enable the function to generate a response curve that matches or best fits to the measured curve of a particular analyzer.

Again, an illustrative non-linear analyzer generic response correction function may be expressed by the invention as follows:

$$h = \eta(1 - e^{\frac{-c}{B}}) \quad (1)$$

where c is the sample concentration, h is the analyzer response, and η and B are experimentally-determined parameters.

In certain illustrative embodiments, the invention may invert Equation 1 to define a response correction function or an equation for linearizing the analyzer response as follows:

$$h_{revises} = B \log(1-Ah) \quad (2)$$

where η is replaced by 1/A for implementation simplicity.

Two additional examples of non-linear generic response correction function are expressed by the invention as follows:

$$h = \frac{1}{2}\left(A + c + k - \sqrt{(A+c+k)^2 - 4Ac}\right) \quad (3)$$

$$h = B\left(1 - \frac{A-c}{A - ce^{-D(A-c)}}\right) \quad (4)$$

If the concentration distribution profile is known exactly, the analyzer response correction function can be defined exactly without the need of formula parameters. If the concentration distribution profile can only be defined in a parameterized form, then the analyzer response correction function must be parameterized by the invention as illustrated in the above Equations 1-4. Again, the invention may deduce or derive the parameter values of a response correction function by observing the detected analyzer response and best fitting the response function to the observe response.

Figure 21A:
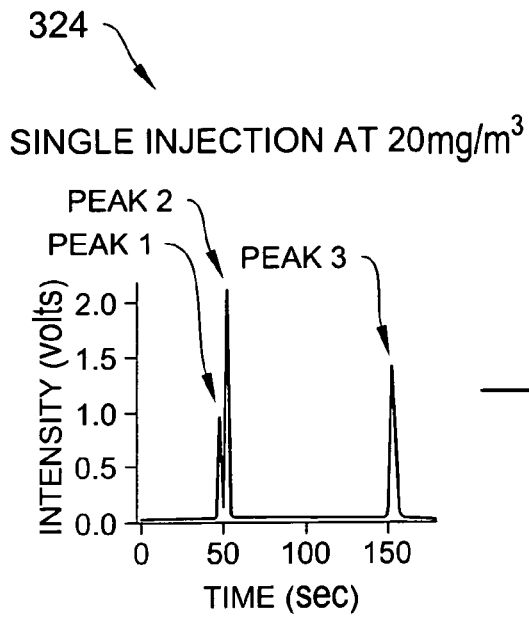
FIG. 21A is a GC-DMS chromatogram showing the ion intensity versus time for a single injection of 20 mg/m$^3$ of a mixed sample in a GC-DMS system that shows three ion intensity peaks.
Figure 21B:
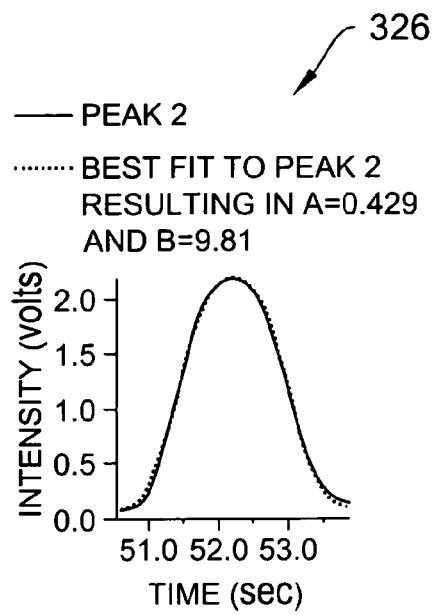
FIG. 21B is a graph providing an enlarged view of ion intensity versus time for the ion intensity peak 2 of FIG. 18A illustrating the Gaussian shape of the ion intensity peak 2.
Figure 22:
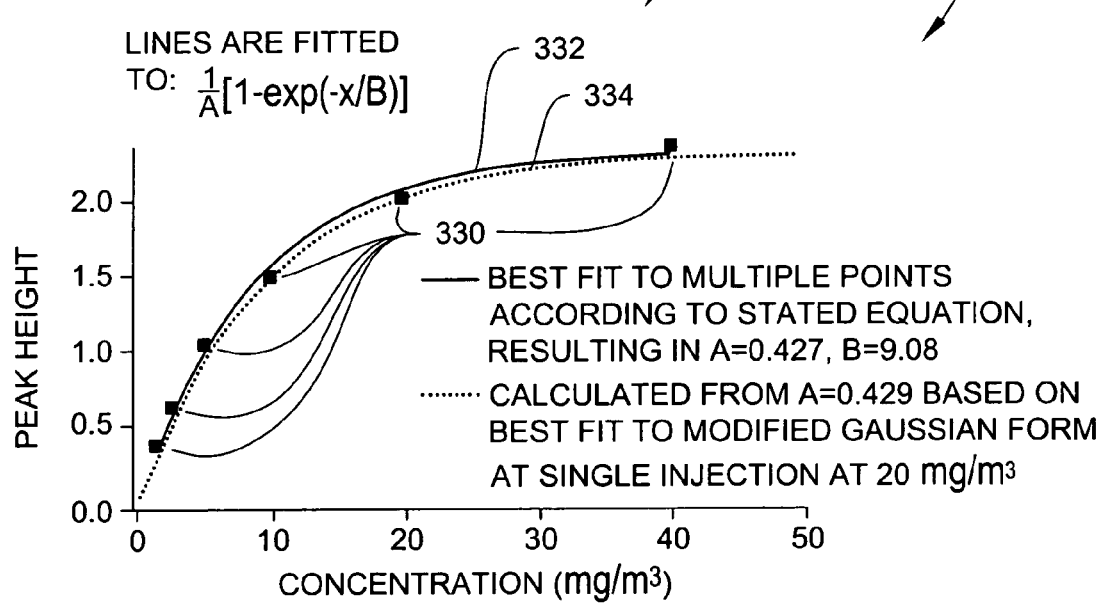
FIG. 22 is a graph of ion intensity peak height versus sample concentration comparing the best-fit curve derived from experimentally determined plot points with the calculated curve derived from a formula for predicting the actual Gaussian ion peak in the GC-DMS of the invention.

FIGS. 21A-22 are graphs illustrating a process of implementing a single-point calibration and/or linearization technique for a DMS coupled to a GC according to an illustrative embodiment of the invention. In this process, a single injection of 20 mg/m³ is used to determine the linearization response function to compensate for the non-linear response of a DMS analyzer.

FIG. 21A is a GC-DMS chromatogram 324 of the ion intensity versus time for a single injection of 20 mg/m³ of a sample in a GC-DMS system. The graph of FIG. 21A shows three ion intensity peaks, e.g., peaks 1, 2, and 3, each corresponding to a sample constituent eluted from a GC column at a particular time after introduction into a GC. FIG. 21B is a graph 326 providing an enlarged view of the observed and best-fit plots of ion intensity versus time for the ion intensity peak 2 of FIG. 21A. The graph of FIG. 21B illustrates the actual and predicted Gaussian shape of the ion intensity peak 2. To establish the best-fit Gaussian plot (dashed) that matches the observed Gaussian plot (solid), the invention deduces the parameter values A=0.429 and B=9.81. More particularly, the invention defines a Gaussian function with a Gaussian curve that matches the observed Gaussian plot or curve in FIG. 21B. Equation 5 describes the Gaussian shape as follows:

$$h = 1/A(1 - \exp[-Co/B(\exp(-(x-xo)^2/2\pi^2))]) \quad (5)$$

where
Co=20 mg/m³—initial injection amount
σ=standard deviation of for Gaussian peak width distribution
x=time seconds
xo=centroid of peak (in FIG. 22B, it's about 52.0 seconds)

Thus, from matching the theoretical and experimental curves, the parameter A and B values can be derived and/or determined.

The invention then processes the parameter A and B values per the analyzer response function to predict the analyzer response with respect to the sample concentration. For example, using the response correction function of Equation 1, the following equation is derived:

$$h = \frac{1}{0.429}\left(1 - e^{\frac{-c}{9.81}}\right) \quad (6)$$

where c is the sample concentration.

FIG. 22 is a graph 328 of ion intensity peak versus sample concentration. The graph 328 compares the best-fit curve 332 derived from the experimentally determined plot points 330 with the calculated and/or deduce curve 334 derived from the response function of Equation 6 according to an illustrative embodiment of the invention to predict the actual Gaussian ion peak. The conventional technique derives the best-fit curve from a best-fit of the plot points 330 using multiple injection experiments at different concentrations ranging from 1.25 to 40 mg/m³. This conventional technique uses a conventional least squares minimization routine or an optimization routine to derive the resulting parameter values of A=0.427 and B=9.08 to create the best-fit curve 332.

In contrast, the invention deduces the curve 334 based on a best fit to the observed Gaussian plot of graph 326 having A=0.429 and B=9.81. As shown in the graph 328, the deduced curve 334, which is based on parameters derived from a single-point calibration, matches closely with the best-fit curve 332, which is based on the multiple observed plot points 330. The margin of error between the two curves 332 and 334 is approximately 25% or less at certain concentrations, but may be further reduced by reducing uncertainties in the nominal sample concentrations.

An alternative exemplary process of implementing a single-point calibration and/or linearization technique for a DMS coupled to a GC is based on a thermodynamic model. In this model, the invention assumes that the analyzer saturation is due to a limited supply of electrons from an ionization source. In a thermodynamic model, equilibrium is established nearly immediately according to the following thermodynamic equation:

$$Rip^+ + S \overset{K}{\leftrightarrow} Rip + S^+ \quad (7)$$

t=0 abc0

At equilibrium a−y c−y b=y y $$k = \frac{(b+y)y}{(a-y)(c-y)} = \frac{by}{y^2 - (a+c)y + ac} \quad (8)$$

where K is the thermodynamic equilibrium constant, $Rip^+$ are the reactant ions, S are the sample molecules, Rip are the neutral reactant molecules, and $S^+$ are product ion species of the sample. Also, a is the concentration for the Rip ions, b is the concentration for initial sample, c is the concentration of the neutral reactant molecules, and y is the concentration for the resulting ion species of the sample. It is assumed that b is much greater than y.

Equation 7 shows that, at equilibrium, the concentrations for Rip+ and S are reduced proportional to an increase in the concentration of S+. Equation 8 shows that the thermodynamic equilibrium constant may be expressed by a combination of the concentrations of Equation 7.

By rearranging Equation 8 according to an illustrative embodiment of the invention, the following generic response correction function equations are derived:

$$y^2 - \left(a + c + \frac{b}{K}\right)y + ac = 0 \quad (9)$$

$$y^2 - (a + c + k')y + ac = 0 \quad (10)$$

$$y = 0.5[a + c + k' - [(a + c + k')^2 - 4ac]^{\frac{1}{2}}] \quad (11)$$

where k'=b/K, the best least square fit of this equation to a concentration profile of a single sample injection results in the parameters a and k', y is the height of the detected signal of the concentration profile, c is the actual height of the signal of the concentration profile without a saturation effect.

The invention can derive a and k' from a best least square fit of the curve derived from Equation 10 that matches the observed and/or detected concentration profile of an analyzer. Then, using the deduced a and k', the invention, in certain illustrative embodiment, may invert Equation 11 to obtain the equation for linearizing the analyzer detection response for subsequent sample analyses.

Thus, both of the above exemplary inventive processes enable conversion of a non-linear output signal of an ion mobility based analyzer to a linear output and/or response signal using a limited data set. The invention may implement the mathematical corrections of the exemplary processes either by using electronic circuits, software, firmware, and/or a processor in real-time at or near the time of sample detection or some time afterward.

Figure 23:
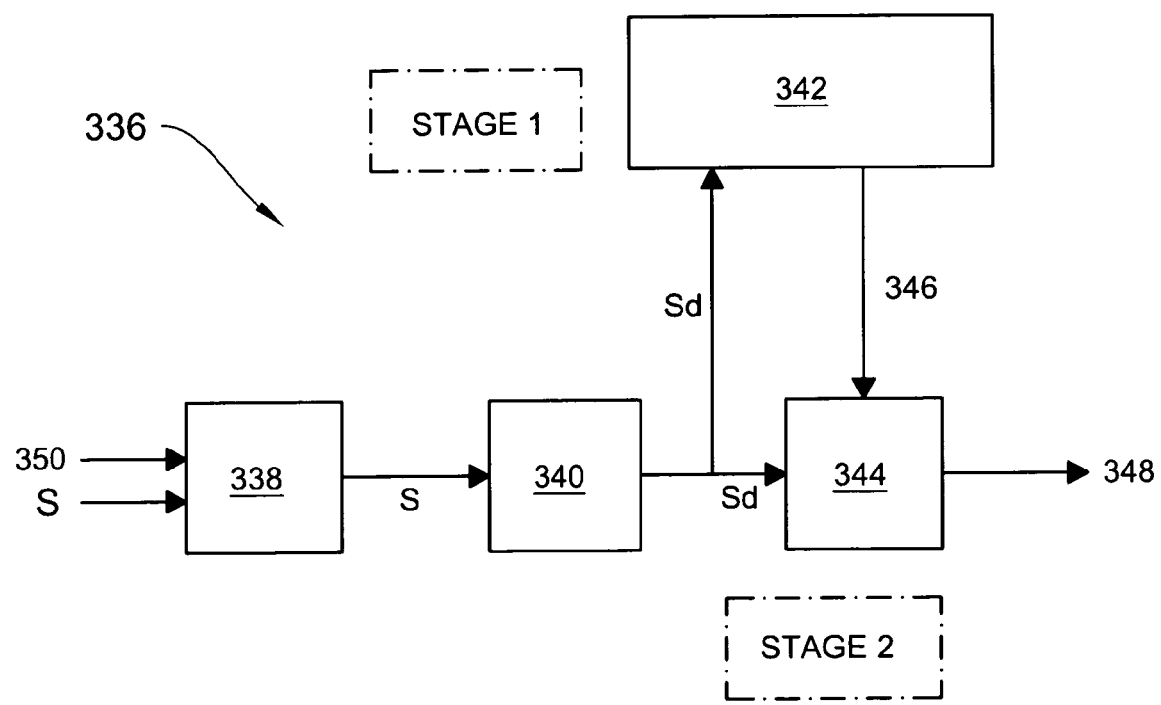
FIG. 23 is a conceptual block diagram of a GC-DMS system operating in two stages according to an illustrative embodiment of the invention.

FIG. 23 is a conceptual block diagram of a GC-DMS system 336 operating in two stages according to an illustrative embodiment of the invention. The GC-DMS system 336 includes GC 338, analyzer 340, optimizer/processor 342, functional linearizer 344, linearization function 346, sample input 350, and data output 348.

In the first stage, a non-linear profile for the analyzer 340 is determined and used to generate a correction function for linearizing the data output 348. In the second stage, the correction function is applied to the analyzer 340 output to linearize the data output 348.

In operation, the sample S is introduced into the GC 338 that delivers a predictable sample concentration distribution profile to the analyzer 340, e.g., a DMS analyzer. The analyzer 340 generates non-linear detection data Sd. The detection data Sd is based on the Gaussian distribution profile of the sample S from the GC. The detection data Sd is then delivered to the optimizer/processor 342 where the optimization parameters are extracted from the detection data Sd and an optimized linearization function 346 is generated.

In the second stage, the optimized linearization function 346 is applied to the non-linear data Sd in the functional linearizer 344. The detection data Sd is then linearized and outputted as data output 348. Because the optimization is based on the response data extracted form the analyzer 340, the detection data Sd reflects the non-linearities of the analyzer 340. Thus, the correction and/or linearization process is directed to the correction of non-linearities in the analyzer 340 and any subsequent detections by the analyzer 340, whether from the GC, the environment, or another source, can be linearized by application of the linearization function 346. A processor which may be included, for example, in controller 296 of FIG. 19 perform the functions of the first and second stages.

In certain illustrative embodiments, the invention includes a method of correcting detection data for an ion mobility based analyzer by first introducing a known sample concentration having a predictable time-dependent concentration distribution profile into an analyzer. Then, measuring the concentration for the known sample in the analyzer and generating a measured time-dependent concentration distribution profile for the known sample. Then, the invention processes the measured and predictable time-dependent concentration distribution profiles to determine a response correction function for the analyzer. Finally, the invention, in certain embodiments, employs the response correction function for the analyzer to correct subsequent detection data from analyzer.

Figure 24:
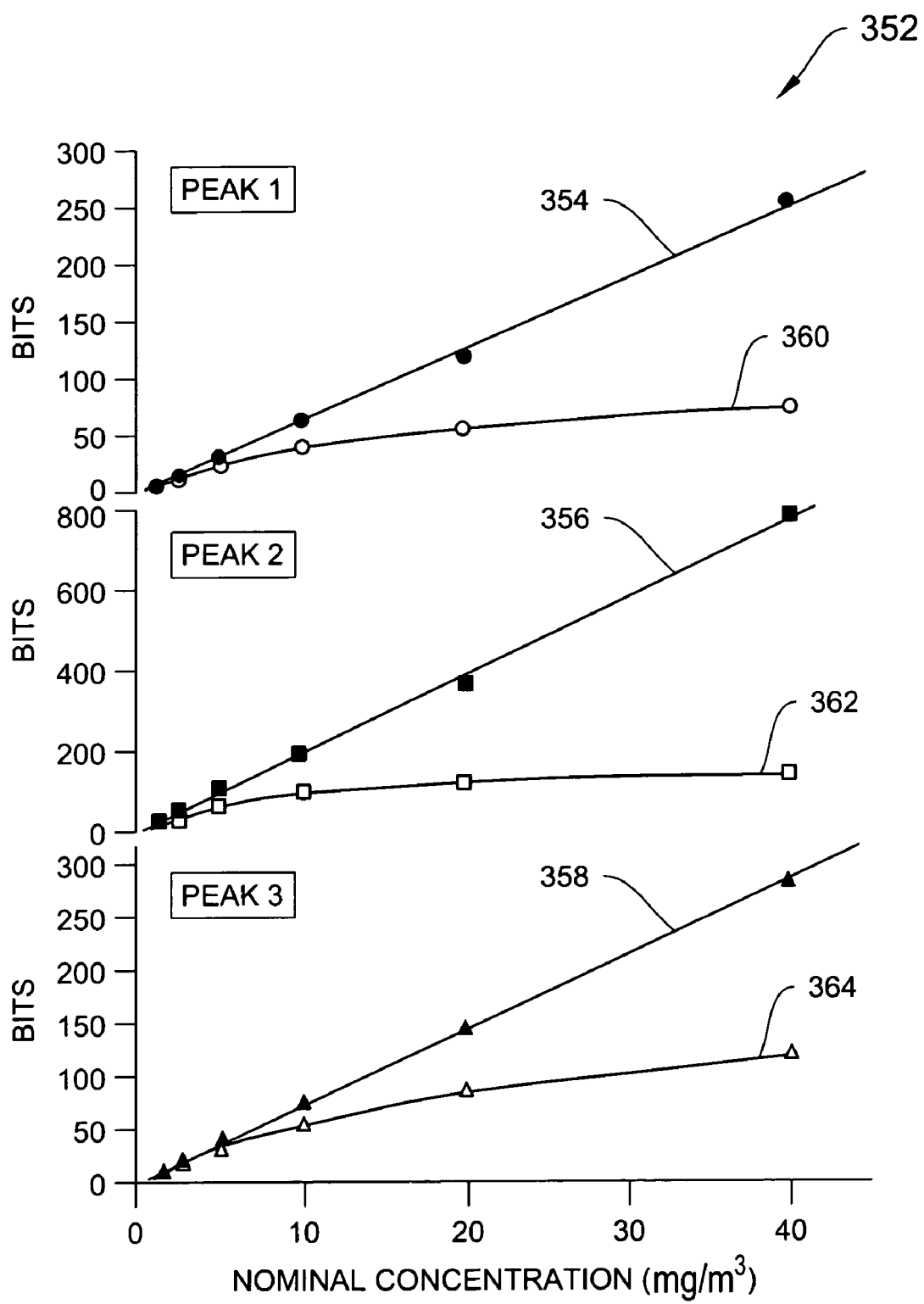
FIG. 24 is a graph of ion intensity peak versus nominal concentration for the ion intensity peaks 1, 2, and 3 of FIG. 17 illustrating the difference between the actual concentration and the detected concentration due to detector saturation according to an illustrative embodiment of the invention.

FIG. 24 is a graph 352 of the linearized and non-linear ion intensity peak versus nominal concentration for the ion intensity peaks 1, 2, and 3 of FIG. 20 that illustrates the difference between the actual concentration and the detected concentration due to detector saturation according to an illustrative embodiment of the invention. Based on the previously described linearization techniques, plots 354, 356, and 358 show the linearized or corrected analyzer response over a range of sample concentrations. The plots 360, 362, and 364 show the uncorrected non-linear analyzer responses. Furthermore, by comparing the plots of graph 352 with the plots of graph 302, the difference between the linearized plots 354, 356, and 358 and the linear plots 310, 312, and 314 are illustrated. The linearized plots 354, 356, and 358 provide a more accurate prediction of the actual sample concentration detected by an ion mobility based analyzer.

Figure 25:
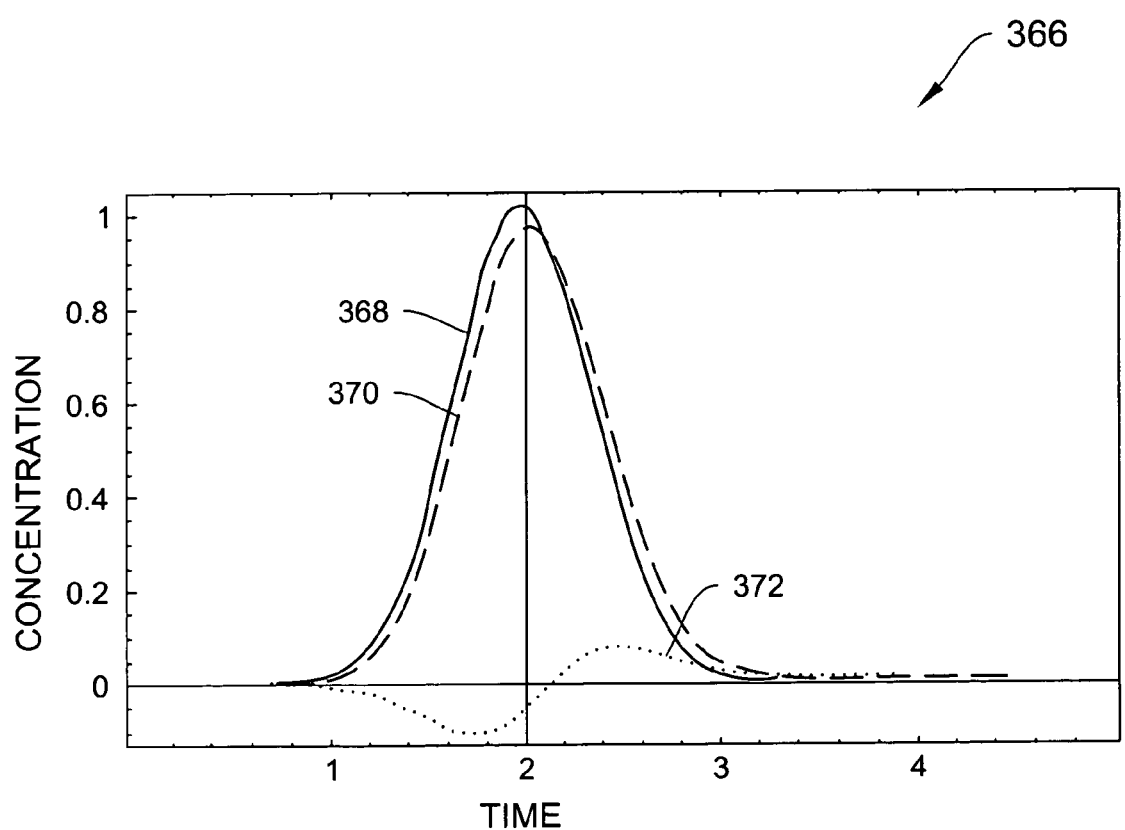
FIG. 25 is a graph of sample concentration versus time showing the effect of GC column tailing to produce non-Gaussian behavior of a pulse concentration.

FIG. 25 is a graph 366 of sample concentration versus time that shows the effect of GC column tailing on an analyzer response and the resulting non-Gaussian behavior of a pulse concentration. A GC may experience column tailing as shown by the plot 372. The column tailing in combination with the expected Gaussian distribution profile plot 368 may produce an offset Gaussian distribution profile from the GC column. The linearization parameters, however, may be adjusted to account for GC column tailing if necessary.

It should be understood that the above linearization techniques may be applied in a compact GC-DMS in a micromachined and/or discrete chipset form factor. The linearization functions may be performed in real-time or near real-time to produce orthogonal data for identification and accurate measurement of the concentration of a wide range chemical compounds.

Returning to FIG. 2A, the column temperature in a GC is preferably controlled to within tenths of a degree. The optimum column temperature is dependant upon the boiling point of the sample. If a sample has a wide boiling range, then temperature programming can be useful. The column temperature is increased (either continuously or in steps) as separation proceeds.

According to an illustrative embodiment of the invention, the controller 10c coordinates control of the temperature of the GC column 12 with the particular filter conditions being applied to the DMS 10b. More particularly, the controller 10c coordinates the temperature of the GC column 12 with one or more of Vcomp, Vrf, filter region temperature, filter region pressure, filter region humidity, filter region doping, and filter region flow rate/flow volume. For example, the controller 10c may sweep Vcomp for a particular Vrf and a particular GC column temperature. Also, the controller 10c may sweep Vcomp at a particular Vrf for a plurality of GC column temperatures. In other embodiments, the controller 10c may set one or more Vcomp, Vrf value pairs for each of a plurality GC column temperatures.

As shown in FIG. 2A, according to the illustrative embodiment, the GC-DMS 10 may include one or more heating/cooling elements 15 for regulating the temperature of the GC column 12. In one implementation, the controller 10c ramps the temperature of the GC column 12 between about −60 degrees C. and about 400 degrees C. In other implementations, the controller 10c ramps the temperature of the GC column 12 between about 20 degrees C. and about 250 degrees C. According to alternative implementations, the controller 10c steps the temperature of the GC column 12 incrementally between the temperatures of the above or other ranges. All of the above is collectively referred to herein as varying the temperature of the GC column 12.

The advantages of the invention will now be discussed with respect FIGS. 26A-29B. More particularly, FIG. 26A is a graph 400 of temperature versus time for a GC operating under isothermal conditions. FIG. 26B is a graph 402 of intensity versus time for a mixed sample eluted from a GC operating under isothermal conditions. As shown in FIG. 26B, the intensity peaks become wider as time progresses and heavier sample components are eluted and detected from the GC column. The wide nature of the peaks also tends to reduce the resolution of the GC because, for example, the wider peaks may tend to overlap as time progresses.

FIG. 27A is a graph 404 of temperature versus time in a GC column where the temperature is ramped/varied in an increasing and/or decreasing manner. FIG. 27B is a graph 406 of intensity versus time of a mixed sample eluted from a GC column where the GC column temperature is ramped/varied according to FIG. 27A. As illustrated by FIG. 27B, the increasing and/or ramping of temperature causes components of the sample to be eluted in a more rapid manner. This in turn causes the peaks to be narrower. Thus, varying the temperature causes the GC to analyze a sample more rapidly relative to the isothermal example.

Also, when the intensity peaks are narrowed by higher GC column temperatures, the resolution of heavier sample components is improved by avoiding peak overlap. Further, by increasing the speed of elution and narrowing the peaks, a wider range of compounds can be analyzed over a particular period of time. Due to the small sized of the GC column of the invention, heating and cooling of the GC column may be achieved with less than about 10 W, 5 W, 3 W, 2 W, 1 W, 500 mW, or 250 mW of power.

FIG. 28A is a graph 408 of temperature versus time in a GC column where the temperature is ramped and/or stepped over a range of temperatures either in an increasing or decreasing manner. FIG. 28B is a graph 410 of intensity versus time of a mixed sample eluted from a GC column where the temperature is ramped and/or varied according to FIG. 28A. At various times, the temperature remains constant while at other times the temperature is varied, possibly at different rates. In some embodiments, the temperature is relatively higher at later times to narrow the later elution peaks associated with heavier sample components. The temperature may be maintained at particular temperatures for particular periods of time to reduce power consumption and/or allow for more predictable separation of sample components. A DMS analyzer may filter the output from the GC column at various field conditions to improve sample component detection and/or identification. The purpose of controlling the GC temperature is to enhance chromatographic separation of compounds and to overall increase the separation and identification of analytes. In some embodiments the GC and DMS temperatures may be controlled in a linked way, that is that as the GC temperature is ramped so is the DMS temperature. The GC and DMS may have the same temperatures or may be ramped at different rates or may be ramped at the same rate but from different starting or ending temperature setpoints.

In another embodiment, the GC temperature may be ramped, and the DMS temperature stepped from a low temperature setting to a second temperature setting when the GC temperature reaches a certain level. The advantage of ramping both the GC and DMS is that for light molecules the GC does not need to be heated very much and these light molecules tend not to be very sticky and so pass through the DMS easily. As the molecules become heavier, they require higher temperatures to go through the GC, they also tend to be stickier molecules so increasing the DMS temperatures for these molecules helps remove them from the DMS and limit any carryover and memory effects. Thus synchronizing GC and DMS temperatures may be highly beneficial for enhanced compound identification and detection of light and heavy molecules In addition to memory effects, the different temperatures may affect differential mobility differently, increasing the differential mobility for the heavy molecules, or fragmenting the heavy molecules and as such enhancing further compounds identification. The GC and DMS may be ramped over temperatures from 0-500 C for example.

Figure 29A:
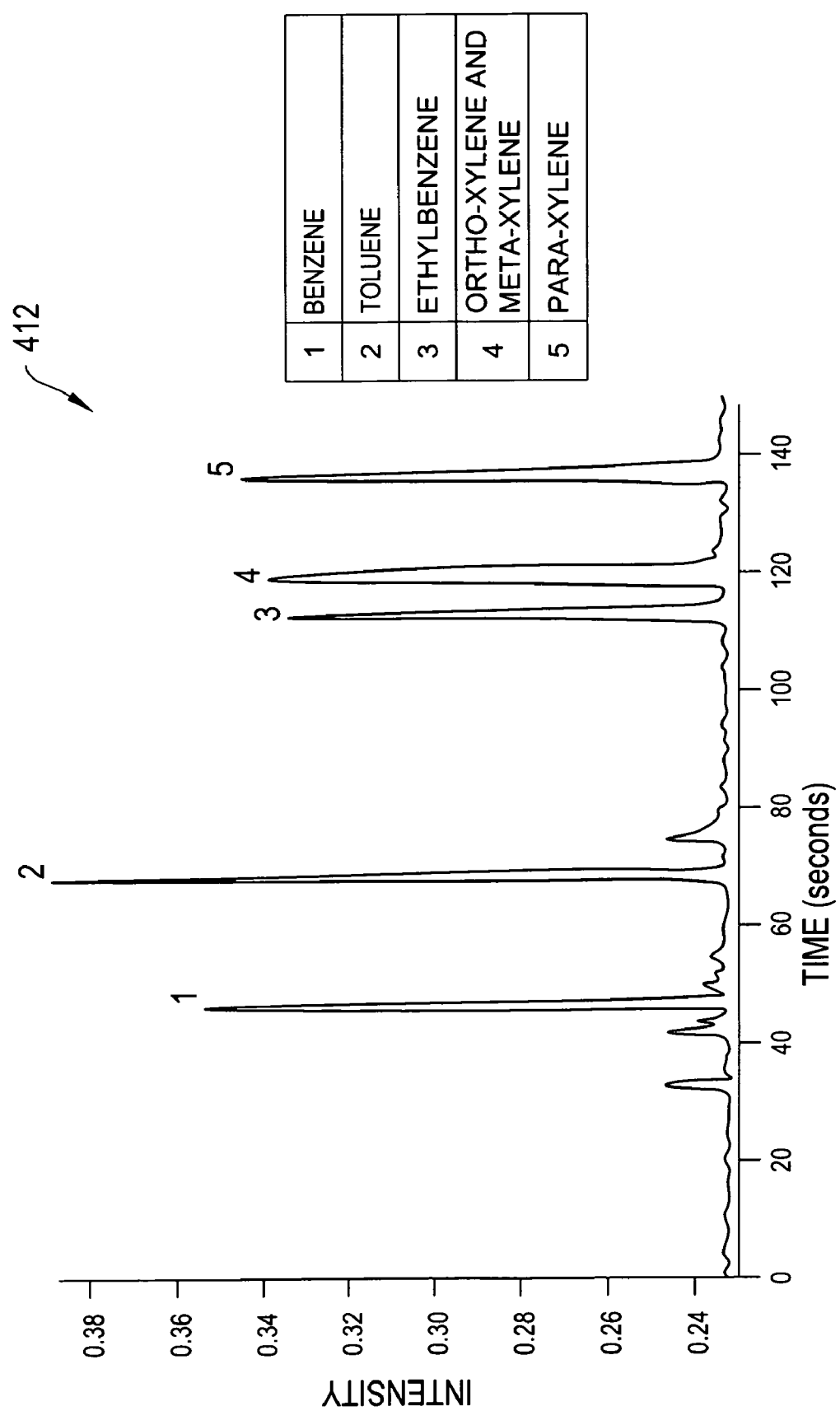
FIG. 29A is an exemplary graph of intensity versus time of a mixed sample including Benzene, Toluene, Ethylbenzene, ortho-Xylene and meta-Xylene, and para-Xylene, that are eluted from a compact GC column where the temperature is ramped and/or stepped over approximately a 150 second time period.

FIG. 29A is an exemplary graph 412 of intensity versus time of a mixed sample including Benzene, Toluene, Ethylbenzene, ortho-Xylene and meta-Xylene, and para-Xylene, that are eluted from a compact GC column where the temperature is ramped and/or stepped over approximately a 150 second time period. The intensity may be detected by a DMS analyzer at a particular compensation voltage. Alternatively, the intensity may be an average of multiple detections over a range of compensation voltages.

Figure 29B:
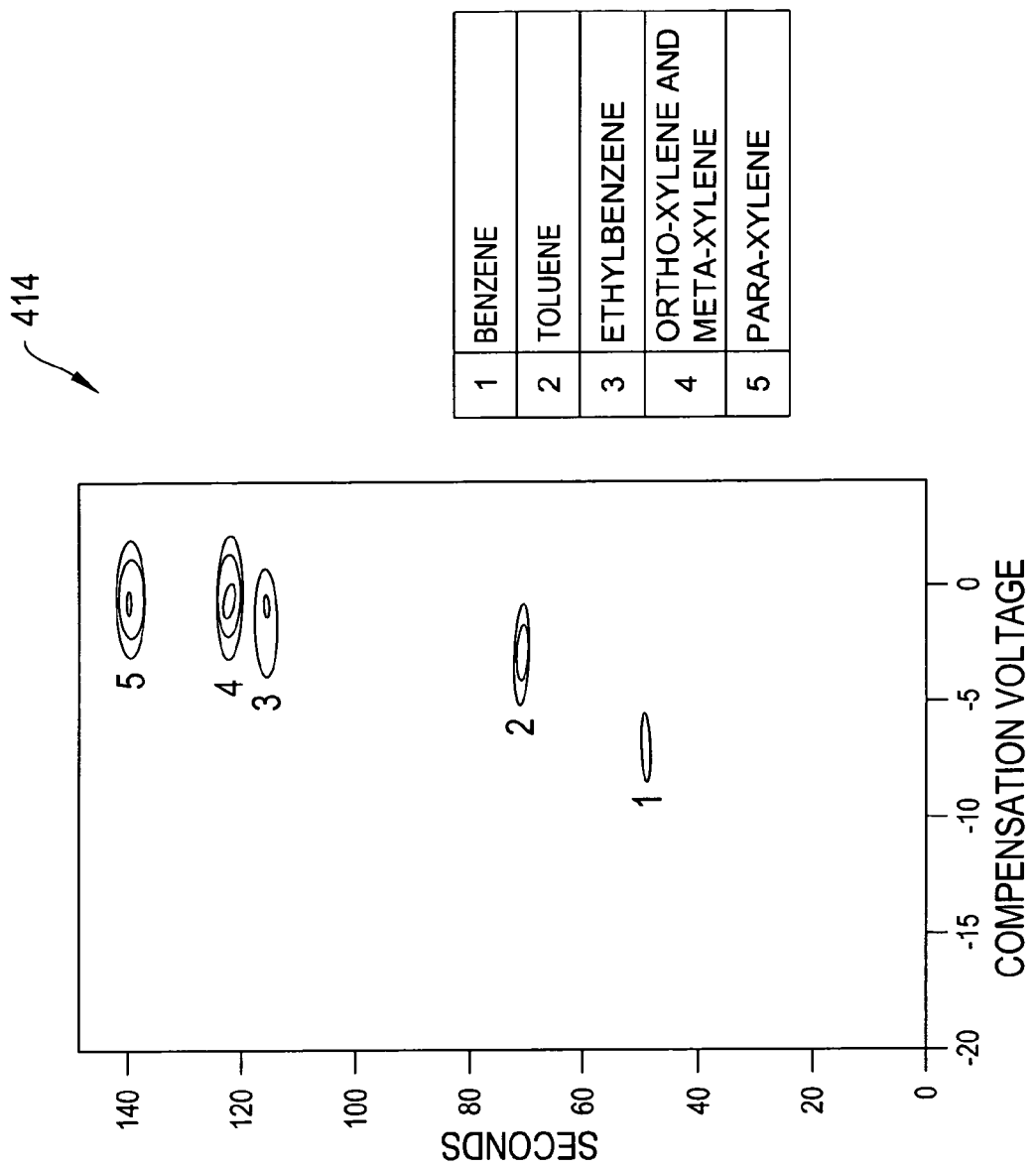
FIG. 29B is a three dimensional topographical plot and/or image of ion intensity over a range of GC column elution time versus DMS filter compensation voltage according to an illustrative embodiment of the invention.

FIG. 29B is a three dimensional topographical plot, dispersion plot, and/or image 414 of ion intensity over a range of GC column elution time versus DMS filter compensation voltage. The topological plot 414 provides a three dimensional representation corresponding to the two-dimensional representation of graph 412. The topographical plot 414 enhances sample component detection in a combined GC/DMS analyzer by combining the DMS detection at various field conditions with GC column elution separation at various temperatures over a period of time. Sample detection may be enhanced, for example, where two species are eluted at the same time but have different ion intensity peaks in relation to different compensation voltage settings. Thus, the plot 414 would enable the resolution of two species having the same GC column retention times but different ion mobility characteristics.

In one embodiment, the controller and/or a processor performs an analysis (collectively "analysis") using, for example: dispersion characteristics (2-, 3-, and n-dimensional) of the plot 414. The multi-dimensional representation of plot 414, according to one illustrative embodiment, is a three-dimensional dispersion plot, employing x- and y-spatial coordinates, with a z-coordinate being represented by a variation in color. It should be noted that although the above discussed dispersion plot 414 employ color changes to indicate intensity, changes in any color-related feature, such as changes in color saturation, gray scale or black and white (as shown as concentric rings at various ion intensity locations in plot 414) may be employed instead or in combination. Various illustrative comparison approaches may employ pattern matching using, for example, the above described three-dimensional dispersion plot 414 (or a two-dimensional version of the plot 414). However, in other illustrative embodiments, the information provided by the dispersion plots is stored in the library as mathematical relationships, and suitable conventional approaches for comparing such mathematical relationships may be employed to identify the unknown species.

A controller, such as the above described controller 10c, supplies the controlling electronic signals. The controller may be located on-board, or off-board, where the GC-DMS device 86 has at least the leads and contact pads for connecting to the control circuit (e.g., FIGS. 4 and 5). In one embodiment, the controller provides thermal management by interfacing with and/or employing electrically driven cooling and/or heating system to enhance detection of certain ion species.

Figure 29C:
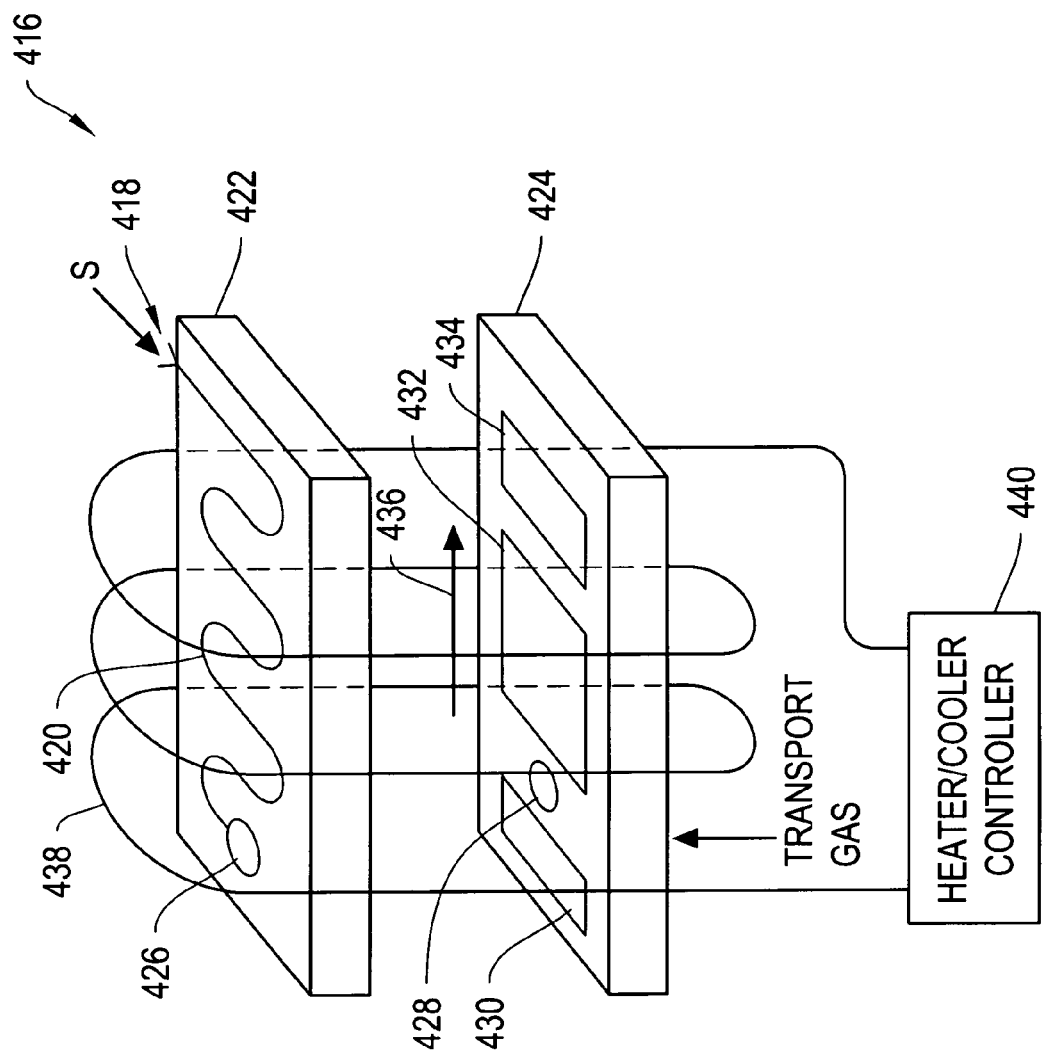
FIG. 29C is a conceptual diagram of a compact GC-DMS system including a surrounding heater element according to an illustrative embodiment of the invention.

FIG. 29C is a conceptual diagram of a compact GC-DMS system 416 including a surrounding heater element 438 according to an illustrative embodiment of the invention. The GC-DMS system 416 includes two substrates 422 and 424, a GC column 426, a GC column inlet 418, a heater/cooler element controller 440, a flow path 436, an ion source 430, a transport gas inlet 428, DMS filter electrode 432, and DMS detector 434. Although not shown, substrate 422 may include an ion source, DMS filter, and/or DMS detector electrodes that match and/or oppose the ion source 430, DMS filter 432, and DMS detector 434 electrodes respectively.

In operation, a sample S is introduced in the GC column 420 via the inlet 418. Due to the GC process, constituent compounds become separated in time with the GC column 420 and arrive at the GC outlet 426 at different times. The sample S constituents enter the flow path 436 and are carried by a transport gas, introduced at inlet 428, through a ion mobility based analyzer. The sample S constituents may be ionized by ion source 430 and then subjected to a time-varying and compensated field by DMS filter electrode 432. The ions that pass through the filter fields are then detected by detector electrode 434. In one embodiment, the heater/cooler controller 440 regulates the current flow through the heater element 438 to regulate the temperature within the GC column 420 and/or the flow path 436. In another embodiment, the heater/cooler element 438 may include a conduit capable of carrying a fluid and/or gas that exchanges thermal energy with its surrounding to effect heating and/or cooling of the GC column 420 and/or DMS flow path 436, and/or other elements of the system 416. In other embodiments, the DMS filter electrode 432 and/or other elements along the flow path 436 may generate heat, in response to the controller 440 regulating current flow to the element. In one embodiment, the controller 440 includes the controller 10c of FIG. 2A. In another embodiment, the heater/cooler element includes a coil and/or conduit, wrapped around the GC-DMS system 416 assembly that provides heating and/or cooling to the system 416. In certain embodiments, the GC column 420 temperature and the analyzer flow path 436 temperature are operated in an isothermal manner where the temperatures are regulated to about the same temperatures. In an alternative embodiment, the temperature within the GC column 420 is regulated and/or varied at a different temperature, rate, programmable sequence than in the DMS analyzer or in other GC columns that interact with the DMS analyzer.

Figure 29D:
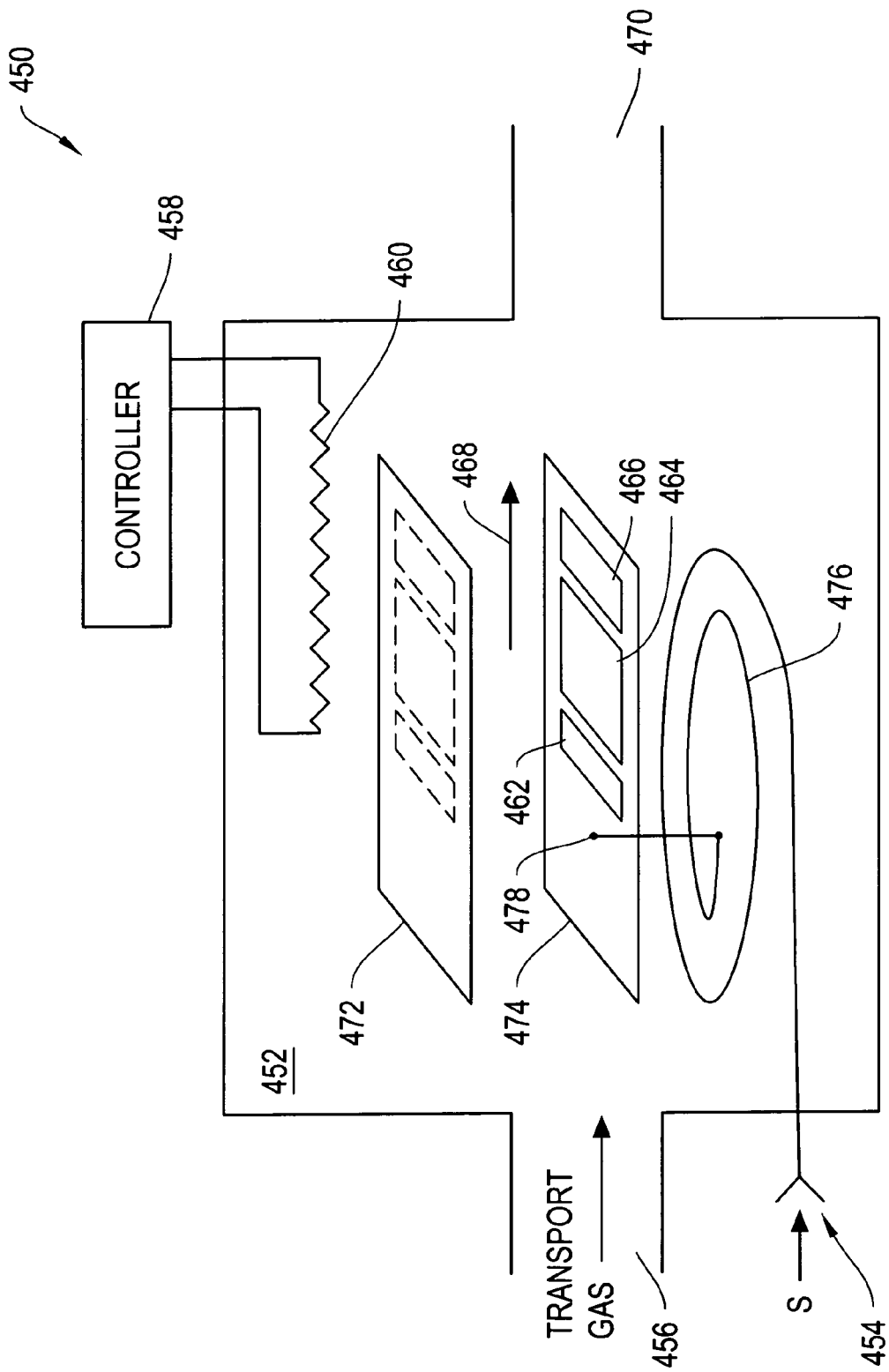
FIG. 29D is a conceptual diagram of a compact GC-DMS system mounted to a manifold including a heater element according to an illustrative embodiment of the invention.

FIG. 29D is a conceptual diagram of a compact GC-DMS system 450 mounted to (and/or embedded within) a manifold 452 including a heater element 460 according to an illustrative embodiment of the invention. The GC-DMS system 450 includes a transport gas inlet 456, a sample S inlet 454, a GC column 476, an outlet 470, a controller 458, a first substrate 472, a second substrate 474, a GC column outlet 478, an ion source 462, and DMS filter 464, a DMS detector 466, and a flow path 468 between the substrates 472 and 474.

Figure 29E:
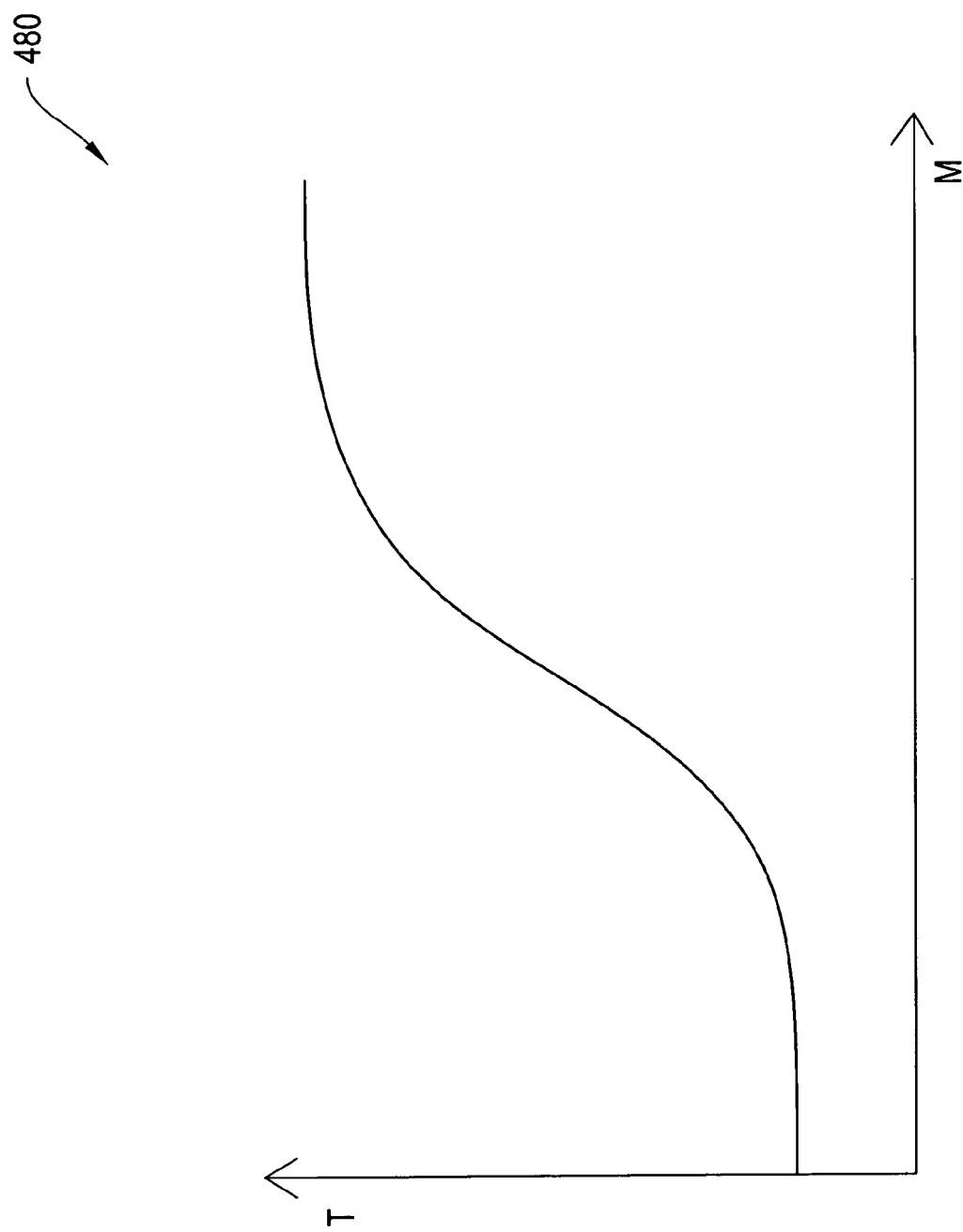
FIG. 29E is a plot of preferred temperature within a GC column and/or DMS versus species mass according to an illustrative embodiment of the invention.

In operation, a sample S is introduced in the GC column 476 via the inlet 454, Due to the GC process, constituent compounds become separated in time with the GC column 476 and arrive at the GC outlet 478 at different times. The sample S constituents enter the flow path 468 and are carried by a transport gas, introduced at inlet 456, through a ion mobility based analyzer. The sample S constituents may be ionized by ion source 462 and then subjected to a time-varying and compensated field by DMS filter electrodes 464. The ions that pass through the filter fields are then detected by detector electrodes 466. In one embodiment, the heater/cooler controller 458 regulates the current flow through the heater element 460 within the manifold 452 to regulate the temperature within the GC column 476 and/or the flow path 468. In another embodiment, the heater/cooler element 458 may include a conduit capable of carrying a fluid and/or gas that exchanges thermal energy with its surrounding to effect heating and/or cooling of the manifold 452, including the GC column 476 and/or DMS flow path 468, and/or other elements of the system 450. In other embodiments, the DMS filter electrodes 464 and/or other elements along the flow path 468 may generate heat, in response to the controller 458 regulating current flow to the element. In one embodiment, the controller 458 includes the controller 10c of FIG. 2A. In a further embodiment, FIG. 29E is a plot of preferred temperature within a GC column and/or DMS versus species mass according to an illustrative embodiment of the invention. In certain embodiments, the temperature within a GC-DMS system, such as systems 416 and 450, are controlled depending on the mass and/or weight of the ions that are being analyzed. Light sample constituents, e.g., molecules and/or ions, tend to travel and/or elute through a GC column at a faster rate than heavier constituents. The rate of propagation through a GC column can be increased by increasing the temperature within the GC column. Thus, for heavier sample constituents, the column temperature can be raised to reduce the column retention time and reduce the analysis time. For lighter sample constituents the GC column temperature can be reduced to improve the resolution of various light sample constituents. Thus, the GC column temperature may be controlled by a controller that varies the column temperature depending on the mass of the sample constituents that are desired to be detected. FIG. 29E illustrates the relationship of temperature versus mass where the temperature is preferably set relatively lower for lighter sample constituent and relatively higher for heavier sample constituents.

Figure 30:
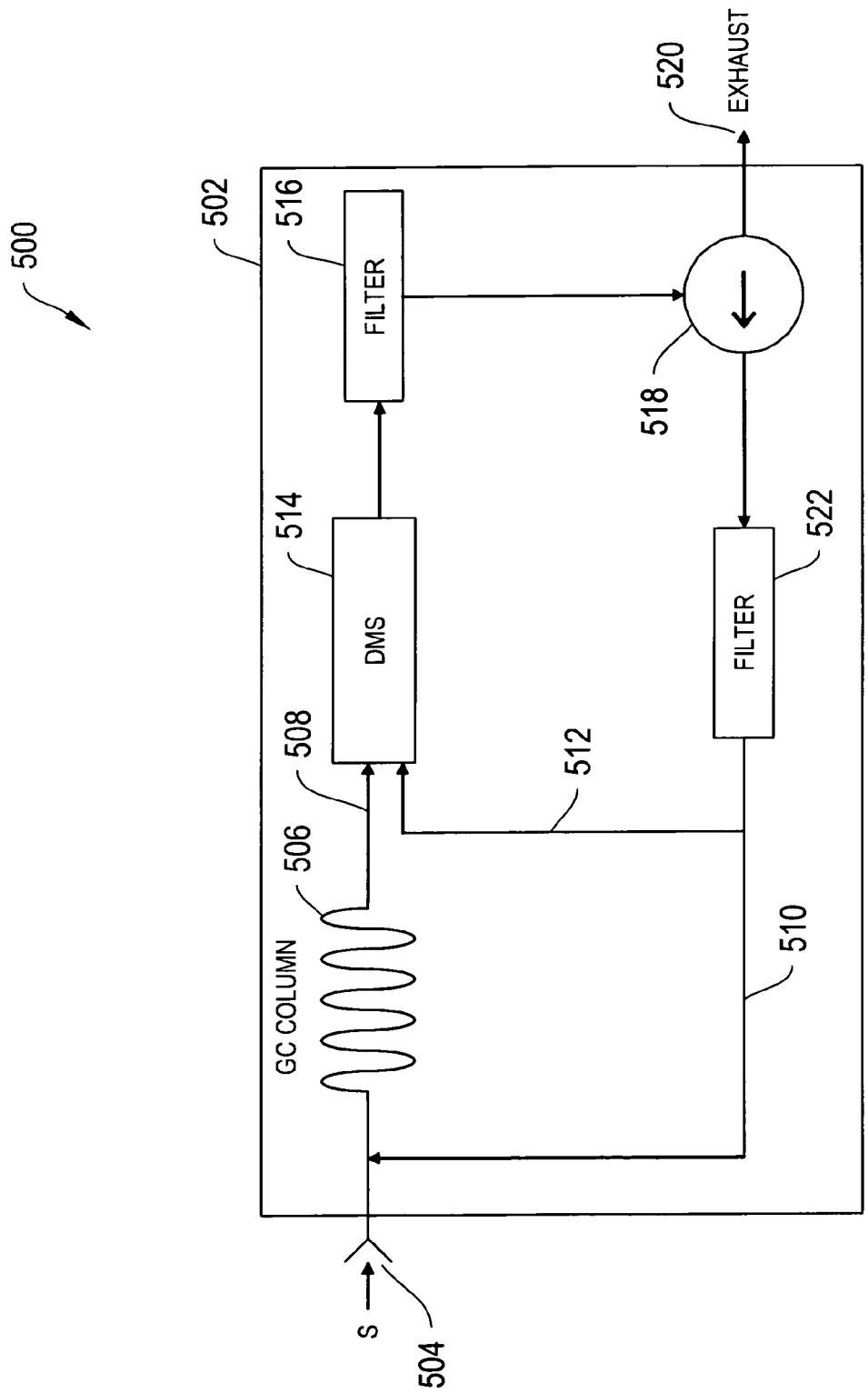
FIG. 30 is a conceptual diagram of a GC-DMS system including a first re-circulation flow path through the GC column and a second re-circulation flow path into the DMS according to an illustrative embodiment of the invention.

FIG. 30 is a conceptual diagram of a GC-DMS system 500 including a first recirculation flow path 510 through the GC column and a second recirculation flow path 512 into the DMS 514 according to an illustrative embodiment of the invention. The GC-DMS system 500 includes a sample S inlet 504, a GC column 506, a sample stream inlet flow path 508, a first filter 516, pump 518, exhaust 520, and a second filter 522. The filters 516 and 522 may include a molecular sieve filter and/or a carbon filter. One or more of the components of the GC-DMS system 500 may be embedded on or within a substrate 502. Although not shown, any flow path of the GC-DMS may include one or more orifices, valves, flow restrictors, and/or flow regulators to establish and/or control a selected flow rate within a flow path.

In operation, a sample S is introduced via the inlet 504 to the GC column 506. Due to the GC process, constituent compounds become separated in time and arrive at the DMS 514 at different times via the sample stream inlet flow path

508. A makeup drift gas is combined the sample S constituent via the flow path 512 at the inlet to the DMS 514 to establish the required gas flow for the DMS 514. In one embodiment, the recirculation flow path 512 merges with the flow path 508 at the inlet to the DMS 514.

The DMS 514 may include an ionization source, DMS filter, and detector that are employed to analyze the sample constituents as they pass through the DMS 514. The sample S may then be transported by a carrier gas to a filter 516, such as a molecular sieve, capable of removing unwanted components and/or impurities from the gas. A pump 518 then delivers the clean carrier gas to a second filter 522, such as a carbon filter, to further clean the carrier gas. A portion of the carrier gas is then directed via recirculation flow path 510 toward the entrance of the GC column 506 to facilitate sample S flow, from the inlet 504, through the GC column 506. In one embodiment, the flow rate through the GC column 506 is about 1-10 cc/min while the flow rate through the recirculation flow path 512 and DMS 514 is about 300 cc/min.

Unlike other GC-DMS systems where the amount of fluid entering the DMS via its sample stream inlet is equal to the amount of fluid removed and/or exhausted from the system, the GC-DMS system 500 provides a recirculation flow path 510 to the inlet of the GC column 506 which causes the amount of fluid entering the DMS 514 via the sample stream inlet flow path 508 to be greater than the amount of flow exiting the GC-DMS system 500 via the exhaust 520.

For example, if the sample inlet 504 flow rate is 1 cc/min and the flow rate of the recirculation flow path is 1 cc/min, the sample stream inlet flow path 508 flow rate is 2 cc/min into the DMS 514. If the second recirculation flow path 512 flow rate is 8 cc/min, the flow rate through the DMS 514 is 10 cc/min. By exhausting 1 cc/min via the exhaust 502, the flow rate exiting pump 518 is 9 cc/min. The 9 cc/min of fluid flow exiting the filter 522 can then be split into 1 cc/min of flow in recirculation flow path 510 and 8 cc/min of flow in recirculation flow path 512. Thus, the amount of fluid entering the DMS 514 via the sample stream inlet flow path 508, e.g., 2 cc/min, is different than the amount of fluid exhausted from the system 500 via exhaust 520, e.g., 1 cc/min. The forgoing flow rates are intended to be exemplary and may not represent the preferred flow rates of a GC-DMS system 500. For instance, the make up gas flow rate in the recirculation flow path 512 and DMS 514 may be about 300 cc/min in certain embodiments.

Figure 31A:
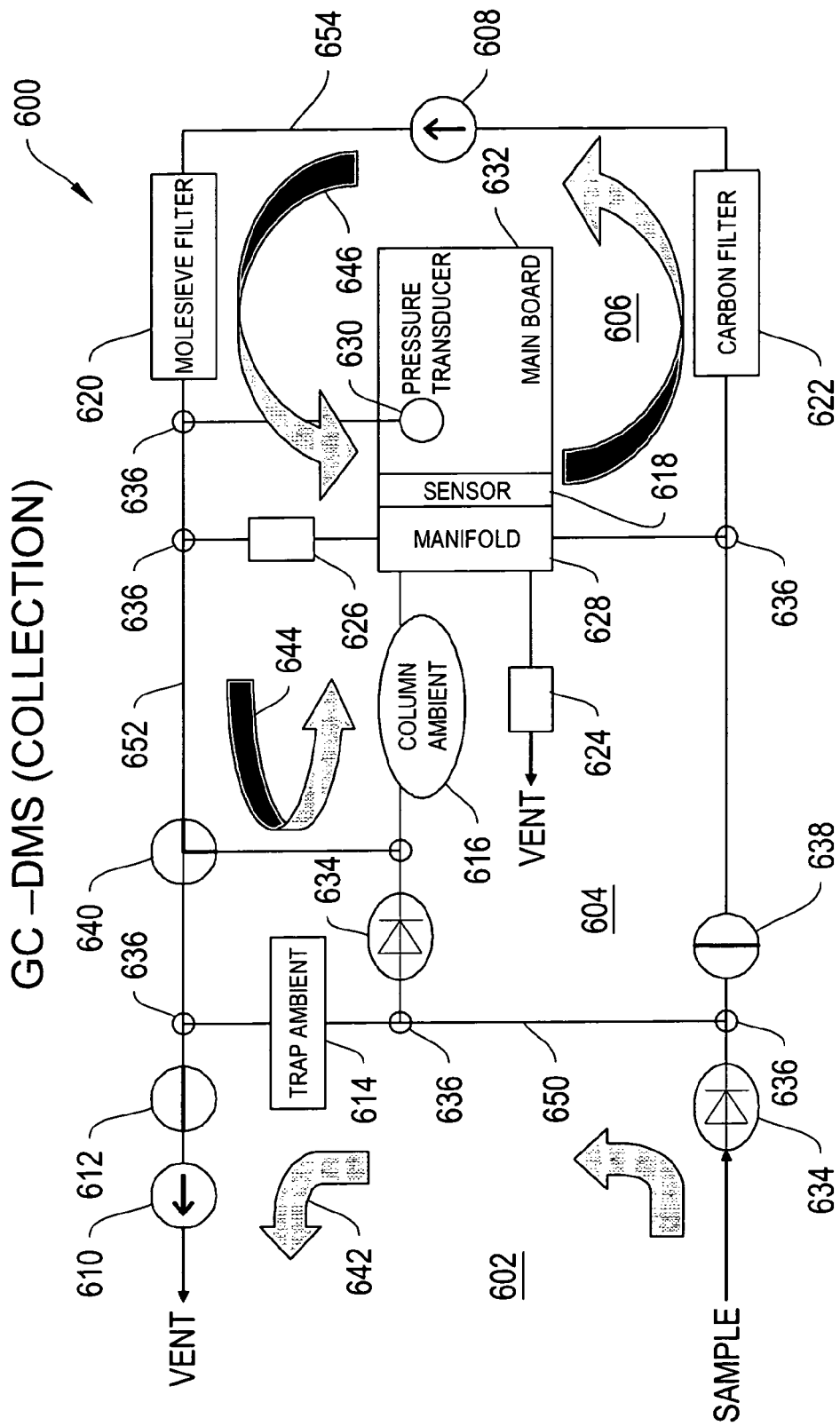
FIG. 31A is a conceptual diagram of the configuration of a GC-DMS system during the sample collection phase according to an illustrative embodiment of the invention.

FIG. 31A is a conceptual diagram of the configuration of a GC-DMS system 600 during the sample collection phase according to an illustrative embodiment of the invention. The GC-DMS system 600 includes a sample gas flow section 602, a carrier/split gas flow section 604, and a transport gas flow section 606. The sample gas flow section includes a sample flow path 650. The carrier/split gas flow section 604 includes a flow path 652. The transport gas flow section 606 includes a flow path 654. The GC-DMS system 600 includes various components such as transporter flow pump 608, sample pump 610, sample solenoid valve 612, sample trap 614, a GC column 616, and a mobility based analyzer 618. The GC-DMS system 600 further includes a molesieve filter 620, a carbon filter 622, an air balance capillary 624, a transport flow capillary 626, a pressure transducer 630, a main circuit board 632, check valves 634, tee connectors 636, a split flow solenoid valve 638, and 3-way valve 640. Micromachined valves, magnetic actuated valves, electrostatic actuated valves may all be used.

In operation, during a sample collection phase, a sample S is drawn in the sample gas flow section 602 and flowed in the direction 642 through the trap 614. The trap 614 collects and/or concentrates the sample S or certain constituents of the sample S during the sample S collection phase. During sample S collection, the solenoid valve 612 is open and/or on while the solenoid valve 638 is closed and/or off. Also, the sample pump 610 is on to generate sample S flow in the direction 642 through the trap 614. In one embodiment, the trap 614 operates at temperatures of about ambient to 350° C. In other embodiments the trap can be used for pyrolysis and can be heated to 700 or 800° C. The temperature may include one or a combination of ramped, stepped, and constant temperature setting through a range of temperatures. Other portions of the sample gas flow section 602 may operate at ambient temperatures and/or constant temperature in the range of about 80 to 160° C. A check valve 634 may be employed to prevent and/or reduce back flow against the flow 642.

During the sample S collection phase, the transport flow pump 608 may continuously run to provide continuous recirculation of a transport gas through the transport gas flow section 606 in the direction 646. In one embodiment, the 3-way valve in positioned to direct gas flow in the direction 644 through the GC column 616, but not through the trap 614. The pressure transducer 630 may be employed to monitor pressure and/or gas flow through the mobility based analyzer 618. In one embodiment, a controller, residing on the main board 632, monitors the pressure transducer 630 and regulates the flow rate in the transport gas flow section 606 by controlling the transport flow pump 608. A vent and air balance capillary 624 may be employed to vent excess gas and/or compensate for additional gas drawn into the transport gas flow section 606 and/or carrier/split gas flow section 604 from the sample gas flow section 602. The molesieve filter 620 and carbon filter 622 continuously filter and remove certain impurities and/or contaminants from the transport gas in section 606. Each filter 620 and 622 may be detachably connected to the GC-DMS system 600 to enable convenient replacement of a filter after a period of time and/or use.

In one embodiment, the transport gas flow rate may be less than or equal to about 300 cc/min. The transport gas capillary 626 may cooperate with the transport flow pump 608 to regulate the transport gas flow rate to a select rate. During the collection phase, the gas flow rate through the GC column 616 may be about 1-5 cc/min while the flow rate in the sample gas flow section is about 50-100 cc/min. In another embodiment, where an ion flow generator is employed within the transport gas flow section 606, the transport gas flow rate may operate at about the same flow rate as the flow rate of gas and/or sample S constituents exiting the GC column 616.

Figure 31B:
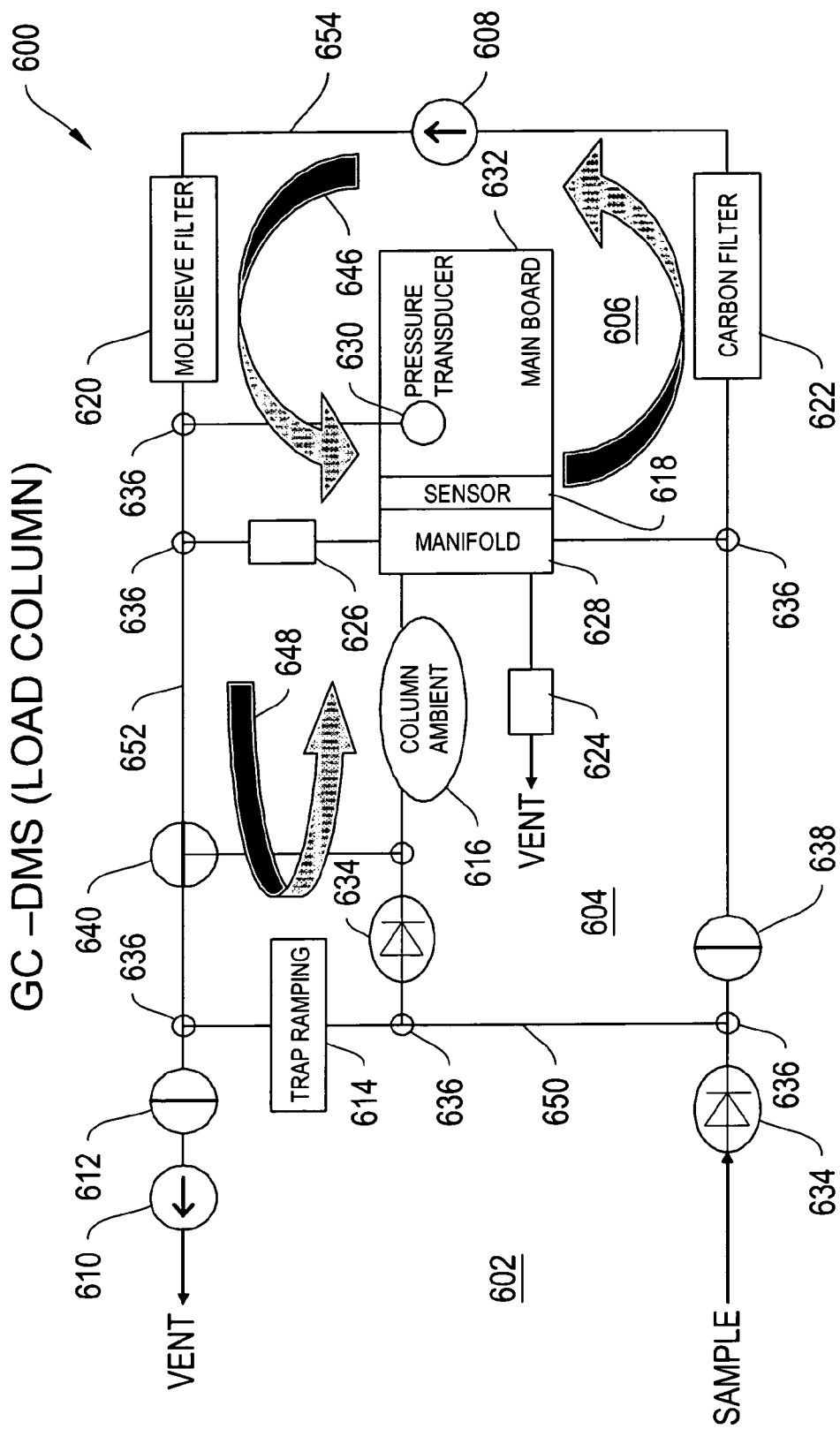
FIG. 31B is a conceptual diagram of the configuration of a GC-DMS system during the GC column loading phase according to an illustrative embodiment of the invention.

FIG. 31B is a conceptual diagram of the configuration of the GC-DMS system 600 during the GC column loading phase according to an illustrative embodiment of the invention. In operation, during the loading phase, the 3-way valve is positioned to direct carrier/split gas in the direction 648 through the trap 314 and then through GC column 616 for a period of time to load the GC column 616 with the sample S collected by the trap 314 during the sample collection phase. Due to the GC process, constituent compounds of the sample S become separated in time and exit the GC column 616 at different times. The transport flow pump 608 continues to recirculate transport gas through the transport gas flow section 606 including the mobility based analyzer 618. In one embodiment, the carrier gas flow rate through the GC column 616 is within a range of about 1-15 cc/min. In certain embodiments, various sections and/or components within the carrier/split gas section 604 operate at about ambient temperature. In other embodiments, certain components and/or sections, such as the manifold 628, operate in the temperature range of about 80 to 160° C. In a further embodiment, the GC column operates in a temperature range of about ambient to 200° C. The temperature within the GC column may be varied, ramped, stepped, and/or set at a constant temperature for a period of time depending on the type of analysis and/or type of sample to be analyzed.

Figure 31C:
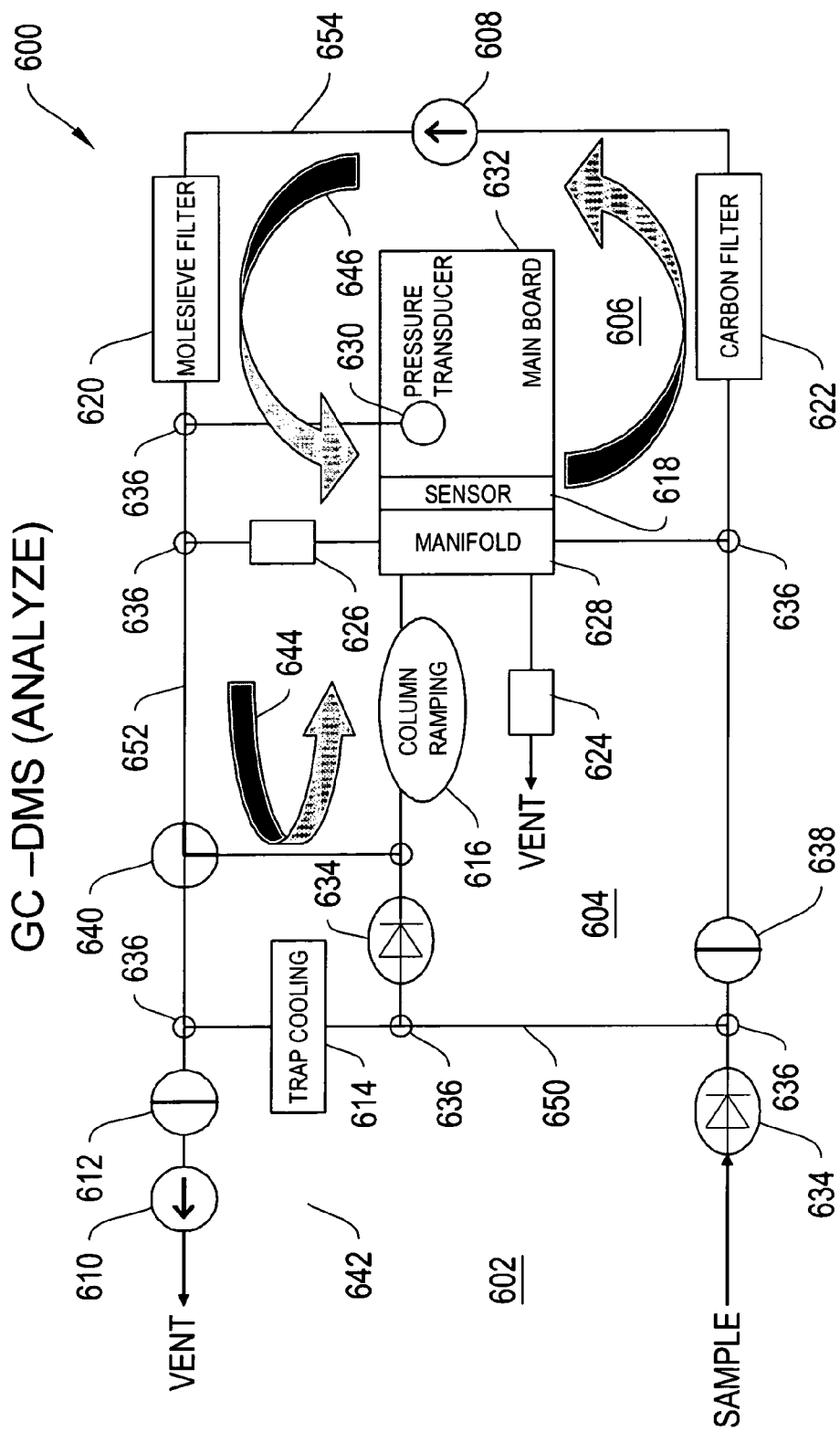
FIG. 31C is a conceptual diagram of the configuration of a GC-DMS system during the sample analyzing phase according to an illustrative embodiment of the invention.

FIG. 31C is a conceptual diagram of the configuration of the GC-DMS system 600 during the sample analyzing phase according to an illustrative embodiment of the invention. In operation, during the sample analysis phase, the 3-way valve 640 is positioned to direct carrier gas flow in the direction 644 through the GC column 616 while bypassing the trap 614. The transport flow pump 608 is on and provides transport gas flow through the transport gas flow section in cooperation with the capillary 626. In one embodiment, the transport gas flow of about 300 cc/min provide a make up gas flow to enable the mobility based analyzer 618 to properly filter and detect certain ion species of the sample S. For example, where the mobility based analyzer 618 includes a DMS analyzer, the required flow rate through the DMS analyzer may be about 300 cc/min. Because the carrier gas flow rate exiting the GC column is about 1-15 cc/min, the transport gas flow section 606 provides the necessary additional transport gas flow required by the DMS analyzer. In other embodiments, an ultra compact DMS analyzer requires flow rates of about the same or less than the flow rate exiting the GC column 616. Thus, a make up transport gas is not required for sample analysis.

In one embodiment, the foregoing sample collection, column loading, and analysis phases are implemented in a continuous manner with a compact GC-DMS system 600. In another embodiment, sample collection is performed continuously while column loading and analysis are performed intermittently and/or periodically. The analysis phase may also be performed continuously, intermittently, as desired, and/or periodically. In certain embodiments, the flow paths 650, 652, and 654 including micromachined channels, nanostructures, pipes, conduits, cavities, capillaries, and any like conductive and/or non-conductive flow directing structures. In certain embodiments, certain components, such as the molesieve filter 620, the carbon filter 622, and the transport flow pump 608, are operated at about ambient temperature. In another embodiment, the mobility based analyzer 618 is operated at a constant temperature with the range of about 80 to 160° C.

The trap 614 may include one or more tube, nanotubes, or a micro hot plate. The hot plate may be coated with sorbent or absorbent materials. The trap material may include, without limitation, poly dimethal siloxane (PDMS), an organofunctionalized PDMS coating or membrane, a short packed column with Tenex® and/or a graphitized carbon sieve, and/or carbon nanotubes.

The GC column 616 may be coated with carbon nanotubes. The GC column 616 may include a thin film or layer adhering to an inner wall as a stationary phase made by plasma polymerization, i.e., a plasma polymerized thin film station phase. The system 600 may include one or more integrated miniature flow sensors to monitor gas flow through the various modules.

Figure 32A:
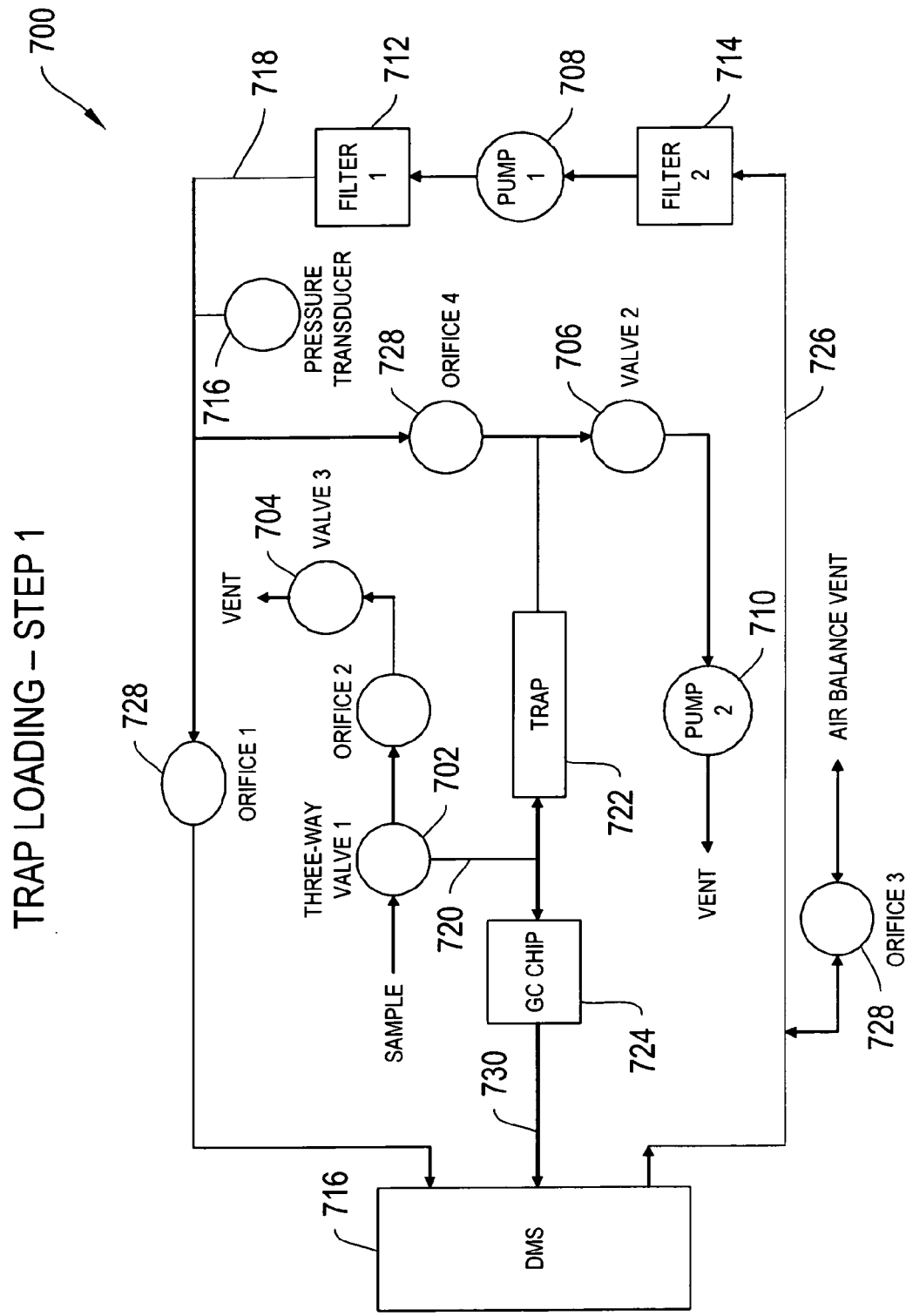
FIG. 32A is a conceptual diagram of another configuration of a GC-DMS system during the sample collection/trap loading phase according to an illustrative embodiment of the invention.

FIG. 32A is a conceptual diagram of another configuration of a GC-DMS system 700 during the sample collection/trap loading phase according to an illustrative embodiment of the invention. The GC-DMS system 700 includes a 3-way valve 702, split valve 704, sample valve 706, transport pump 708, sample pump 710, filter 712, filter 714, DMS analyzer 716, transport flow path 718, sample flow path 720, trap 722, GC column 724, transport return flow path 726, orifices 728, and GC column outlet flow path 730.

In operation, during sample S loading, the split valve 704 is off and/or closed, the sample pump 710 is on, the sample valve 706 is on and/or open, and the 3-way valve 702 is in the sample position to allow sample S flow into the GC-DMS system 700 and through the trap 722, the sample valve 706, the sample pump 710 and a vent. During sample S collection and/or trap loading, the trap 722 collects and/or concentrates certain constituents of a sample S. During the sample S collection, there is minimal to no carrier gas flow through the GC column 724. The GC column 724 may include a micromachined capillary and/or set of capillaries embedded on a substrate.

Figure 32B:
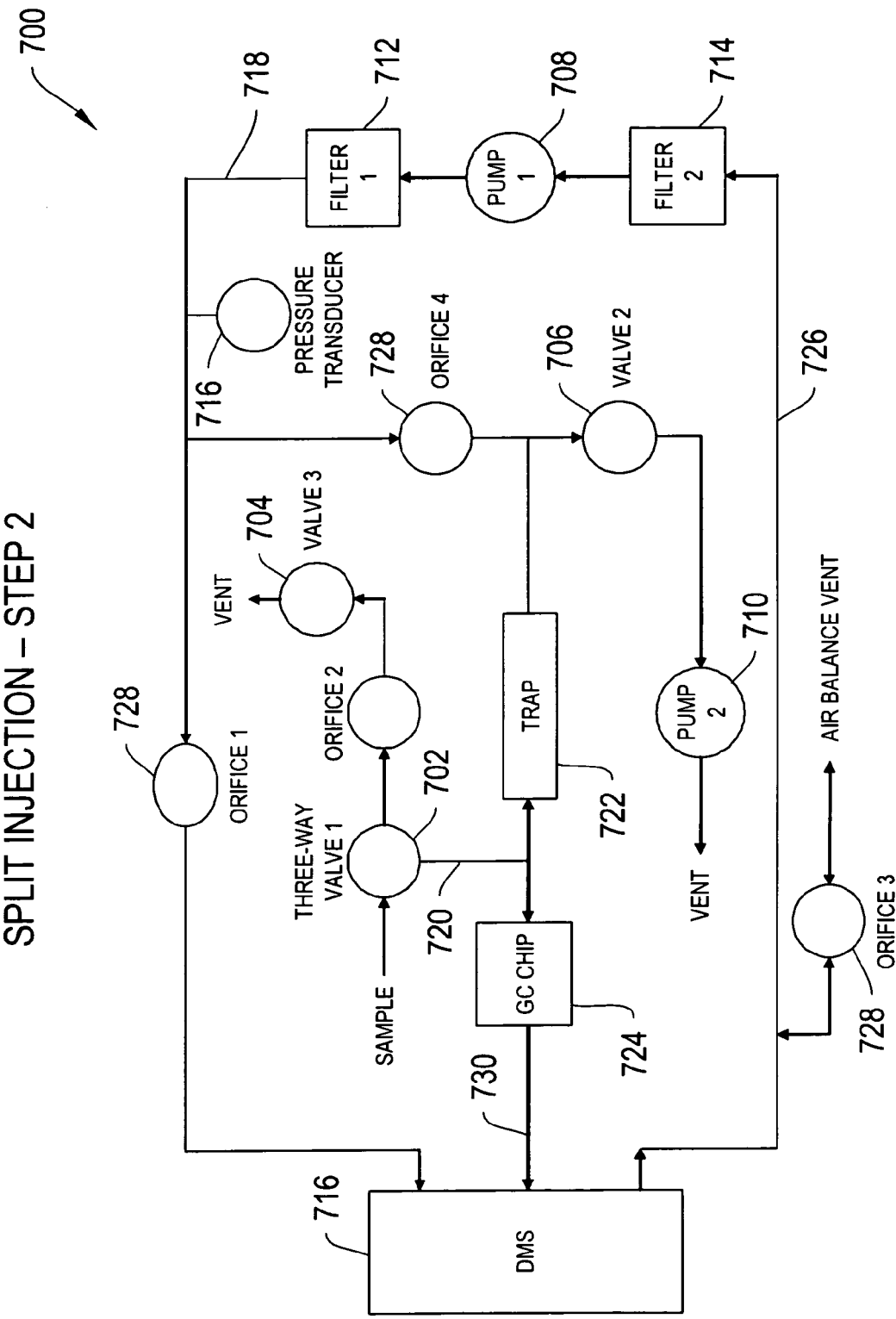
FIG. 32B is a conceptual diagram of another configuration of a GC-DMS system during the GC column loading/split injection phase according to an illustrative embodiment of the invention.

FIG. 32B is a conceptual diagram of another configuration of a GC-DMS system 700 during the GC column loading/split injection phase according to an illustrative embodiment of the invention. In operation, the split valve 704 is on and/or open, the sample pump 710 is off and/or closed, the sample valve is off and/or closed, and the 3-way valve is in the split position to enable flow through the trap 722 and into the GC column 724, but also through the split valve 704 and out a vent. The sample S flow from the trap 722 is provided by the transport gas flow generated by the transport pump 708 which flow through orifice 4 into the trap 722 and continues through the GC column 724.

Figure 32C:
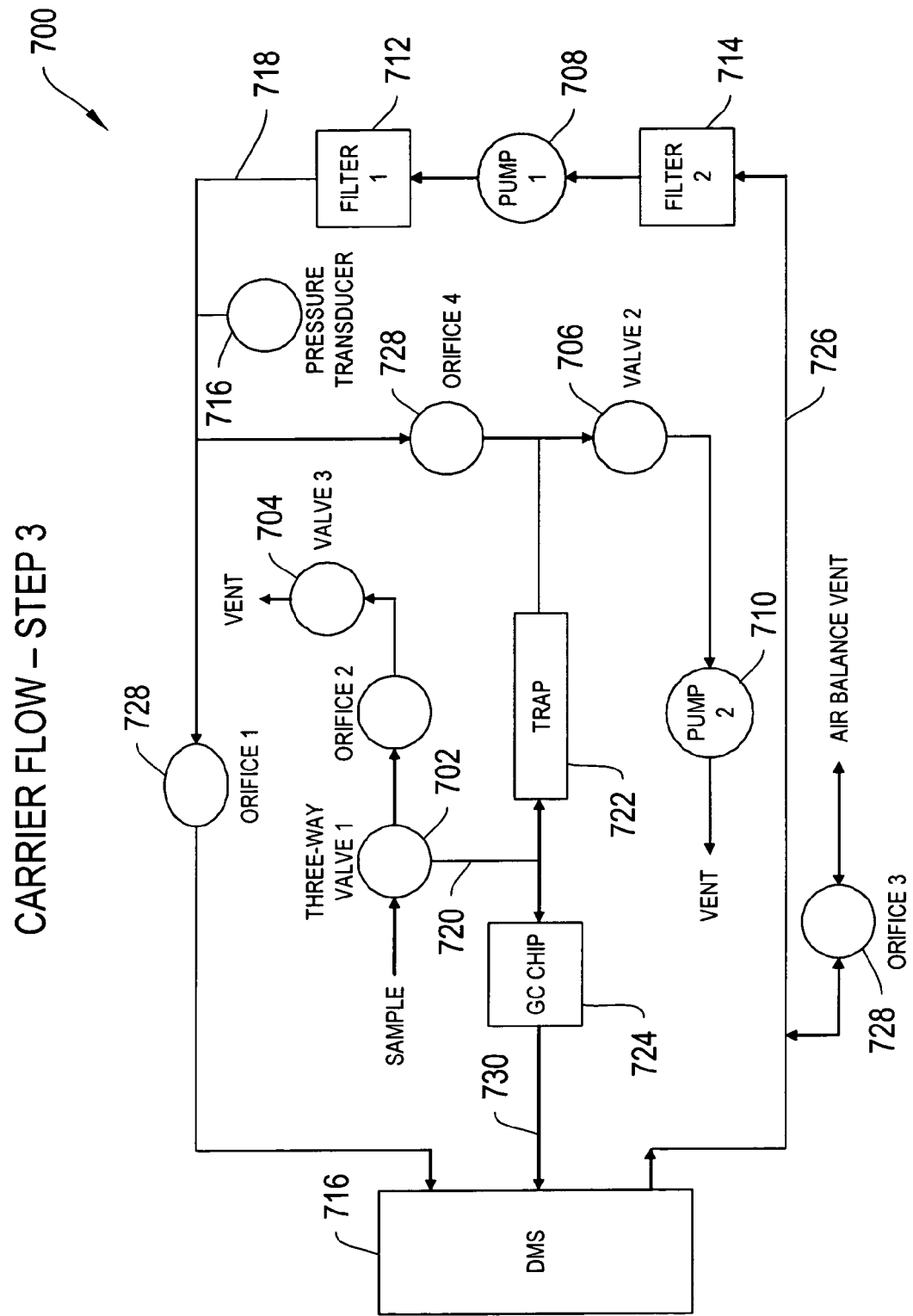
FIG. 32C is a conceptual diagram of another configuration of a GC-DMS system during the sample analyzing phase according to an illustrative embodiment of the invention.

FIG. 32C is a conceptual diagram of another configuration of a GC-DMS system 700 during the sample analyzing phase according to an illustrative embodiment of the invention. In operation, the split valve 704 is off and/or closed, the sample pump 710 is off and/or closed, the sample valve 706 is off and/or closed, and the 3-way valve 702 is in the split position to enable flow through the trap 722 and the GC column 724. The sample pump 708 is on and provides transport flow through the filter 712, along the flow path 718, through an orifice 728, through the DMS 716, along the return flow path 726, through the filter 714, and back through the pump 708, and so on. An orifice connected to the return flow path 726 connects with an air balancing vent to compensate for additional gas introduced into the GC-DMS system 700. In one embodiment, the transport pump 708 provides sufficient make gas flow to the DMS analyzer 716 to enable the DMS analyzer to analyze sample constituents eluted from the GC column 724 via the flow path 730.

Figure 33:
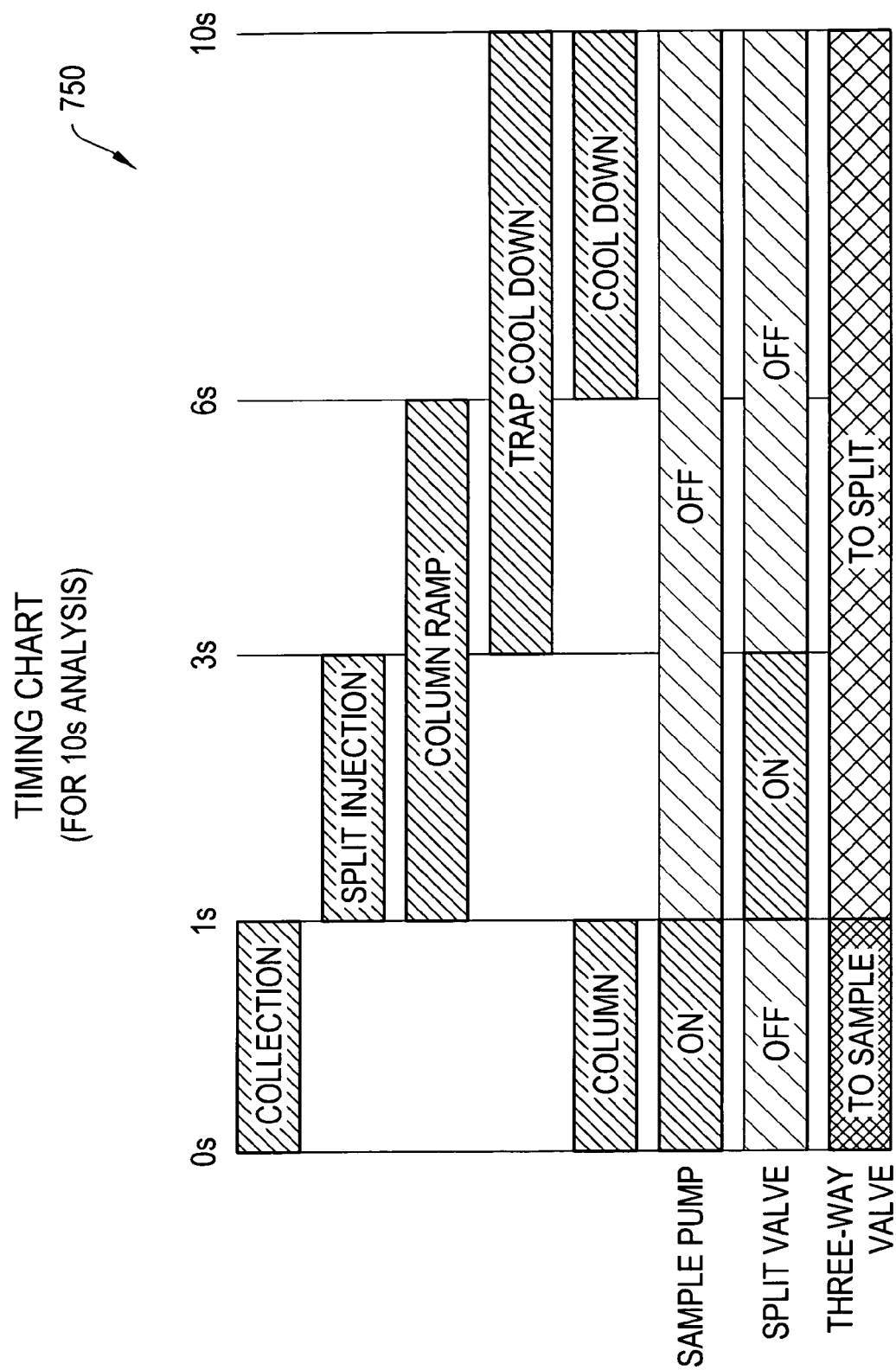
FIG. 33 is an exemplary timing chart indicating the position and state of various valves and pumps within the GC-DMS at various times according to an illustrative embodiment of the invention.

FIG. 33 is an exemplary timing chart 750 indicating the position and state of various valves and pumps within the GC-DMS at various times according to an illustrative embodiment of the invention. FIG. 33 illustrates that various functions may be perform sequentially, concurrently, or in an overlapping time manner. For example, the split injection phase follows the collection but occurs concurrently with the first two seconds of the GC column 724 temperature ramping. GC column 724 temperature ramping may further overlap trap 722 cool down, and so on.

Figure 34:
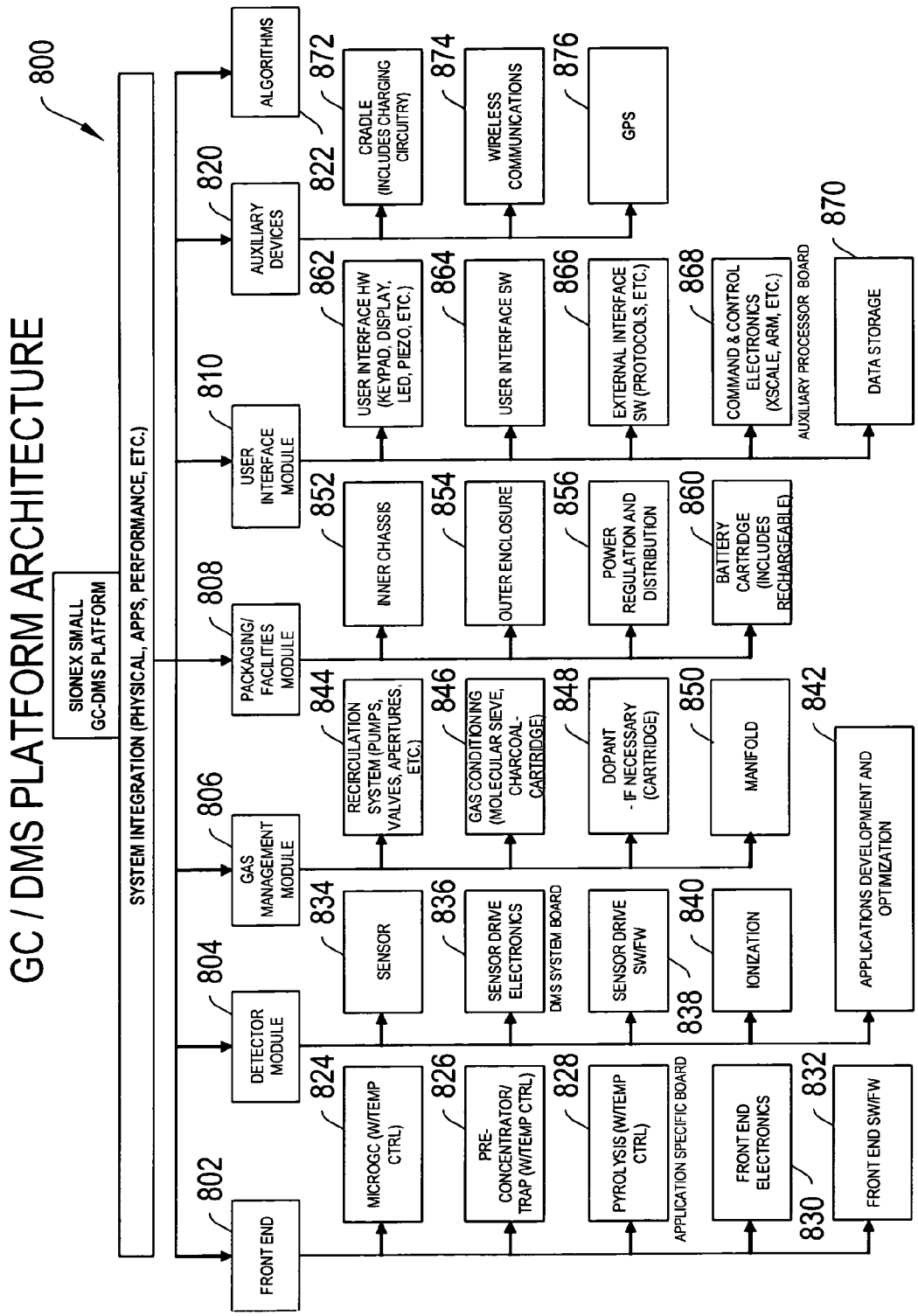
FIG. 34 is a block diagram of the platform architecture of a GC-DMS system according to an illustrative embodiment of the invention.

FIG. 34 is a block diagram of a GC-DMS system platform architecture 800 according to an illustrative embodiment of the invention. The platform architecture 800 generally includes physical components, applications, performances, and operations. The platform architecture 800 includes several GC-DMS architecture sections such as a front end 802, a detector module 804, a gas management module 806, a packaging/facilities module 808, a user interface module 810, auxiliary devices 820, and algorithms 822. The front end 802 may include various components that support to collection and/or receipt of a sample along with facilitating pre-condition of the sample before delivery to other components. The front end 802 may include a gas chromatograph 824, a pre-concentrator/trap 826 including temperature control, a pyrolysis unit 828 including temperature control, front end electronics 830 for controlling the various front end components, and front end software/hardware 832.

The detector module 804 may include one or more sensors, sensor drive electronics such as a DMS supportive system board, sensor drive software and/or firmware, an ionization source and/or ionization control system. The detector module 804 may include a sensor 834 such as DMS analyzer or other mobility based analyzer, sensor drive electronics 836, sensor drive software/hardware 838, and an ionization unit 840 such as a plasma generator. The gas management module 806 may include a recirculation system 844 including pumps, valves, flow generators, orifices, apertures, and so on, a gas conditioning system 846 including molecular sieve and/or charcoal cartridge, a dopant introduction system 848, and a manifold 850. The manifold 850 may provide and/or support certain conditioning control such as, for example, flow conditioning, heating, cooling, house radioactive source material, and providing a mounting structure for components such as a DMS chip. In one embodiment, the manifold 850 includes a metal such as brass. The packaging/facilities module 808 may include an inner chassis 852, an outer enclosure 854 for a GC-DMS system, a power regulation and distribution system 856, and/or a battery 860. The battery 860 may be in the form of a cartridge and be rechargeable. Alternatively, the power system 856 may utilize a line power source, a solar powered source, or like regulated power source.

The user interface module 810 may include user interface hardware 862 such as a keypad, display, LED, piezo, a graphical user interface (GUI), and like user interface components. The user interface module 810 may include user interface software 864, external interface software 866, command and control electronics 868, and/or data storage 870. The auxiliary devices 820 may include a cradle 872 with battery charging circuitry, a wireless communications interface 874 for wireless interaction with a remote control and/or information gather unit, or with another GC-DSM system, and/or a global positioning system (GPS) unit 876 that provided mapping and location/position information to a processor unit. An applications development and optimization unit 842 may be included to enable hardware/software development.

The external software interface 866 may include one or more communication protocols such as Ethernet, TCP/IP, Bluetooth, 802.X, cellular, and any other wired and/or wireless protocols. The command and control electronics 868 may include at least one of Xscale, ARM, and other like mechanisms. The data storage 870 may be in the form of at least one of a hard drive, memory chip, flash memory, memory stick, ROM, RAM, disk ROM, and any like memory media.

The algorithms section 822 may be embedded with the firmware, software, and/or with one more data storage elements. The algorithms section 822 may include algorithms that support the control of the various modules and/or components of the architecture, or may support the interpretation and/or presentation of information acquired from the components of the architecture. For example, one algorithm may correlate data from the GC and DMS detector and present that data as a three-dimensional dispersion plot of ion intensity over a range of elution time versus compensation voltage. Other algorithms may control temperature within the trap, GC column, or DMS filter. A further algorithm may compare certain detected spectra with known spectra that is stored with one or more data storage components to identify an unknown ion species.

Figure 35:
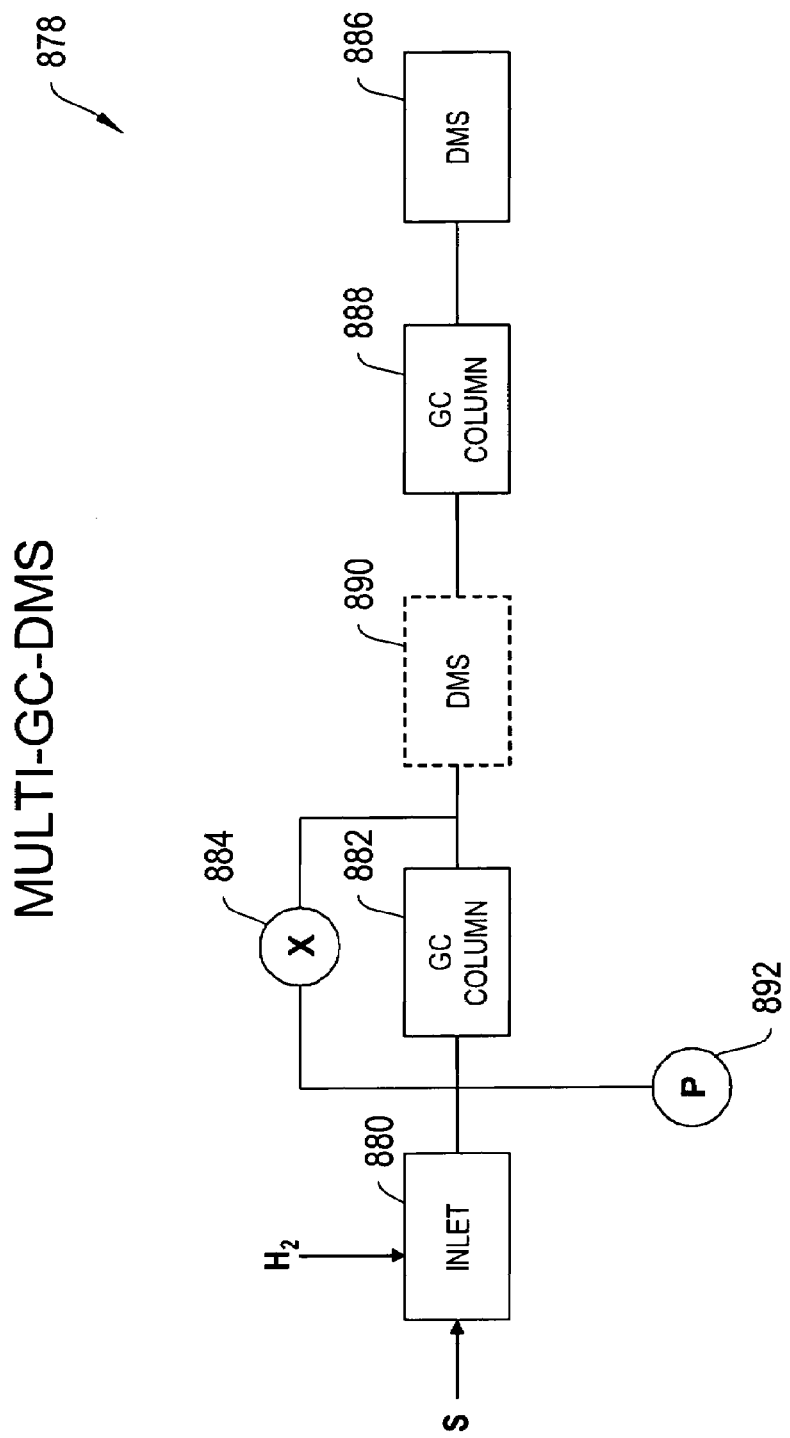
FIG. 35 is a block diagram of a multi-stage GC-DMS system according to an illustrative embodiment of the invention.

FIG. 35 is a block diagram of a multi-stage GC-DMS system 878 according to an illustrative embodiment of the invention. The system 878 includes a first GC column 882 and a second GC column 888. The system 878 employs a DMS analyzer 886 to detect a sample exiting the second GC column 888. Optionally, the system 878 may include a second DMS analyzer 890 to detect the sample exiting the first GC column 882 prior to delivery to the second GC column 888. Each DMS analyzer may include a DMS filter and/or detector. Each DMS analyzer may including an ionization source to ionize the sample. Generally the ionization sources which can be used in or with typical DMS systems may include field emission tip based ionization source which emits electrons at relatively low voltages, the field emission tip may be formed by nano-fabrication such as from carbon nano-tubes. The ionization source may be a reverse flow plasma source, where the ions formed by the plasma are extracted from the plasma region by an electric field which drives the ions into the DMS or IMS counter to a gas or air flow. In this way, neutrals such as NOx's are minimized and a favorable negative ion chemistry preserved in the DMS.

The ionization source may also be radioactive Ni63 or other radioactive materials. The ionization source may be a PID, or UV ionization source or an LED or a UV LED or the like. Another ionization source may be realized by electrospraying a solvent which ionizes the solvent and then mixing the ionized solvent with the analyte. A charge exchange occurs which then ionizes the analytes.

The system 878 may include an inlet section 880. The inlet section 880 may include various components such as pumps, valves, switches, a trap, a GC column, a pre-concentrator, an ion mobility based filter, or any other pre-separator mechanisms to facilitate pre-conditioning of the sample prior to introduction into the GC column 882. The system 878 may include a bypass valve 884 to allow the sample to bypass the GC column 882 and direct the sample into the GC column 888. Optionally, if the DMS analyzer 890 is present, the sample may be directed to DMS analyzer 890. The system 878 may include one or more pressure sensors 892 to measure flow path pressure and/or flow rate throughout the system 878.

Each GC column may include a packed column and/or a capillary tube column. Each column may include various stationary phases. Each column may include polar or non-polar coatings. In one embodiment, at least one GC column includes a liquid ionic phase where both polar and non-polar compound separation are performed. In another embodiment, the first GC column 882 is packed while the second GC column 888 is non-packed. In a further embodiment, the column phase of column 882 is different than the column phase of column 888. By employing at least two columns, each using different phases, the system 878 is able to perform GC-based chemical separation of a sample in an enhanced manner.

In certain embodiments, the GC columns 882 and 888 are integrated and micro-fabricated on a substrate. The GC columns 882 and 888 and supporting electronic components, valves, micro injection systems, gas connectors, and other micromachined (MEMS) components may be integrated into a integrated multi-layer printed circuit board (PCB). The PCB may include other components such as a microcontroller, analog-to-digital converter (A/D), memory device, integrated amplifiers and other circuits to facilitate operation of the system 878.

In certain embodiments, the GC-GC configuration of system 878 provides improved sample resolution with respect to conventional GC columns. Additional GC columns may be employed in series and/or parallel to further enhance sample separation. In one embodiment, at least two GC columns are composed of different stationary phases to enable a sample to be separated by two different separation mechanisms. The different separation mechanisms may then provide orthogonal information to better identify and/or discriminate among various sample components and/or species. In one embodiment, the first column 882 and/or column set includes a standard low-polarity column while the second column 888 includes more polar materials. The second column 888 may be relatively shorter than the first column 882 to reduce the elution time and, thereby, increase the sampling rate of the system 878.

In one embodiment, a modulator may be employed between the first column 882 and second column 882 to trap and focus the sample eluted from the first column 882 before introduction into the second column 888. The modulator may collect sample elutions from the first column 882 for a period of time and then deliver the collected elutions to the second column 888. The modulator, by trapping and focusing eluted sample from the first column 882, can significantly improve the system 878 sensitivity by pulsing the sample into the second column 888 periodically. This pulsing enables the separation of various sample components via the second column 888 and, thereby, enhances sample component resolution and sensitivity. By using different phases in each column, the system 878 is able to resolve components of a sample that would normally elute concurrently in a convention GC column. In one embodiment, the modulator pulses are timed to correspond to the elution and/or retention times of various sample components.

Each GC column 882 and 888 may be micromachined/nanomachined and etched within a substrate using a surface micromachining technique. At least one GC column may be integrated with a DMS analyzer and/or sensor on a single integrated chip. Each column may include a path shape that is spiral, serpentine, rectangular, helical, and/or circular. Each column may less than about 100 um, 75 um, 50 um, 25 um, 10 um, 5 um, or 1 um wide. Each column may be less than about 500 um, 400 um, 200 um, 100 um, 50 um, 20 um, or 10 um deep. Air may be used as the column carrier gas.

In one embodiment, the inlet section 880 includes a split sample and gas input such as H2 and/or air. The inlet section 880 may include micromachined components. For example, the inlet section 880 may include a micromachined MEMS pre-concentrator unit capable of collecting select analytes from the sample stream. The unit may include a thin silicon nitride membrane supporting a patterned metal film heating element. The membrane may be coated with a select film to selectively and reversibly absorb certain sample components.

The DMS analyzer 890 and/or 886 may include a detector. The detector may include a functionalized chemo-resistive transducer, a polymer functionalized field effect transistor (FET). The FET gate may be functionalized to collect select ions and/or ion species. A particular FET structure may be employed such as a MOSFET, JFET, and other like FET or like semiconductor structure such as a transistor, diode, switch, varactor, and so on. The detector may include a dielectric barrier discharge detector. The detector may include a functionalized nanotube detector and/or a cantilever type detector. The cantilever type detector may be silicon micromachined. The detector may include one or more nano-sensor and nano-structures to facilitate the detection of certain ions. The nanotube may be utilized as a semi-conducting transducer. The detector may also detect based on surface plasmon resonance characteristics and interactions between the analyte and the transducer. In other applications the DMS can be coupled to a RAMAN spectrometer or other optical spectrometers for enhanced compound identification or detection.

Detection in the cantilever detector may be based on resonance change of the cantilever or positional deflection of the cantilever. This detection provides different, orthogonal data to the information based on ion mobility or differential mobility provided by DMS and IMS systems.

Additionally, components of the above systems 600 and 878 may be nano-machined and/or machined using nano technology. For example, the systems may include nanoinjectors and/or traps nano-based columns, and columns including or being packed with nanotubes.

Figure 36:
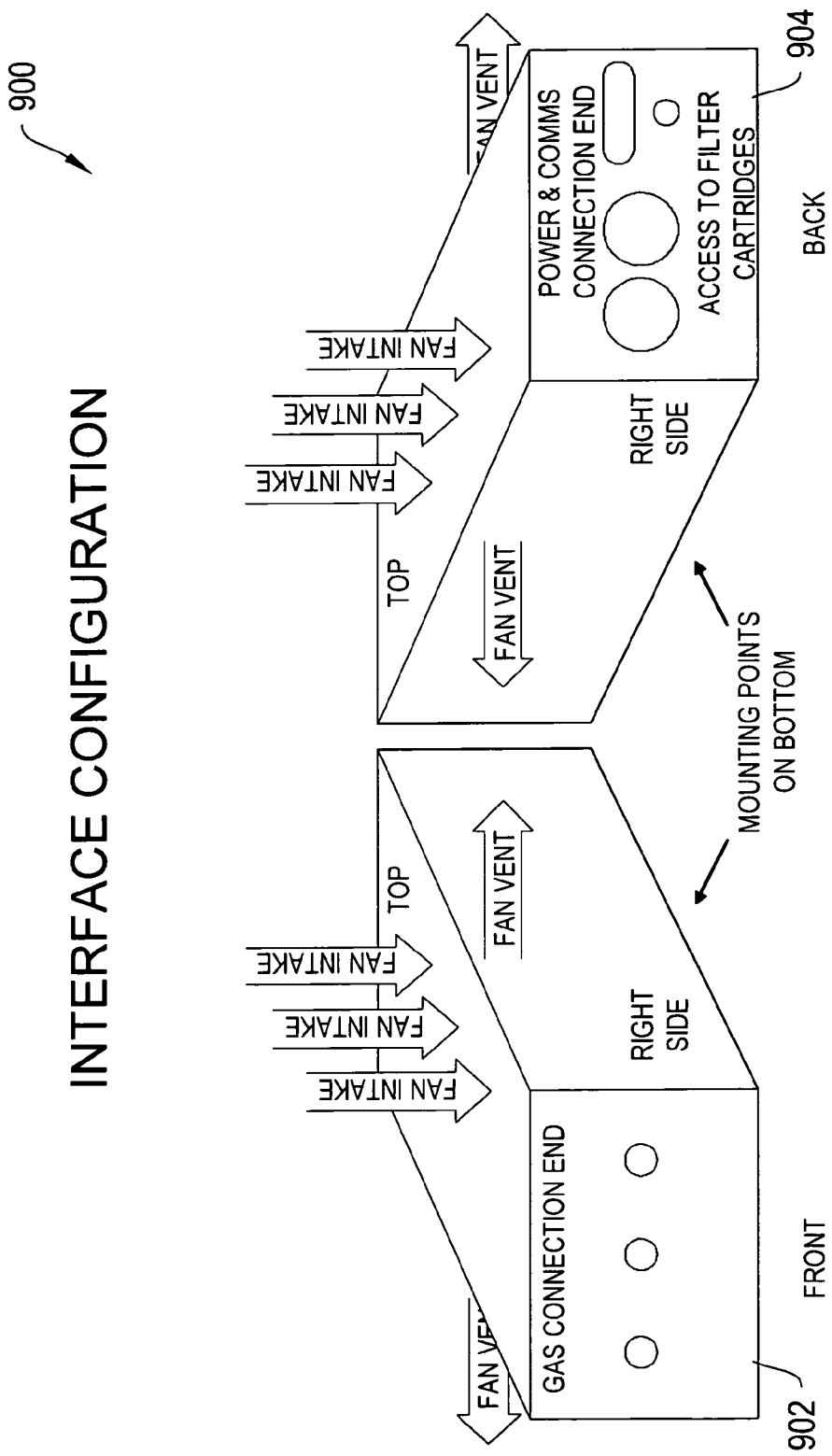
FIG. 36 is a diagram showing the relative position of various components of a compact GC-DMS system according to an illustrative embodiment of the invention.

FIG. 36 is a diagram showing the relative position of various components of a compact GC-DMS system 900 according to an illustrative embodiment of the invention. FIG. 36 shows a functional diagram of the front and back end a GC-DMS system 900 like those described above having a compact brick form factor. The front end 902 includes gas connectors to support the introduction of gases into the various modules of the system 900. The back end 904 includes power and communications connections and access to the filter cartridges to enable replacement. The system 900 may also include fan intakes to provide circuitry cooling and module air flow as well as fan vents.

FIGS. 37A-C is a schematic diagram showing top, end, and side views 952, 956, and 954 respectively of a compact GC-DMS system 950 according to an illustrative embodiment of the invention. FIGS. 37A-C show a GC-DMS system 950 of the type described with respect to FIGS. 31A-C in a brick form factor. FIG. 37A provides a top down view of the brick GC-DMS assembly and illustrates the compact assembly of various system components such as pumps, valves, a battery, filter cartridge, manifold, trap, and DMS sensor. FIG. 37B provides side view of the compact brick GC-DMS system. FIG. 37C provides another side view of the compact GC-DMS system 950. In this embodiment, the GC-DMS system 950 includes size dimensions that are less than and/or equal to about 7"×3"×1.5".

Figure 38:
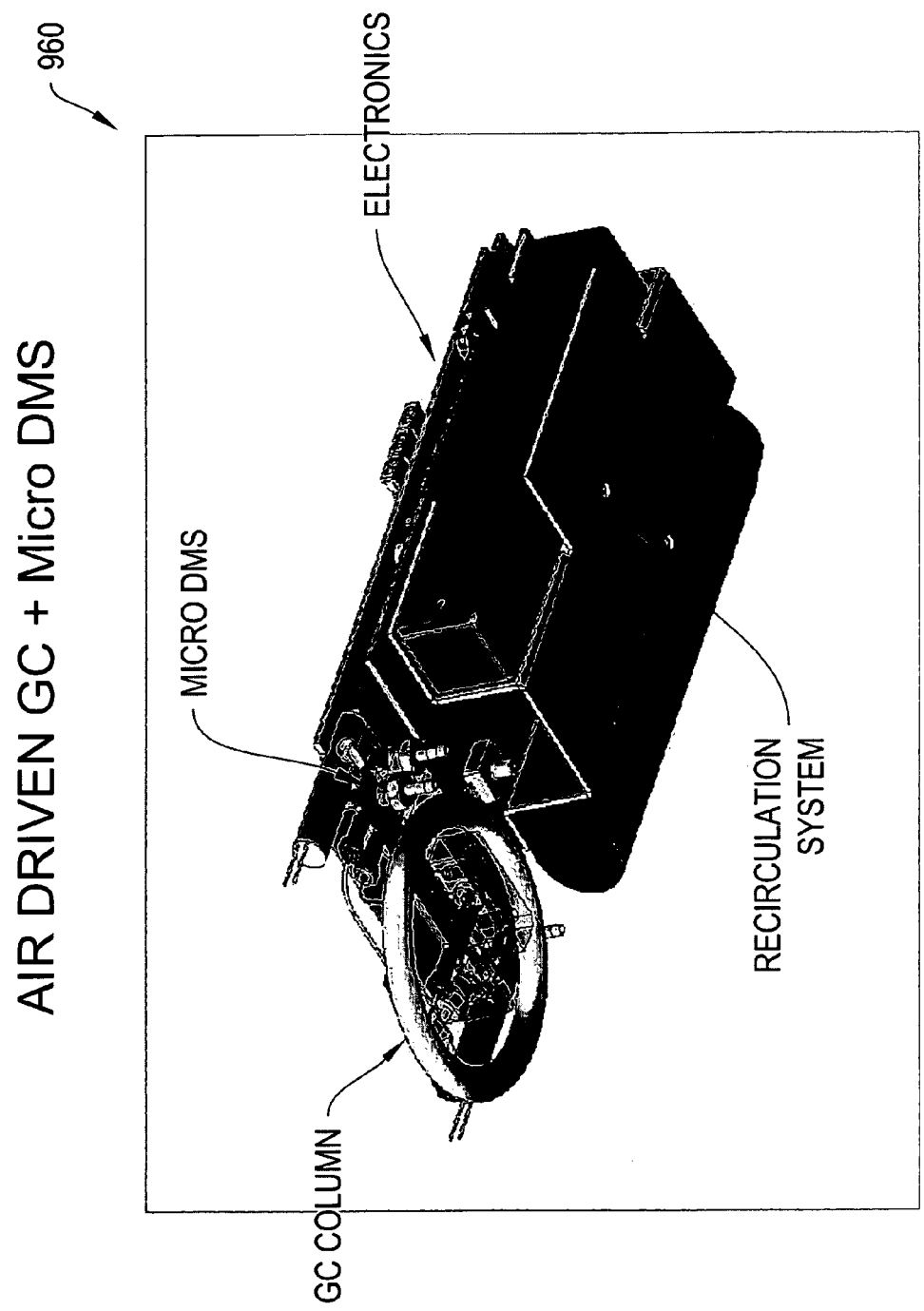
FIG. 38 is an electromechanical diagram showing to arrangement of various components within a compact GC-DMS system according to an illustrative embodiment of the invention.

FIG. 38 is an electromechanical diagram 960 showing the arrangement of various components within the compact GC-DMS system 950 according to an illustrative embodiment of the invention. The system 960 includes a compact microDMS and GC column arranged within a compact form factor to provide a portable GC-DMS unit of a size of about 7"×3"×2". In one embodiment, the GC column of the GC-DMS system is air driven. The GC-DMS system may include a pre-concentrator including, for example, a trap, plate, membrane, or other pre-concentration mechanism. The GC-DMS system may also include a recirculation system such as the system described with respect to FIGS. 31A-C. In one embodiment, the GC-DMS system 960 is configured to detect certain chemicals at concentration levels in the sub-part per billion (ppb) range. In one embodiment, the GC-DMS system 960 includes various disposable/quick connect and/or disconnect housing and structure components such as, for example, a filter. Other components may be exchangeable such as the GC column, DMS analyzer, manifold, certain components of the recirculation system (e.g., valves, pumps, capillaries), an inlet section, pre-filter, pre-concentrator, trap, molecular sieve, charcoal filter, and like GC-DMS system components.

Figure 39:
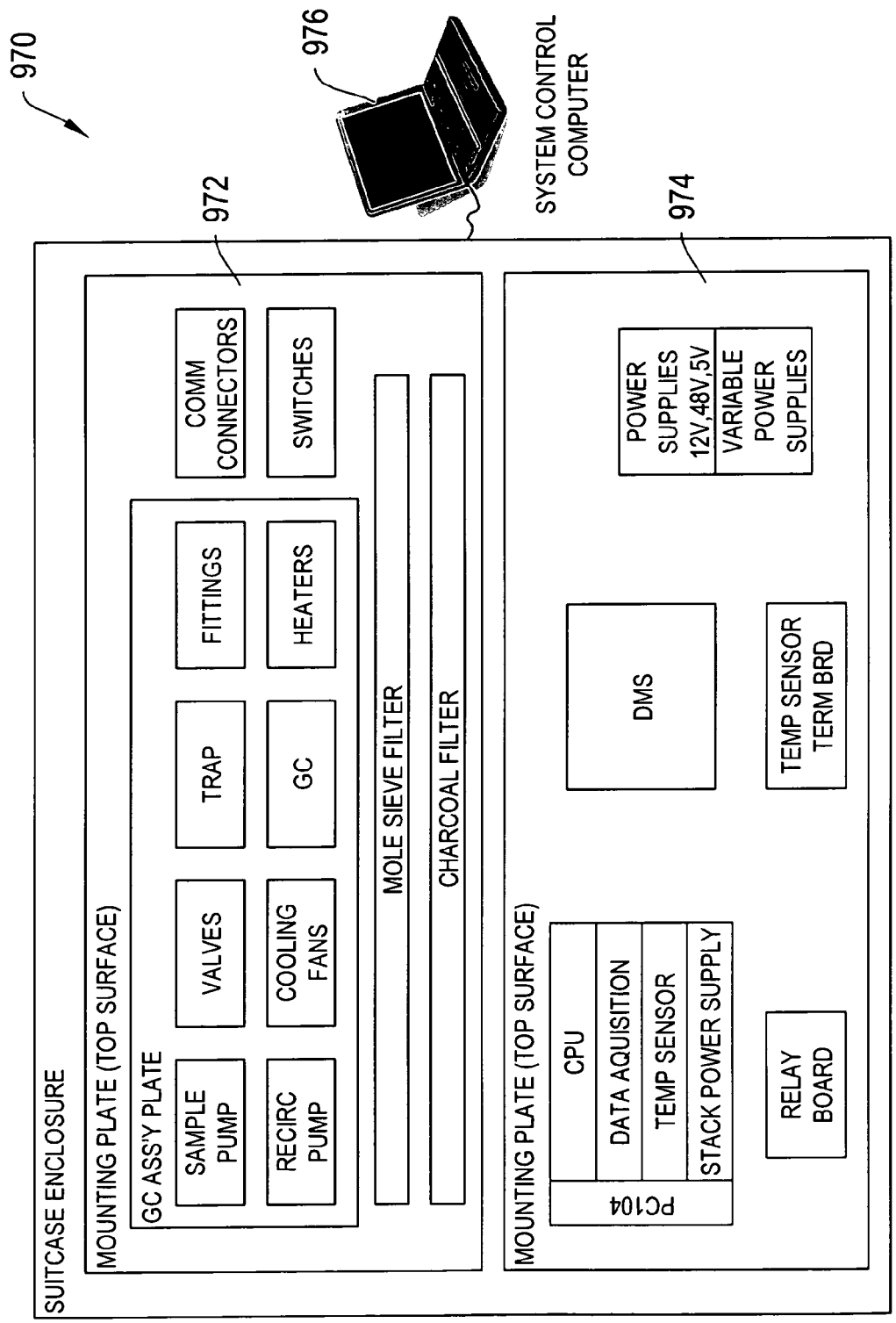
FIG. 39 is a block diagram of a GC-DMS system having a suitcase form factor according to an illustrative embodiment of the invention.

FIG. 39 is a block diagram of a GC-DMS system 970 of the type described in FIGS. 31A-C having a suitcase form factor according to an illustrative embodiment of the invention. The system 970 may include a mounting plate having a top surface 972 and a bottom surface 974. The top surface 972 may include a GC assembly section having at least one of a sample pump, valves, a trap, fittings, a recirculation pump, cooling fans, a GC column, and heaters. The top surface 972 may also include communications connections, switches mole sieve filter and/or charcoal filter cartridges. The bottom surface 974 may include a microprocessor, memory, SVAC-G, a relay board, a temperature sensor board, and one or more power supplies. The system 970 may interface with a remote and/or detachable computer such as a portable laptop computer 976 to facilitate data acquisition, analysis, and/or system 970 control.

Figure 40:
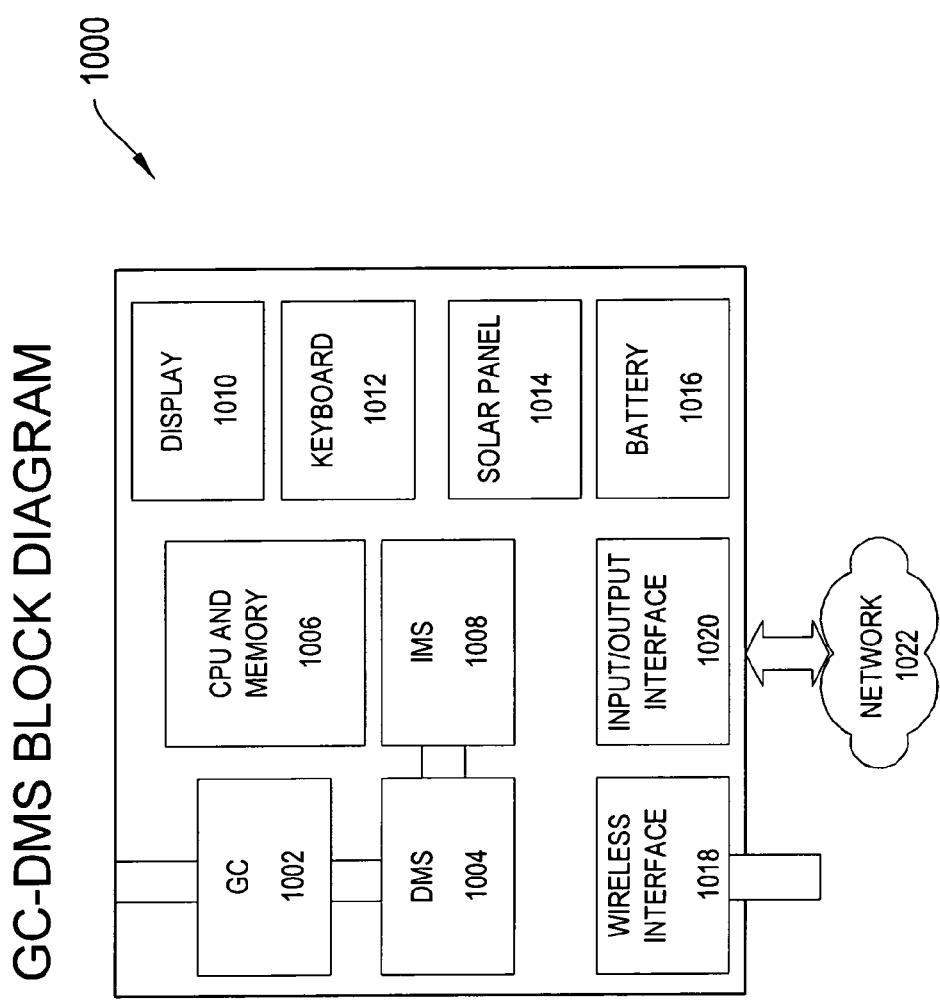
FIG. 40 is a conceptual block diagram of a GC-DMS system including a wireless interface according to an illustrative embodiment of the invention.

FIG. 40 is a block diagram of a GC-DMS sensor system 1000 including a wireless interface 1018 according to an illustrative embodiment of the invention. The GC sensor system 1000 includes various sensor components such as GC 1002, DMS 1004, IMS 1008, CPU/Memory 1006, Display 1010, Keyboard 1012, solar panel 1014, battery 1016, wireless interface 1018, input/output interface 1020. The system 1000 may be connected via interface 1020 to a network 1022 such as the Internet or a local Ethernet to facilitate communications with other sensors or a centralized processing system that controls and/or coordinates the operation of multiple sensor systems 1000. The wireless interface 1018 may also enable communications among multiple sensor systems 1000 via a wireless communications network. In certain embodiments, the sensor is embedded in a flashlight, lapel, helmet, uniform, shoes, boots, jacket, glasses, or any other wearable element.

In another embodiment, the sensor includes a global positioning system (GPS) interface. In a further embodiment, the sensor is wearable and/or communicates with a local or remote display (e.g., a heads-up display on a firefighter's helmet).

In certain embodiments, a solar cell, a fuel cell, and/or a transducer circuit provide a sufficient power source. In one embodiment, the device of FIG. 40 includes a solar panel and interfaces with a rechargeable battery 1016 to provide a solar power source. This allows for monitoring in locations where hardwired power sources are not convenient, or battery replacement is problematic. The source of light energy could be the sun, or artificial lighting, and therefore the sensor 1000 could be used inside or outdoors. The sensor 1000 could be portable or mounted in a fixed location. The solar powered panels could be attached to the sensor 1000, or mounted separately to optimize light collection. The solar panels could also be wearable. In one embodiment, the device of FIG. 40 includes an Ethernet communications interface that enables the extraction of sufficient power for DMS analysis and/or processor processing.

The sensor 1000 or other GC-DMS system such as GC-DMS system 600 may include direct driving control circuitry such as, for example, a MOSFET switch which comprises a control device having low voltage and high frequency capabilities to support significantly narrower gaps within an ultra compact DMS. In one embodiment, the GC-DMS system 600 employs a ring resonator capable of supporting frequencies in the microwave range or higher. In another embodiment, the direct drive is capable of directly generating a square wave signal for the asymmetric field of at least one filter electrode.

In certain embodiments, a GC-DMS system includes a DMS where the DMS field is used as a driving field that preferentially transports ions. In one embodiment, a sample is ionized and introduced into the analytical region (filter region) or is introduced into an ionization region and then flows to the analytical region, such as by electric field. The ions can move in the analytical region against or with a gas flow, such as where a clean gas flow (e.g., filtered air) and flows counter to average or net ion motion. The ions move toward then away from the downstream detector electrode as they travel toward the detector electrode, resulting in an average or net travel, e.g., in two steps forward and one step back. Additional and other means, such as a DC field gradient can be added for assisting ion transport.

The system may use the field dependence of ions, whether high or low. Separations can be achieved based on ion species, including light versus heavy and polarity, according to the displacement vector form the field. Simultaneous detection of both positive and negative ions species is possible as in Miller, et al., U.S. Pat. Nos. 6,495,823 and 6,512,224, both of which are incorporated herein by reference in their entirety.

Thus, in certain embodiments a longitudinal DMS (LDMS) and IMS may be included in the same device and/or integrated package. The LDMS may further interface with one or more GC columns, that may also be integrated into the same package. In an illustrative embodiment, the DMS device provides DMS detection capability but also the DMS is a detector for a conventional IMS, such as time of flight or Fourier IMS. In one mode of operation, the DMS actually measures differential time of flight. In another embodiment, a gating mechanism provides a pulse introduction of sample and enables measurement of time-of-flight.

Figure 41:
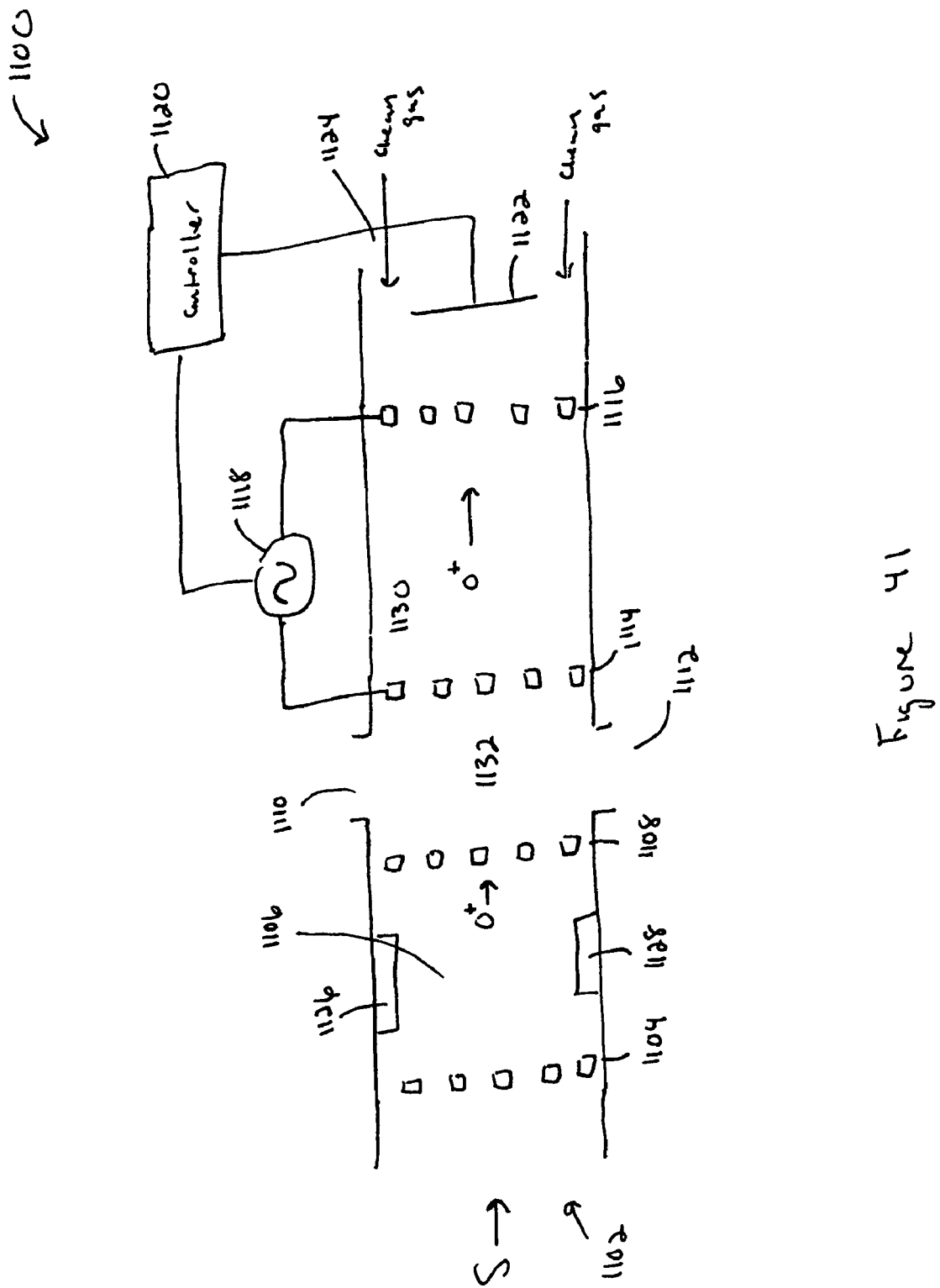
FIG. 41 is a conceptual diagram of a longitudinal DMS according to an illustrative embodiment of the invention.

FIG. 41 is a conceptual diagram of a longitudinal DMS system 1100 according to an illustrative embodiment of the invention. The longitudinal DMS system 1100 includes a sample S inlet 1102, an ionization region 1106 having ion sources 1126 and 1128, optional propulsion electrodes 1104 and 1108, exhausts 1110 and 1112, flow path 1132, filter grid 1114, analyzer region 1130, filter grid 1116, detector 1122, time-varying voltage source 1118, controller 1120, and clean gas inlet 1124.

In operation, a sample S is introduced via inlet 1102 into the ionization region 1106. One or both of the optional propulsion electrodes and/or grids 1104 and/or 1108 may generate an electric field to propel the ions along the flow path 1132. One or both of the ion sources 1126 and/or 1128 may ionize the sample S. The ion sources 1126 and 1128 may include a radioactive ion source, plasma discharge source, or other ionization source. Once ionized, the ions travel along the flow path 1132 until reaching the filter/gating electrode and/or grid 1114. The exhausts 1110 and 1112 may provide an outlet of excess transport gas or for a counter-flowing gas from the clean gas inlet 1124. The filter grid 1114 may operate as a gate to pulse ions into the analyzer region 1130 at certain times. By pulsing select ions into the analyzer region at certain times, the time-of-flight of the ions can be measured from the time of entry into the region 1130 until the ions reach the detector 1122. The filter electrode and/or grid 1116 may be synchronized with the grid 1114 to gate certain ions through to the detector and reduce possible interference in the flow path 1132.

The voltage source 1118 applies a time-varying voltage across the electrodes 11114 and 1116 to generate a time-varying electric field within the analyzer region 1130. In one embodiment, the time-varying electric field is an asymmetric field including a DC compensation field. The controller 1120, like the controller 10c of FIG. 2A, may selectively adjust the time-varying RF voltage and a compensation voltage applied to the electrodes 1114 and 1116 to allow select ion species to pass through the analyzer region 1130. Unlike the time-varying field generated by filter electrodes 26 and 28 of the system 10 which is orthogonal to the ion flow, the time-varying field of the system 1100 is substantially parallel with the ion flow in a longitudinal direction along the flow path 1130. Thus, the time-varying field effects the average net flow a different ion species differently and, thereby, causes different ions species to arrive at the detector 1122 at different times, based on each ion species mobility characteristics.

The controller 1120 may include a processor capable of measuring and/or analyzing the detected ions over a period of time as the ions reach to detector 1122. In one embodiment, the voltage generator 1118 is adjustable in response to the controller 1120 to adjust the field strength in the analyzer region for both high field and low field values. Thus, the system 1100 may operate as an IMS under low field conditions in one mode, under a mized high/low field regime in a mixed mode, or under high field conditions in another mode of operation. In another embodiment, a clean gas is introduced at the inlet 1124 that includes filtered air. In certain embodiments, the grids such as grid 1114 are circular, meshed grids. In certain embodiments, the gate 1114 is pulsed open to allow ions into the analyzer region 1130 at various intervals. In one embodiment, the potential of grid 1116 is maintained at about ground while the detector 1122 is slightly biased.

In a further embodiment, as the ions are pulsed into the analyzer region 1130, the gate 1116 is simultaneously pulsed open. Due to the delay in ions reaching the gate 1116 based on their time of flight, the stream of ions may come into and/or out of phase with the gate 1116 as it opens and closes. Thus, an interference signal may be produced that rises and falls depending on the degree to which the gate 1116 is opened and closed.

Figure 42:
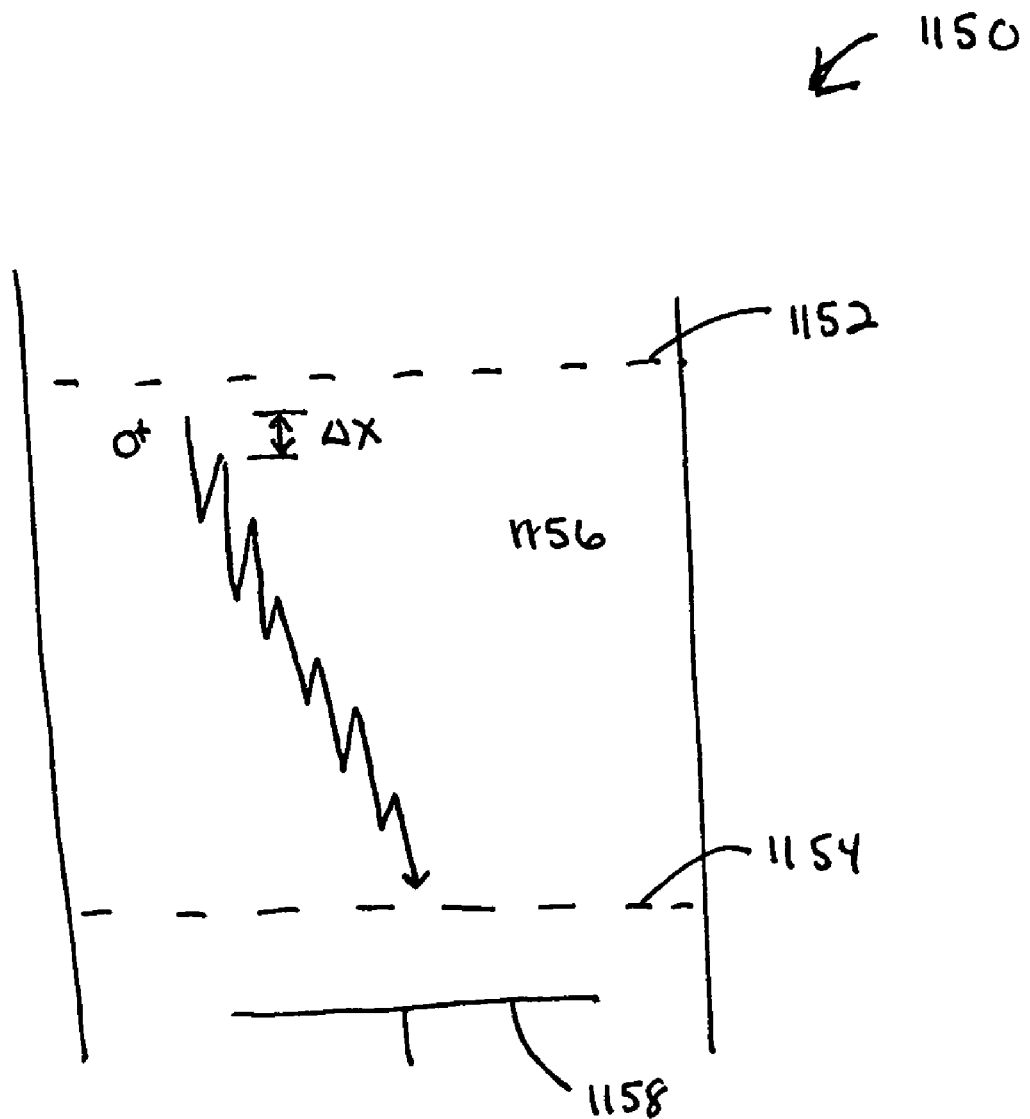
FIG. 42 is an exemplary diagram of the flow path of an ion within the analytical region of the analyzer of FIG. 41 according to an illustrative embodiment of the invention.

FIG. 42 is an exemplary diagram 1150 of the flow path of an ion within the analytical region of the analyzer of FIG. 41 according to an illustrative embodiment of the invention. The diagram 1150 includes an analyzer region 1156 with filter/gate electrodes 1152 and 1154. As discussed above, a time-varying field is applied across the electrodes 1152 and 1154. When an ion is subjected to both high field and low field components of a time-varying electric field, the ion travel a distance under the high field condition, but then travel back a distance under the low condition, creating a net displacement ΔX in the analyzer region 1156. The net displacement ΔX allows the ion to travel over a period of time through the analyzer region 1156 to a detector for a time of flight measurement. Because the ion mobility characteristics vary among various ion species, the various ion species become separated over time an arrive at different times at the detector 1158. Thus, a longitudinal DMS enables a differential time-of-flight analysis of various ion species.

Figure 43:
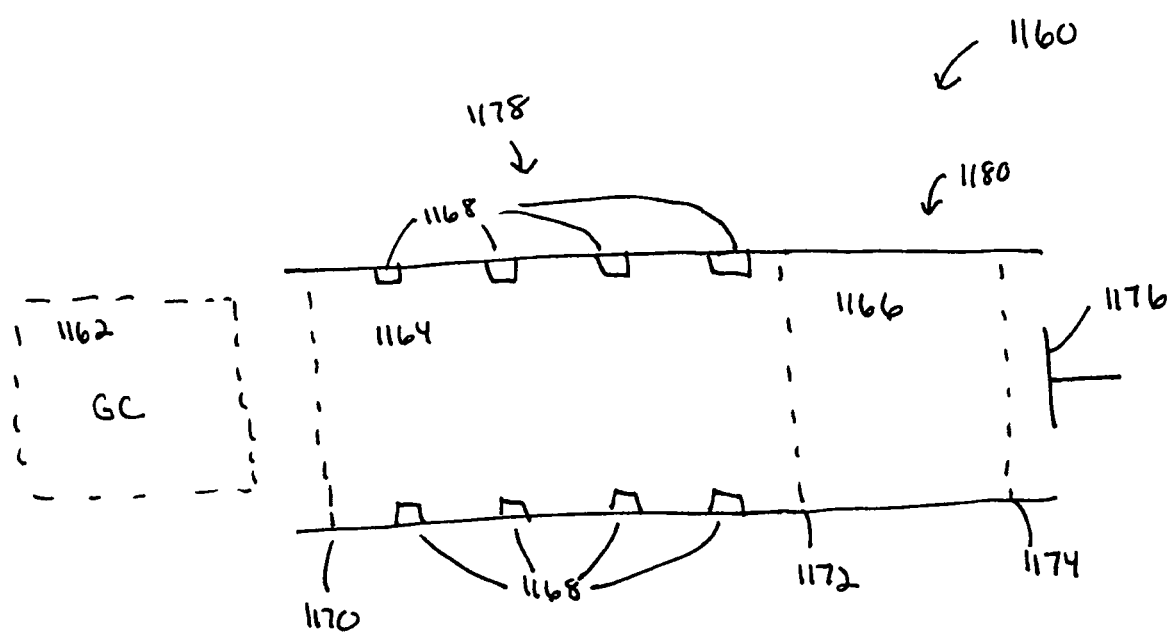
FIG. 43 is a conceptual block diagram of a GC-IMS-DMS system according to an illustrative embodiment of the invention.

FIG. 43 is a conceptual block diagram of a GC-IMS-DMS system 1160 according to an illustrative embodiment of the invention. The system includes a GC 1162, a IMS 1178, and DMS 1180. The IMS 1178 includes a drift region 1164, gradient electrodes 1168, and gate 1170. The DMS 1180 includes filter/gate electrodes 1172 and 1174, and detector 1176. In the GC 1162, sample constituents are separated with respect to time within one or more GC columns before introduction into the IMS 1178.

In the IMS 1178, gas-phase ion mobilities are determined using a drift tube and/or region 1164 with a constant electric field generated by gradient electrodes 1168. Ions are gated into the drift region 1164 by gate 1170 and are subsequently separated depending upon differences in their drift velocity. The ion drift velocity is proportional to the electric field strength at low electric field strength, for example 200 V/cm, and the mobility, K, which is determined from experimentation, which is independent of the applied electric field. Additionally, in the IMS 1178, the ions travel through a bath gas that is at sufficiently high pressure such that the ions rapidly reach constant velocity when driven by the force of an electric field that is constant both in time and location.

In the DMS 1180, the ions are then subjected to a longitudinal time-varying electric field between filter electrodes 1172 and 1174. Filter electrode 1172 may gate ions into the analyzer region 1166 which are separated with respect to time before reaching the detector 1176. The system 1160 may includes an array of GCs, array of IMSs, and an array of DMSs, integrated within an integrated package.

In certain embodiments, the GC-DMS system 600 and/or sensor 1000 are implemented in an ultra compact form factor. Having such a small form factor, the GC-DMS system 600 may be integrated with a PCMCIA card, a SD Card, and/or a computer attachable device, or wireless capability such as Zigbee and 802 based communication protocols. In one embodiment, the small form factor sensor unit 1000 is easily and unobtrusively attachable/detachable to a computing device such as a PC, laptop, PDA, cellular telephone, smartphone, or any other computing device. The ultra compact GC-DMS system 600 and/or 1000 may be integrated within a device supporting other functions such as a smoke detector, environmental sensor, flashlight, cellular telephone, wearable electronic/computing device, chemical dosimeter, and like compact portable devices.

In certain embodiments, the DMS analyzer of any of the foregoing GC-DMS systems may include a narrow filter and/or flow path gap distance. The analytical gap between at least two filter electrodes (or a one filter electrode and a conductive element or surface) may be less than about 10 nanometer ($10^{-9}$ meters), less than about 20 nanometers, less than about 50 nanometers, less than about 100 nanometers, less than about 200 nanometers, less than about 500 nanometers, less than about 1 micron ($10^{-6}$ meters), less than about 5 microns, less than about 10 microns, less than about 15 microns, less than about 20 microns, less than about 25 microns, less than about 50 microns, less than about 100 microns, less than about 150 microns, and less than about 200 microns. Depending on the gap distance, the DMS may include a peak asymmetric field voltage of less than about 10 volts, less than about 20 volts, less than about 50 volts, less than about 100 volts, less than about 200 volts, less than about 500 volts, less than about 1000 volts, and less than about 1500 volts. Additionally, the DMS analyzer may employ an asymmetric voltage operating at frequencies of greater than about 1 MHz, greater than about 5 MHz, greater than about 10 MHz, greater than about 50 MHz, greater than about 100 MHz, greater than about 500 MHz, and greater than about 1 GHz. In one embodiment, the DMS analyzer includes multiple gap distances to enable enhanced detection using multiple different analytical gaps and/or multiple DMS analyzers in series and/or parallel (e.g., an array of analyzers).

In another embodiment, any of the foregoing GC-DMS systems may include a monolithic sensor design where one or more sub-assembly pieces are bonded into a final monolithic sensor part. The final part does not require mechanical clamping to hold these pieces together to form gas-tight part. The monolithic and/or solid sensor design may include a structure formed by the low temperature co-fired ceramic (LTCC) process and/or standard, an enhanced LTCC process, an alumina-LTCC hybrid process, a polymer build from sheets process, a polymer build from injection molded parts, and/or a wrapped flex process.

In a further embodiment, any of the foregoing GC-DMS systems may include a liquid crystal polymer (LCP) board/housing for the DMS analyzer and/or GC column. By employing a LCP material for the sensor, a GC-DMS system provides an alternative to traditional polyimide film for use as a substrate in flexible circuit construction. Depending on the manufacturing technique, the LCP material eliminates certain inherent limitations of polyimide circuits. The LCP material also provides advantages to enhanced electronic device design with good electrical performance and processing capabilities such as a lower dielectric constant. The lower dielectric constant allows faster electric signal transfer, and lower moisture absorption which leads to higher frequency signal and data processing.

According to one embodiment, a compact integrated ion mobility based analysis system includes at least one gas chromatograph (GC) column and at least one ion mobility based sample analyzer. Optionally, the at least one GC and the at least one ion mobility based sample analyzer are formed as an integrated circuit in a single package. The GC column receives a sample and elutes constituents of the sample, each of the eluted constituents being temporally separated from each other. The mobility based sample analyzer receives the eluted constituents from the GC and analyzes them based on their ion mobility characteristics of the eluted constituents. According to one feature of the invention, both the carrier gas in the at least one GC column and the drift gas in the at least one ion mobility based sample analyzer consist substantially of air.

According to one feature, the at least one GC column is formed as a capillary column in a substrate. The at least one GC column may be configured, for example, to include a spiral portion, and/or a spiral/counter-spiral portion on the substrate. It may also be configured to have one or more straight portions and one or more curved portions. The spirals may trace a plurality of any suitable geometric patterns including, for example, an oval, triangle or rectangle. According to various configurations, the at least one GC column has a length of less than about 20 meters, 10 meters, 8 meters, 6 meters, 4 meters, 2 meters, or 1 meter, or 100 cm, or 10 cm, or 1 cm. The substrate on which the GC column is formed may be made, for example, from silicon, GaAs, sapphire, alumina, plastic polymer, or other substrate material.

According to one configuration, the least one ion mobility based sample analyzer includes a differential mobility spectrometer (DMS). In some embodiments, the at least one ion mobility based sample analyzer includes an array of ion mobility based sample analyzers. In one implementation, a subset of the array of ion mobility based sample analyzers operate in parallel, series, and/or a combination of series and parallel with each other. According to one configuration, first and second ones of the array of ion mobility based sample analyzers have first and second flow channels, respectively, where the first and second flow channels share a common ion filter. Optionally, they also share a common flow channel from the ion filter through a detector region. In an alternative configuration, the first and second flow channels may be isolated, in whole or in part, from each other. According to one application, an eluted sample from the GC column is flowed into the array of ion mobility based sample analyzers, each having a different Vcomp applied to the ion filter. In this way, the equivalent of a Vcomp scan can be achieved with multiple concurrent measurements.

According to another configuration, at least one of the array of ion mobility based sample analyzers is an ion mobility spectrometer (IMS). In one configuration, the at least one ion mobility sample analyzer is formed at an intermediate location along a length of the GC column intermediate to first and second terminal ends of the GC column. In a further embodiment of this configuration, constituents are eluted from the GC column at the second end and are flowed into a second ion mobility sample analyzer. According to another configuration, the at least one GC column is a single GC column that provides the eluted constituents to each of an array of ion mobility based sample analyzers.

The at least one GC column and the at least one ion mobility based sample analyzer may be formed on a single substrate. Alternatively, they may be formed on separate substrates. According to some configurations, the at least one GC column and the at least one ion mobility based sample analyzer system are formed, at least in part, on a common substrate. According to other configurations, the at least one GC column is located on a different substrate from that of the at least one ion mobility based sample analyzer. In multiple substrate configurations, one or more substrates may be vertically stacked relative to each other. Alternatively, one or more substrates may be located horizontally adjacent to each other. In either case, first and second ones of the at least one ion mobility based sample analyzer may be located on different substrates. According to one feature, the components on the substrates are functionally interconnected.

According to some embodiments, the system of the invention includes an inlet for providing a make up effluent to the at least one ion mobility based sample analyzer to increase a flow rate of the eluted constituent from the at least one GC column to a level suitable for the at least one ion mobility based sample analyzer. In various implementations, the flow rate from the at least one GC column is less than about 1 ml/min; 2 ml/min, 4 ml/min, 6 ml/min, 8 ml/min, or 10 ml/min. In other implementations, the makeup flow provides a flow rate from through the at least ion mobility based sample analyzer of at least about 1 l/min, 1.5 l/min, 2 l/min or 3 l/min.

According to other embodiments, the invention includes at least one heater for heating the at least one GC column. In further embodiments, the system of the invention includes at least one air gap between the least one ion mobility based sample analyzer and the at least one GC column for providing thermal and/or electrical isolation. The system may also include cutouts for providing thermal and/or electrical separation between the at least one GC column and the at least one ion mobility based sample analyzer.

According to one embodiment, the system of the invention analyzes a sample by flowing the sample through the at least one GC column to temporally separate constituents of the sample from each other, and analyzes at least one of the eluted constituents from the at least one GC column based on the ion mobility characteristics of the constituents. In some embodiments, the system of the invention analyzes a plurality of eluted constituents from the at least one GC column concurrently or substantially simultaneously.

In a further embodiment, the at least one ion mobility based sample analyzer of the invention has low enough sample residence times and operates fast enough to provide a plurality of scans over a range of field conditions (e.g., field compensation voltage (Vcomp), radio frequency field excitation voltage (Vrf), and the like) for a single elution peak from the at least one GC column. In one implementation the at least one ion mobility based sample analyzer has a sample residence time of less than about 1 second, 500 ms, 250 ms, 100 ms, 50 ms, 25 ms, 10 ms, 5 ms, or 1 ms. According to one feature, the at least one ion mobility based sample analyzer is sized and shaped to perform a single measurement of at least a portion of one of the eluted constituents from the GC column at a particular filter field condition in less than about 100 ms, 50 ms, 25 ms, 10 ms, 5 ms, 2 ms, or 1 ms. Or more than 100 ms.

According to another feature, the at least one ion mobility based sample analyzer performs a scanned measurement of at least one of the eluted constituents from the GC column over a range of field compensation voltages of at least about 50 Vdc in less than about 10 second, 5 seconds, 4 seconds, 3 seconds, 2 seconds, or 1 second. Alternatively, the at least one ion mobility based sample analyzer performs a scanned measurement of at least one of the eluted constituents from the GC column over a range of field compensation voltages of at least about 100 Vdc in less than about 10 seconds, 5 second, 4 seconds, 3 seconds, 2 seconds, or 1 second.

According to another aspect, the invention corrects detection data for an ion mobility based analyzer by introducing a known sample concentration having a predictable time-dependent concentration distribution profile into the analyzer. Then, the invention measures the concentration for the known sample in the analyzer and generating a measured time-dependent concentration distribution profile for the known sample. Further, the invention processes the measured and predictable time-dependent concentration distribution profiles to determine a response correction function for the analyzer and employs the response correction function for the analyzer to correct subsequent detection data from analyzer.

The response correction function may be inverted prior to employing it to correct the subsequent detection data from the analyzer. According to one embodiment, the invention derives parameters that define the measured time-dependent concentration distribution profile, and employs those parameters to determine the response correction function for the analyzer. Furthermore, the invention may process the parameters in a generic response correction function to determine a particular response correction function for the analyzer. In some embodiments, the generic response function is determined by experimentation. Alternatively, the invention may employ mathematical calculations, theoretical formulas, and/or thermodynamic equilibrium equations as the generic response function.

In certain illustrative embodiments of the invention, the predictable time-dependent concentration distribution profile may be a Gaussian profile. The invention may measure the concentration for the known sample by measuring the ion intensity for the known sample. The invention may also compensate for gas chromatographic tailing in the response correction function for the analyzer.

It will be apparent to those of ordinary skill in the art that certain algorithms and methods involved in the present invention may be embodied in a computer program product that includes a computer usable and/or readable medium. For example, such a computer usable medium may consist of a read only memory device, such as a CD ROM disk or conventional ROM devices, or a random access memory, such as a hard drive device or a computer diskette, having a computer readable program code stored thereon.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compact integrated ion mobility based analysis system comprising,
    at least one gas chromatograph (GC) column for receiving a sample and for eluting constituents of the sample, wherein each of the eluted constituents are temporally separated from each other,
    at least one ion mobility based sample analyzer for analyzing the eluted constituents based on ion mobility characteristics of the eluted constituents, and
    a controller for selectively adjusting the temperature within the at least one GC column over a period of time and selectively adjusting the temperature within the at least one ion mobility based sample analyzer over a period of time, wherein the controller comprises a computer readable medium containing instructions that cause the controller to operate such that it coordinates the adjusting of the temperature within the at least one GC column with the adjusting of the temperature within the at least one ion mobility based sample analyzer.

2. The system of claim 1, wherein the at least one GC column includes an array of GC columns.

3. The system of claim 2, wherein the at least one GC column includes first and second GC columns, the first GC column having a different stationary phase than the second GC column.

4. The system of claim 3 comprising a modulator for trapping and focusing the concentration of constituents eluted from the first GC column over a period of time and delivering the constituents to the second GC column.

5. The system of claim 1, wherein the at least one GC column is formed as a capillary column in a substrate.

6. The system of claim 5, wherein the substrate is a silicon substrate.

7. The system of claim 5, wherein the substrate is a polymer-based substrate.

8. The system of claim 1, wherein the ion mobility based sample analyzer provides a plurality of scans for a single elution peak of the GC column.

9. The system of claim 1, wherein adjusting includes ramping the temperature over a range of temperatures.

10. The system of claim 9, wherein the range of temperatures includes about 0 to 350° C.

11. The system of claim 1, wherein adjusting includes stepping the temperature over a range of temperatures.

12. The system of claim 1 comprising an inlet section for conditioning the sample before introduction into the GC column.

13. The system of claim 12, wherein the inlet section includes a trap.

14. The system of claim 13, wherein the controller controls the temperature of the trap.

15. The system of claim 14, wherein the range of temperatures includes about 0 to 350° C.

16. The system of claim 12, wherein the inlet section includes at least one of pre-concentrator, electrospray source, molecular sieve, filter, pyrolizer, and ion mobility based filter.

17. The system of claim 1 comprising a fluid recirculation system for transporting portions of the sample though the GC column and the ion mobility based analyzer.

18. The system of claim 17, wherein the controller controls components of the recirculation system to enable sample collection, GC column loading, and ion mobility based analyzer analyzing.

19. The system of claim 18, wherein the components include at least one of a pump, valve, and vent.

20. The system of claim 1 comprising at least one heater for heating the GC column or at least one cooler for cooling the GC column.

21. A method for analyzing a sample comprising,
    flowing the sample though at least one GC column to temporally separate constituents of the sample while selectively adjusting the temperature within the at least one GC column over a period of time,
    flowing the temporally separated constituents though a filter region of an ion mobility based sample analyzer and selectively adjusting the temperature within the filter region of the ion mobility based sample analyzer over a period of time,
    coordinating the adjusting of the temperature within the at least one GC column with the adjusting of the temperature within the at least one ion mobility based sample analyzer, and analyzing the sample, based at least in part, on information from the ion mobility based sample analyzer.

22. The method of claim 21, wherein the at least one GC column includes an array of GC columns.

23. The method of claim 21, wherein the at least one GC column includes first and second GC columns, the first GC column having a different stationary phase than the second GC column.

24. The method of claim 23 comprising trapping and focusing the concentration of constituents eluted from the first GC column over a period of time and flowing the constituents to the second GC column.

25. The method of claim 21, wherein the at least one GC column is formed as a capillary column in a substrate.

26. The method of claim 25, wherein the substrate is a silicon substrate.

27. The method of claim 25, wherein the substrate is a polymer-based substrate.

28. The method of claim 21 comprising performing a plurality of scans for a single elution peak of the at least one GC column.

29. The method of claim 21, wherein adjusting includes ramping the temperature over a range of temperatures.

30. The method of claim 29, wherein the range of temperatures includes about 0 to 350° C.

31. The method of claim 21, wherein adjusting includes stepping the temperature over a range of temperatures.

32. The method of claim 21 comprising conditioning the sample before flowing the sample though the at least one GC column.

33. The method of claim 32, wherein the conditioning includes trapping the sample.

34. The method of claim 33 comprising controlling the temperature of the sample while trapping the sample.

35. The method of claim 34, wherein the range of temperatures includes about 0 to 350° C.

36. The method of claim 32, wherein the conditioning includes subjecting the sample to at least one of a pre-concentrator, an electro spray source, a molecular sieve, a filter, a pyrolizer, and an ion mobility based filter.

37. The method of claim 21 comprising using a recirculation system to transport portions of the sample though the GC column and the ion mobility based analyzer.

38. The method of claim 37, wherein the recirculation system provides gas flow to enable at least one of sample collection, GC column loading, and ion mobility based analyzer analyzing.

39. The method of claim 38, wherein the recirculation system includes at least one of a pump, valve, and vent.

40. The method of claim 21 comprising using at least one heater for heating the GC column or at least one cooler for cooling the GC column.

41. The system of claim 1, wherein the at least one ion mobility based sample analyzer includes a differential mobility spectrometer.

42. The system of claim 1, wherein coordinates includes synchronizes.

43. The method of claim 21, wherein the ion mobility based sample analyzer includes a differential mobility spectrometer.

44. The method of claim 21, wherein coordinating includes synchronizing.

* * * * *